US011420177B2

(12) United States Patent
Sookraj

(10) Patent No.: US 11,420,177 B2
(45) Date of Patent: Aug. 23, 2022

(54) FLEXIBLE CHEMICAL PRODUCTION METHOD

(71) Applicant: Novomer, Inc., Rochester, NY (US)

(72) Inventor: Sadesh H. Sookraj, Rochester, NY (US)

(73) Assignee: Novomer, Inc., Rochester, NY (US)

( * ) Notice: Subject to any disclaimer, the term of this patent is extended or adjusted under 35 U.S.C. 154(b) by 231 days.

(21) Appl. No.: 16/890,056

(22) Filed: Jun. 2, 2020

(65) Prior Publication Data

US 2020/0298199 A1 Sep. 24, 2020

Related U.S. Application Data

(62) Division of application No. 15/550,153, filed as application No. PCT/US2016/017861 on Feb. 12, 2016, now abandoned.

(60) Provisional application No. 62/116,234, filed on Feb. 13, 2015.

(51) Int. Cl.
| | |
|---|---|
| *C08G 63/08* | (2006.01) |
| *B01J 19/24* | (2006.01) |
| *C07C 67/03* | (2006.01) |
| *C07D 305/12* | (2006.01) |
| *C07D 307/60* | (2006.01) |
| *C07D 307/08* | (2006.01) |
| *C07D 307/33* | (2006.01) |
| *C07C 51/09* | (2006.01) |
| *C07D 301/03* | (2006.01) |
| *C08G 63/78* | (2006.01) |
| *C07C 29/147* | (2006.01) |
| *C07C 29/132* | (2006.01) |
| *B01J 19/00* | (2006.01) |
| *C07C 29/149* | (2006.01) |
| *C08J 11/12* | (2006.01) |

(52) U.S. Cl.
CPC ....... *B01J 19/2445* (2013.01); *B01J 19/0006* (2013.01); *B01J 19/245* (2013.01); *C07C 29/132* (2013.01); *C07C 29/147* (2013.01); *C07C 29/149* (2013.01); *C07C 51/09* (2013.01); *C07C 67/03* (2013.01); *C07D 301/03* (2013.01); *C07D 305/12* (2013.01); *C07D 307/08* (2013.01); *C07D 307/33* (2013.01); *C07D 307/60* (2013.01); *C08G 63/08* (2013.01); *C08G 63/78* (2013.01); *C08G 63/785* (2013.01); *C08J 11/12* (2013.01); *B01J 2219/00049* (2013.01); *B01J 2219/24* (2013.01); *C08J 2367/04* (2013.01)

(58) Field of Classification Search
USPC ................ 528/359, 361, 378, 379
See application file for complete search history.

(56) References Cited

U.S. PATENT DOCUMENTS

| | | | |
|---|---|---|---|
| 2,352,641 A | 7/1944 | Kung | |
| 2,361,036 A | 10/1944 | Kung | |
| 2,376,704 A | 5/1945 | Kung | |
| 2,449,995 A | 9/1948 | Gresham | |
| 2,466,501 A | 4/1949 | Steadman et al. | |
| 2,485,510 A | 10/1949 | Redmon | |
| 2,510,423 A | 6/1950 | Shaver | |
| 2,548,155 A | 4/1951 | Gresham et al. | |
| 2,623,067 A | 12/1952 | Beears et al. | |
| 3,136,623 A | 6/1964 | Mader | |
| 3,169,945 A | 2/1965 | Hostettler | |
| 3,176,042 A | 3/1965 | Schnizer et al. | |
| 3,678,069 A | 7/1972 | Busler | |
| 5,359,081 A | 10/1994 | Drent et al. | |
| 5,648,452 A | 7/1997 | Schechtman et al. | |
| 6,133,402 A | 10/2000 | Coates et al. | |
| 6,316,590 B1 | 11/2001 | Coates et al. | |
| 6,492,535 B1 | 12/2002 | Castiglioni et al. | |
| 6,538,101 B2 | 3/2003 | Coates et al. | |
| 6,608,170 B1 | 8/2003 | Coates | |
| 7,420,064 B2 | 9/2008 | Luinstra et al. | |
| 8,445,703 B2 | 5/2013 | Allen et al. | |
| 8,481,756 B1 | 7/2013 | Coates et al. | |

(Continued)

FOREIGN PATENT DOCUMENTS

| | | |
|---|---|---|
| CN | 1255914 A | 6/2000 |
| CN | 103987682 A | 8/2014 |

(Continued)

OTHER PUBLICATIONS

Notice of Decision in co-pending application SA517382088, dated Dec. 28, 2020.

(Continued)

*Primary Examiner* — Terressa Boykin

(74) *Attorney, Agent, or Firm* — Young Basile Hanlon & MacFarlane, P.C.

(57) ABSTRACT

Disclosed herein is a method for converting an epoxide to a first C3 product, a second C3 product, and/or a first C4 product within an integrated system. The method includes converting the epoxide to a beta lactone to produce an outlet stream comprising beta lactone. The method includes converting the beta lactone of the outlet stream to a first C3 product in the first C3 reactor to produce an outlet stream comprising the first C3 product; converting the beta lactone to a second C3 product in the second C3 reactor to produce an outlet stream comprising the second C3 product, and/or converting the beta lactone to a first C4 product in the first C4 reactor to produce an outlet stream comprising the first C4 product.

20 Claims, 1 Drawing Sheet

(56) References Cited

U.S. PATENT DOCUMENTS

| | | |
|---|---|---|
| 8,796,475 B2 | 8/2014 | Allen et al. |
| 9,096,510 B2 | 8/2015 | Porcelli et al. |
| 9,156,803 B2 | 10/2015 | Allen et al. |
| 9,206,144 B2 | 12/2015 | Allen et al. |
| 9,327,280 B2 | 5/2016 | Lee et al. |
| 9,403,788 B2 | 8/2016 | Lee et al. |
| 9,493,391 B2 | 11/2016 | Allen et al. |
| 9,738,784 B2 | 8/2017 | Allen et al. |
| 9,914,689 B2 | 3/2018 | Porcelli et al. |
| 10,065,914 B1 | 9/2018 | Ruhl et al. |
| 10,099,988 B2 | 10/2018 | Farmer et al. |
| 10,099,989 B2 | 10/2018 | Sookraj |
| 10,144,802 B2 | 12/2018 | Sookraj |
| 10,221,150 B2 | 3/2019 | Farmer et al. |
| 10,221,278 B2 | 3/2019 | Lee et al. |
| 10,245,559 B2 | 4/2019 | Lapointe et al. |
| 10,428,165 B2 | 10/2019 | Sookraj |
| 10,457,624 B2 | 10/2019 | Sookraj et al. |
| 10,479,861 B2 | 11/2019 | Lee et al. |
| 2005/0014977 A1 | 1/2005 | Drent et al. |
| 2007/0161806 A1 | 7/2007 | Preishuber-Pflugl et al. |
| 2009/0178495 A1 | 7/2009 | Steigmiller et al. |
| 2012/0123137 A1 | 5/2012 | Allen et al. |
| 2013/0165670 A1 | 6/2013 | Allen et al. |
| 2013/0209775 A1 | 8/2013 | Allen et al. |
| 2013/0281715 A1 | 10/2013 | Allen et al. |
| 2014/0018570 A1 | 1/2014 | Pazicky et al. |
| 2014/0275575 A1 | 9/2014 | Allen et al. |
| 2014/0296522 A1 | 10/2014 | Lee et al. |
| 2014/0309399 A1* | 10/2014 | Porcelli .......... C08G 63/08 528/359 |
| 2015/0005513 A1 | 1/2015 | Lee et al. |
| 2015/0141693 A1 | 5/2015 | Allen et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0288057 A1 | 10/2016 | Lapointe et al. |
| 2017/0001946 A1 | 1/2017 | Sookraj |
| 2017/0002136 A1 | 1/2017 | Sookraj |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0153746 A1 | 6/2018 | Sookraj |
| 2018/0155490 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |
| 2018/0305289 A1 | 10/2018 | Sookraj et al. |
| 2018/0354881 A1 | 12/2018 | Farmer et al. |
| 2018/0354882 A1 | 12/2018 | Sookraj |
| 2019/0002293 A1 | 1/2019 | Sookraj et al. |
| 2019/0002385 A1 | 1/2019 | Sookraj et al. |
| 2019/0002400 A1 | 1/2019 | Sookraj |
| 2019/0030520 A1 | 1/2019 | Lee |
| 2019/0031592 A1 | 1/2019 | Sookraj et al. |
| 2019/0047972 A1 | 2/2019 | Sookraj |
| 2019/0071388 A1 | 3/2019 | Sookraj |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |
| 2019/0106533 A1 | 4/2019 | Sookraj |
| 2019/0255488 A1 | 8/2019 | Lapointe et al. |
| 2019/0255512 A1 | 8/2019 | Lee et al. |
| 2019/0256650 A1 | 8/2019 | Lee et al. |
| 2019/0315702 A1 | 10/2019 | Sookraj et al. |

FOREIGN PATENT DOCUMENTS

| | | |
|---|---|---|
| CN | 104245657 A | 12/2014 |
| CN | 104245659 A | 12/2014 |
| EP | 2395067 A1 | 12/2011 |
| GB | 994091 A | 6/1965 |
| WO | 2003050154 A2 | 6/2003 |
| WO | 2004089923 A1 | 10/2004 |
| WO | 2010118128 A1 | 10/2010 |
| WO | 2012030619 A1 | 3/2012 |
| WO | 2012/051219 A2 | 4/2012 |
| WO | 2012158573 A1 | 11/2012 |
| WO | 2013063191 A1 | 5/2013 |
| WO | 2013122905 A1 | 8/2013 |
| WO | 2013126375 A1 | 8/2013 |
| WO | 2014004858 A1 | 1/2014 |
| WO | 2014008232 A2 | 1/2014 |
| WO | 2015085295 A2 | 6/2015 |
| WO | 2015138975 A1 | 9/2015 |
| WO | 2015171372 A1 | 11/2015 |
| WO | 2015184289 A1 | 12/2015 |
| WO | 2016015019 A1 | 1/2016 |
| WO | 2016130947 A1 | 8/2016 |
| WO | 2016130977 A1 | 8/2016 |
| WO | 2016130988 A1 | 8/2016 |
| WO | 2016130993 A1 | 8/2016 |
| WO | 2016130998 A1 | 8/2016 |
| WO | 2016131001 A1 | 8/2016 |
| WO | 2016131004 A1 | 8/2016 |
| WO | 2017/004455 A1 | 1/2017 |
| WO | 2017/004477 A2 | 1/2017 |
| WO | 2017/023777 A1 | 2/2017 |
| WO | 2017/023820 A1 | 2/2017 |
| WO | 2017/165323 A1 | 9/2017 |
| WO | 2017165344 A1 | 9/2017 |
| WO | 2017165345 A1 | 9/2017 |
| WO | 2018/085251 A1 | 5/2018 |
| WO | 2018/085254 A1 | 5/2018 |
| WO | 2018/106824 A1 | 6/2018 |
| WO | 2018/107185 A1 | 6/2018 |
| WO | 2018/136638 A1 | 7/2018 |
| WO | 2018/144998 A1 | 8/2018 |
| WO | 2018/170006 A1 | 9/2018 |
| WO | 2018/200466 A1 | 11/2018 |
| WO | 2018/200471 A1 | 11/2018 |
| WO | 2019/006366 A1 | 1/2019 |
| WO | 2019/006377 A1 | 1/2019 |
| WO | 2019/050649 A1 | 3/2019 |
| WO | 2019/051184 A1 | 3/2019 |
| WO | 2019/070981 A1 | 4/2019 |
| WO | 2019/183284 A1 | 9/2019 |
| WO | 2019/195168 A1 | 10/2019 |

OTHER PUBLICATIONS

Agostini et al., "Synthesis and Characterization of Poly-b-Hydroxybutyrate. I. Synthesis of Crystalline DL-Poly-b-Hydroxybutyrate from DL-b-Butyrolactone", Journal of Polymer Science, Part A-1, vol. 9, 1971, pp. 2775-2787.

Billingham et al., "Polymerization and Copolymerizationof b-Butyrolactone by Aluminium Compounds", Journal of Organometallic Chemistry, vol. 341, No. 1-3, 1988, pp. 83-89.

Church et al., "Carbonylation of Heterocycles by Homogeneous Catalysts", Chemical Communication, 2007, pp. 657-674.

Getzler et al., "Synthesis of b-Lactones: A Highly Active and Selective Catalyst for Epoxide Carbonylation", Journal of the American Chemical Society. vol. 124, No. 7, 2002, pp. 1174-1175.

Gross et al., "Polymerization of b-Monosubstituted-b-Propiolactones using Trialkylaluminum-Water Catalytic Systems

(56) References Cited

OTHER PUBLICATIONS and Polymer Characterization", Macromolecules, vol. 21, No. 9, 1988, pp. 2657-2668.
Hori et al., "Ring-Opening Polymerization of Optically Active b-Butyrolactone using Distannoxane Catalysts: Synthesis of High-Molecular-Weight Poly (3-Hydroxybutyrate)", Macromolecules, vol. 26, No. 20, 1993, pp. 5533-5534.
International Preliminary Report on Patentability received for PCT Patent Application No. PCT/US2016/017861, dated Aug. 24, 2017, 23 pages.
International Search Report and Written Opinion received for PCT Patent Application No. PCT/US2016/017861, dated Apr. 29, 2016, 25 pages.
Kowalczuk et al., "New Reactions of Potassium Naphthalenide with b-, y- and o-Lactones: An Efficient Route to ?-Alkyl y- and o-Lactones and ?, b-Unsaturated Carboxylic Acid Esters", The Journal of Organic Chemistry, vol. 57, No. 1, 1992, pp. 389-391.
Office Action for co-pending Chinese Application No. 201680019272.3 dated Mar. 20, 2020. 16 pages.
Rieth et al., "Single-Site Beta-Diiminate Zinc Catalysts for the Ring-Opening Polymerization of Beta-Butyrolactone and Beta-Valerolactone to Poly (3-Hydroxyalkanoates).", Journal of the American Chemical Society, vol. 124, No. 51, 2002, pp. 15239-15248.
Schechtman et al., "Chemical Synthesis of Isotactic Poly(3-Hydroxyalkanoates)", Polymer Preprints, Division of Polymer Chemistry, Inc., vol. 40, No. 1, 1999, pp. 508-509.
Tanahashi et al., "Thermal Properties and Stereoregularity of Poly (3-Hydroxybutyrate) prepared from Optically Active b-Butyrolactone with a Zinc-based Catalyst", Macromolecules, vol. 24, No. 20, 1991, pp. 5732-5733.
Zhang et al., "Stereochemistry of the Ring-Opening Polymerization of (S)-b-Butyrolactone", Macromolecules, vol. 23, No. 13, 1990, pp. 3206-3212.

\* cited by examiner

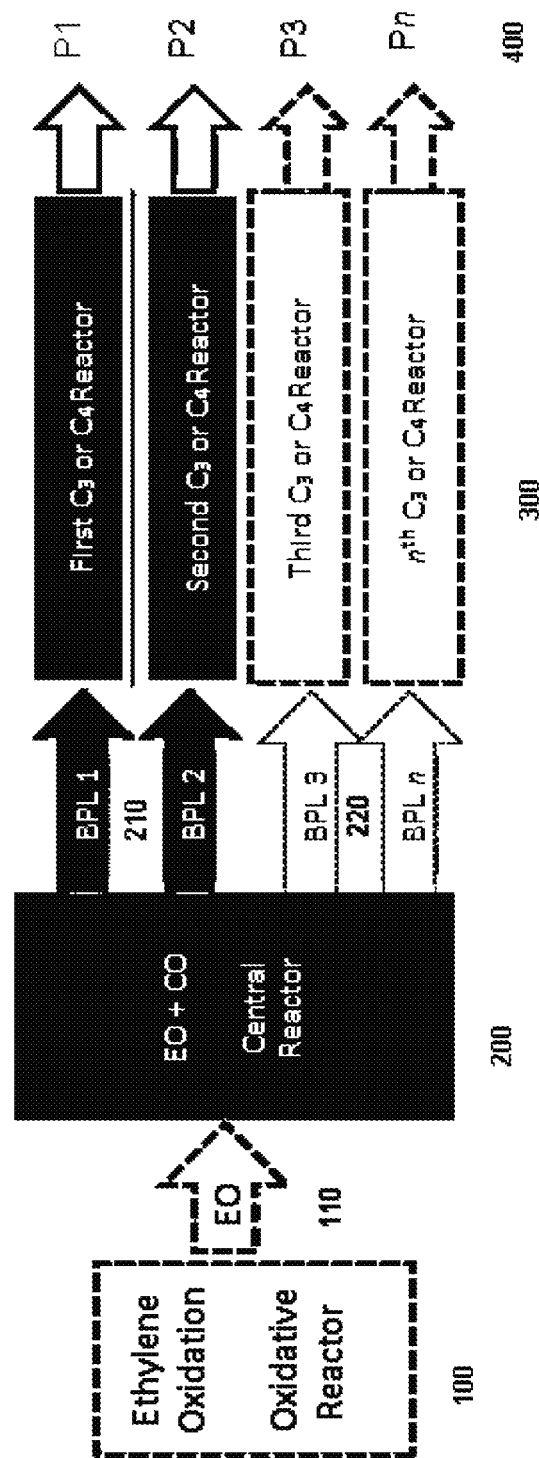

FLEXIBLE CHEMICAL PRODUCTION METHOD

CROSS-REFERENCE TO RELATED APPLICATIONS

This application is a divisional application of U.S. Non-provisional application Ser. No. 15/550,153 filed on Aug. 10, 2017, published as U.S. Publication No. 2018/0029005, which is a National Stage Patent Application of PCT/US2016/017861, filed on Feb. 12, 2016, which claims priority to and benefit of U.S. Provisional Patent Application No. 62/116,234, filed on Feb. 13, 2015, each of which is incorporated herein by reference in its entirety.

FIELD

The present disclosure relates generally to the production of chemicals, and more specifically to the conversion of epoxides to various $C_3$ products and/or $C_4$ products, such as acrylic acid and acid anhydrides.

BACKGROUND

Industrial-scale production of most chemicals generally relies upon devoted synthetic precursors, chemical transformations and production plants that cannot easily accommodate or integrate the production of other chemicals. For example, production of three-carbon-containing $C_3$ chemicals, such as acrylic acid (AA) and esters thereof, and that of four-carbon-containing $C_4$ chemicals, such as succinic anhydride (SA), generally proceed from distinct precursors via unrelated transformations that require specialized plants and methods.

Acrylic acid ($C_3$) is primarily produced via vapor phase oxidation of $C_3$ propylene, involving two reactors in series, utilizing separate catalysts. In this arrangement, the first reactor converts propylene to $C_3$ acrolein and the second reactor converts acrolein to AA. The production of acid anhydrides, including $C_4$ succinic anhydride, generally proceeds via distinct synthetic transformations, such as dehydration of the corresponding $C_4$ acids or hydrogenation of $C_4$ maleic anhydride.

There is a need to develop flexible methods and centralized systems for the production of distinct product trains from a common synthetic precursor. Such methods and systems would be of particular value if they could modulate relative production of distinct product trains as needed.

BRIEF SUMMARY

Provided herein are methods and systems that consolidate multiple product trains into a single facility that would allow producers to respond quickly to changes in market demand for each product and reduce their present reliance upon the transportation of certain production intermediates, some of which like acrylic acid are highly reactive and dangerous.

In one aspect, provided are integrated systems suitable for effecting the conversion of epoxides to multiple $C_3$ products and/or $C_4$ products. In certain embodiments, a system is provided for the production of chemicals, comprising:
a central reactor, comprising an inlet fed by an epoxide source and a carbon monoxide (CO) source, a central reaction zone that converts at least some of the epoxide to a beta lactone, and an outlet which provides an outlet stream comprising the beta lactone,
two or more of:
(i) a first $C_3$ reactor, comprising an inlet fed by the outlet stream comprising beta lactone of the central reactor, a first $C_3$ reaction zone that converts at least some of the beta lactone to a first $C_3$ product, and an outlet which provides an outlet stream comprising the first $C_3$ product,
(ii) a second $C_3$ reactor, comprising an inlet fed by the outlet stream comprising beta lactone of the central reactor, a second $C_3$ reaction zone that converts at least some of the beta lactone to a second $C_3$ product, and an outlet which provides an outlet stream comprising the second $C_3$ product, and
(iii) a first $C_4$ reactor, comprising an inlet fed by the outlet stream comprising beta lactone of the central reactor, a first $C_4$ reaction zone that converts at least some of the beta lactone to a first $C_4$ product, and an outlet which provides an outlet stream comprising the first $C_4$ product, and
a controller for independently modulating production of the beta lactone and each of the products,
with the provision that the first $C_3$ product differs from the second $C_3$ product.

In some variations, provided is a system for the production of $C_3$ and $C_4$ products, comprising:
an epoxide source;
a carbon monoxide (CO) source;
a central reactor, comprising:
an inlet configured to receive epoxide from the epoxide source and CO from the CO source,
a central reaction zone configured to convert at least some of the epoxide to a beta lactone, and
an outlet configured to provide an outlet stream comprising the beta lactone,
two or more of (i)-(iii):
(i) a first $C_3$ reactor, comprising:
an inlet configured to receive the outlet stream comprising beta lactone of the central reactor,
a first $C_3$ reaction zone configured to convert at least some of the beta lactone to a first $C_3$ product, and
an outlet configured to provide an outlet stream comprising the first $C_3$ product,
(ii) a second $C_3$ reactor, comprising:
an inlet configured to receive the outlet stream comprising beta lactone of the central reactor,
a second $C_3$ reaction zone configured to convert at least some of the beta lactone to a second $C_1$ product, and
an outlet configured to provide an outlet stream comprising the second $C_3$ product, and
(iii) a first $C_4$ reactor, comprising:
an inlet configured to receive the outlet stream comprising beta lactone of the central reactor,
a first $C_4$ reaction zone configured to convert at least some of the beta lactone to a first $C_4$ product, and
an outlet configured to provide an outlet stream comprising the first $C_4$ product, and
a controller to independently modulate production of the beta lactone and each of the products,
provided that the first $C_3$ product differs from the second $C_3$ product.

In another variation, provided is a system, comprising:
an ethylene source;
a carbon monoxide (CO) source;
an alcohol source;
an oxidative reactor comprising:
an inlet configured to receive ethylene from the ethylene source, an oxidative reaction zone configured to convert at least some of the ethylene to ethylene oxide (EO), and
an outlet configured to provide an EO stream comprising the EO;
a central reactor comprising:
an inlet configured to receive EO from the EO stream of the oxidative reactor and CO from the CO source,
a central reaction zone configured to convert at least some of the EO to beta propiolactone (BPL), and
an outlet configured to provide a BPL stream comprising the BPL;
a first C3 reactor comprising:
an inlet configured to receive BPL from at least a portion of the BPL stream of the central reactor,
a first C3 reaction zone configured to convert at least some of the BPL to a polypropiolactone (PPL), and
an outlet configured to provide a PPL stream comprising the PPL;
a second C3 reactor comprising;
an inlet configured to receive PPL from the PPL stream of the first C3 reactor,
a second C3 reaction zone configured to convert at least some of the PPL to AA, and
an outlet configured to provide an AA stream comprising the AA;
a third C3 reactor comprising:
an inlet configured to receive BPL from at least a portion of the BPL stream of the central reactor, and an alcohol from the alcohol source,
a third C3 reaction zone configured to convert at least some of the BPL to acrylate esters, and
an outlet configured to provide an acrylate ester stream comprising the acrylate esters; and
a controller to independently modulating production of the EO, BPL, PPL, AA, and acrylate esters.

In another variation, provided is a system, comprising:
an ethylene source;
a carbon monoxide (CO) source;
an alcohol source;
an oxidative reactor comprising:
an inlet configured to receive ethylene from the ethylene source,
an oxidative reaction zone configured to convert at least some of the ethylene to ethylene oxide (EO), and
an outlet configured to provide an EO stream comprising the EO;
a central reactor comprising:
an inlet configured to receive EO from the EO stream of the oxidative reactor and CO from the CO source,
a central reaction zone configured to convert at least some of the EO to beta propiolactone (BPL), and
an outlet configured to provide a BPL stream comprising the BPL;
a first C3 reactor comprising:
an inlet configured to receive BPL from at least a portion of the BPL stream of the central reactor,
a first C3 reaction zone configured to convert at least some of the BPL to a polypropiolactone (PPL), and
an outlet configured to provide a PPL stream comprising the PPL;
a second C3 reactor comprising;
an inlet configured to receive BPL from at least a portion of the BPL stream of the central reactor,
a second C3 reaction zone configured to convert at least some of the BPL to AA, and
an outlet configured to provide an AA stream comprising the AA;

a third C3 reactor comprising:
an inlet configured to receive BPL from at least a portion of the BPL stream of the central reactor, and an alcohol from the alcohol source,
a third C3 reaction zone configured to convert at least some of the BPL to acrylate esters, and
an outlet configured to provide an acrylate ester stream comprising the acrylate esters; and
a controller to independently modulating production of the EO, BPL, PPL, AA, and acrylate esters.

In yet another variation, provided is a system, comprising:
an ethylene source;
a carbon monoxide (CO) source;
an oxidative reactor comprising:
an inlet configured to receive ethylene from the ethylene source,
an oxidative reaction zone configured to convert at least some of the ethylene to ethylene oxide (EO), and
an outlet configured to provide an EO stream comprising the EO;
a central reactor comprising:
an inlet configured to receive EO from the EO stream of the oxidative reactor and CO from the CO source,
a central reaction zone configured to convert at least some of the EO to beta propiolactone (BPL), and
an outlet configured to provide a BPL stream comprising the BPL;
a first C3 reactor comprising:
an inlet configured to receive BPL from at least a portion of the BPL stream of the central reactor,
a first C3 reaction zone configured to convert at least some of the BPL to a polypropiolactone (PPL), and
an outlet configured to provide a PPL stream comprising the PPL;
a second C3 reactor comprising;
an inlet configured to receive PPL from the PPL stream of the first C3 reactor,
a second C3 reaction zone configured to convert at least some of the PPL to AA, and
an outlet configured to provide an AA stream comprising the AA;
a first C4 reactor comprising:
an inlet configured to receive BPL from at least a portion of the BPL stream of the central reactor, and carbon monoxide from the CO source,
a first C4 reaction zone configured to convert at least some of the BPL to succinic anhydride (SA), and
an outlet configured to provide a succinic anhydride stream comprising the succinic anhydride; and
a controller to independently modulating production of the EO, BPL, PPL, AA, and SA.

In yet another variation, provided is a system, comprising:
an ethylene source;
a carbon monoxide (CO) source;
an alcohol source;
an oxidative reactor comprising:
an inlet configured to receive ethylene from the ethylene source,
an oxidative reaction zone configured to convert at least some of the ethylene to ethylene oxide (EO), and
an outlet configured to provide an EO stream comprising the EO,
a central reactor comprising:
an inlet configured to receive EO from the EO stream of the oxidative reactor and at least a portion of CO from the CO source, a central reaction zone configured to convert at least some of the EO to beta propiolactone (BPL), and an outlet configured to provide a BPL stream comprising the BPL;

a first C3 reactor comprising:

an inlet configured to receive BPL from at least a portion of the BPL stream of the central reactor, a first C3 reaction zone configured to convert at least some of the BPL to a polypropiolactone (PPL), and an outlet configured to provide a PPL stream comprising the PPL;

a second C3 reactor comprising;

an inlet configured to receive BPL from the BPL stream of the central reactor, a second C3 reaction zone configured to convert at least some of the BPL to AA, and an outlet configured to provide an AA stream comprising the AA;

a third C3 reactor comprising:

an inlet configured to receive BPL from at least a portion of the BPL stream of the central reactor, and an alcohol from the alcohol source, a third C3 reaction zone configured to convert at least some of the BPL to acrylate esters, and an outlet configured to provide an acrylate ester stream comprising the acrylate esters;

a first C4 reactor comprising:

an inlet configured to receive BPL from at least a portion of the BPL stream of the central reactor, and at least a portion of CO from the CO source, a first C4 reaction zone configured to convert at least some of the BPL to succinic anhydride (SA), and an outlet configured to provide a SA stream comprising the succinic anhydride; and a controller to independently modulating production of the EO, BPL, PPL, AA, acrylate esters, and SA.

In another aspect, related methods are disclosed for the conversion of epoxides to multiple $C_3$ products and/or $C_4$ products. In one variation, provided is a method for converting an epoxide to two or more of: a first $C_1$ product, a second $C_1$ product, and a first $C_4$ product within an integrated system, the method comprising:

providing an inlet stream comprising an epoxide and carbon monoxide (CO) to a central reactor of the integrated system;

contacting the inlet stream with a carbonylation catalyst in a central reaction zone;

converting at least a portion of the epoxide to a beta lactone to produce an outlet stream comprising beta lactone;

(i) directing the outlet stream comprising beta lactone from the central reaction zone to a first $C_3$ reactor, and converting at least some of the beta lactone to a first $C_3$ product in the first $C_3$ reactor to produce an outlet stream comprising the first $C_3$ product, or (ii) directing the outlet stream comprising beta lactone from the central reaction zone to a second $C_3$ reactor, and converting at least some of the beta lactone to a second $C_1$ product in the second $C_1$ reactor to produce an outlet stream comprising the second $C_3$ product, or (iii) directing the outlet stream comprising beta lactone from the central reaction zone to a first $C_4$ reactor, and converting at least some of the beta lactone to a first $C_4$ product in the first $C_4$ reactor to produce an outlet stream comprising the first $C_4$ product, provided that at least two of (i)-(iii) are selected; and obtaining two or more of the first $C_3$ product, the second $C_3$ product, and the first $C_4$ product.

In another variation, provided is a method, comprising:

providing an EO stream and a CO stream to a central reactor, wherein the EO stream comprises EO, and the CO stream comprises CO;

contacting the EO stream and the CO stream with a carbonylation catalyst in the central reactor;

converting at least a portion of the EO to produce a beta propiolactone (BPL) stream comprising BPL;

directing at least a portion of the BPL stream to a first C3 reactor;

converting at least portion of the BPL to polypropiolactone (PPL) in the first C3 reactor, to produce a PPL stream comprising the PPL from the first C3 reactor;

directing the PPL stream to a second C3 reactor;

converting at least a portion of the PPL to acrylic acid (AA) in the second C3 reactor, to produce an AA stream comprising the AA from the second C3 reactor;

directing at least a portion of the BPL stream to a third C3 reactor;

contacting the BPL stream in the third C3 reactor with an alcohol; and converting at least a portion of the BPL to acrylate esters in the third C3 reactor, to produce an acrylate ester stream comprising the acrylate esters.

In yet another variation, provided is a method, comprising:

providing an EO stream and a CO stream to a central reactor, wherein the EO stream comprises EO, and the CO stream comprises CO;

contacting the EO stream and the CO stream with a carbonylation catalyst in the central reactor;

converting at least a portion of the EO to produce a beta propiolactone (BPL) stream comprising BPL;

directing at least a portion of the BPL stream to a first C3 reactor;

converting at least portion of the BPL to polypropiolactone (PPL) in the first C3 reactor, to produce a PPL stream comprising the PPL from the first C3 reactor;

directing at least a portion of the BPL stream to a second C3 reactor;

converting at least a portion of the BPL to acrylic acid (AA) in the second C3 reactor, to produce an AA stream comprising the AA from the second C3 reactor;

directing at least a portion of the BPL stream to a third C3 reactor;

contacting the BPL stream with an alcohol in the third C3 reactor; and converting at least a portion of the BPL to acrylate esters in the third C3 reactor, to produce an acrylate ester stream comprising the acrylate esters.

In yet another variation, provided is a method, comprising:

providing an EO stream and a CO stream to a central reactor, wherein the EO stream comprises EO, and the CO stream comprises CO;

contacting the EO stream and the CO stream with a carbonylation catalyst in the central reactor;

converting at least a portion of the EO to produce a beta propiolactone (BPL) stream comprising BPL;

directing at least a portion of the BPL stream to a first C3 reactor;

converting at least portion of the BPL to polypropiolactone (PPL) in the first C3 reactor, to produce a PPL stream comprising the PPL from the first C3 reactor;

directing the PPL stream to a second C3 reactor;

converting at least some of the PPL to acrylic acid (AA) in the second C3 reactor, to produce an AA stream comprising the AA from the second C3 reactor;

directing at least a portion of the BPL stream to a first C4 reactor; and converting at least some of the BPL to succinic anhydride (SA) in the first C4 reactor, to produce a succinic anhydride stream comprising the succinic anhydride from the first C4 reactor.

In yet another variation, provided is a method, comprising:

providing an EO stream and a CO stream to a central reactor, wherein the EO stream comprises EO, and the CO stream comprises CO;

contacting the EO stream and at least a portion of the CO stream with a carbonylation catalyst in the central reactor;

converting at least a portion of the EO to produce a beta propiolactone (BPL) stream comprising BPL;

directing at least a portion of the BPL stream to a first C3 reactor;

converting at least portion of the BPL to polypropiolactone (PPL) in the first C3 reactor, to produce a PPL stream comprising the PPL from the first C3 reactor;

directing at least a portion of the BPL stream to a second C3 reactor;

converting at least a portion of the BPL to acrylic acid (AA) in the second C3 reactor, to produce an AA stream comprising the AA from the second C3 reactor;

directing at least a portion of the BPL stream to a third C3 reactor;

contacting the BPL stream with an alcohol in the third C3 reactor;

converting at least a portion of the BPL to acrylate esters in the C3 reactor, to produce an acrylate ester stream comprising the acrylate esters;

directing at least a portion of the BPL stream to a first C4 reactor;

contacting the BPL stream and at least a portion of the CO stream in the first C4 reactor; and converting at least a portion of the BPL to succinic anhydride (SA) in the first C4 reactor, to produce a SA stream comprising the SA.

The disclosed systems and methods are described in greater detail below.

BRIEF DESCRIPTION OF THE FIGURES

The present application can be best understood by reference to the following description taken in conjunction with the accompanying FIGURES, in which like parts may be referred to by like numerals.

FIG. 1 shows, in one embodiment, a representative process schematic for the disclosed systems.

DEFINITIONS

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. In some variations, the aliphatic group is unbranched or branched. In other variations, the aliphatic group is cyclic. Unless otherwise specified, in some variations, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In certain embodiments, aliphatic groups contain 1-5 carbon atoms, In certain embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, for example, linear or branched, alkyl, alkenyl, and alkynyl groups, and hybrids thereof such as (cycloalkyl) alkyl, (cycloalkcnyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "hetercyclyl," "heterocycloaliphatic," or "heterocyclic" groups. In some variations, the heteroaliphatic group is branched or unbranched. In other variations, the heteroaliphatic group is cyclic. In yet other variations, the heteroaliphatic group is acyclic.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, for example, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadicnyl. In certain embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In certain embodiments, a carbocyclic group is bicyclic. In certain embodiments, a carbocyclic group is tricyclic. In certain embodiments, a carbocyclic group is polycyclic.

The term "alkyl," as used herein, refers to a saturated hydrocarbon radical. In some variations, the alkyl group is a saturated, straight- or branched-chain hydrocarbon radicals derived from an aliphatic moiety containing between one and six carbon atoms by removal of a single hydrogen atom. Unless otherwise specified, in some variations, alkyl groups contain 1-12 carbon atoms. In certain embodiments, alkyl groups contain 1-8 carbon atoms. In certain embodiments, alkyl groups contain 1-6 carbon atoms. In certain embodiments, alkyl groups contain 1-5 carbon atoms, In certain embodiments, alkyl groups contain 1-4 carbon atoms, in yet other embodiments alkyl groups contain 1-3 carbon atoms, and in yet other embodiments alkyl groups contain 1-2 carbon atoms. Alkyl radicals may include, for example, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, and dodecyl.

The ten is "alkenyl," as used herein, denote a monovalent group having at least one carbon-carbon double bond. In some variations, the alkenyl group is a monovalent group derived from a straight- or branched-chain aliphatic moiety having at least one carbon-carbon double bond by the removal of a single hydrogen atom. Unless otherwise specified, in some variations, alkenyl groups contain 2-12 carbon atoms. In certain embodiments, alkenyl groups contain 2-8 carbon atoms. In certain embodiments, alkenyl groups contain 2-6 carbon atoms. In certain embodiments, alkenyl groups contain 2-5 carbon atoms, In certain embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, and 1-methyl-2-buten-1-yl.

The term "alkynyl," as used herein, refers to a monovalent group having at least one carbon-carbon triple bond. In some variations, the alkynyl group is a monovalent group derived from a straight- or branched-chain aliphatic moiety having at least one carbon-carbon triple bond by the removal of a single hydrogen atom. Unless otherwise specified, in some variations, alkynyl groups contain 2-12 carbon atoms. In certain embodiments, alkynyl groups contain 2-8 carbon atoms. In certain embodiments, alkynyl groups contain 2-6 carbon atoms. In certain embodiments, alkynyl groups contain 2-5 carbon atoms, In certain embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, for example, ethynyl, 2-propynyl (propargyl), and 1-propynyl.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include, for example, cyclopropane, cyclohutane, cyclopentane, cyclohexane, bicyclo[2,2,1]heptane, norbornene, phenyl, cyclohexene, naphthalene, and spiro[4.5]decane.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments, "aryl" refers to an aromatic ring system which includes, for example, phenyl, naphthyl, and anthracyl, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, and tetrahydronaphthyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 pi ($\pi$) electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-" as used herein, also include groups in which a heteroaromatic ring is fused to one or more aryl, cycloaliphatic, or heterocyclyl rings, where the radical or point of attachment is on the heteroaromatic ring. Examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and may be saturated or partially unsaturated, and have, in addition to carbon atoms, one or more, preferably one to four, heteroatoms, as defined above. In some variations, the heterocyclic group is a stable 5-to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, for example, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds described herein may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$C(O)NR$^\circ$)$_2$; —N(R$^\circ$C(S)NR$^\circ$)$_2$; —(CH$_2$)$_{0-4}$N(R$^\circ$C(O)OR$^\circ$; —N(R$^\circ$)N(R$^\circ$)C(O)R$^\circ$; —N(R$^\circ$N(R$^\circ$C(O)NR$^\circ$)$_2$; —N(R$^\circ$N(R$^\circ$C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)N(R$^\circ$2; —(CH$_2$)$_{0-4}$C(O)SR$^\circ$; —(CH$_2$)$_{0-4}$C(O)OSiR$^\circ_3$; —(CH$_2$)$_{0-4}$OC(O)R$^\circ$; —OC(O)(CH$_2$)$_{0-4}$SR$^\circ$; —SC(S)SR$^\circ$; —(CH$_2$)$_{0-4}$SC(O)R$^\circ$; —(CH$_2$)$_{0-4}$C(O)NR$^\circ_2$; —C(S)NR$^\circ_2$; —C(S)SR$^\circ$; —SC(S)SR$^\circ$; —(CH$_2$)$_{0-4}$OC(O)NR$^\circ_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ_2$; —(CH$_2$)$_{0-4}$S(O)R$^\circ$; —N(R$^\circ$S(O)$_2$NR$^\circ_2$; —N(R$^\circ$S(O)$_2$R$^\circ$; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ_2$; SiR$^\circ_3$; —(C$_{1-4}$ straight or branched)alkylene)O—N(R$^\circ_2$; or —(C$_{1-4}$ straight or branched)alkylene)C(O)O—N(R$^\circ_2$, wherein each R$^\circ$ may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur, or, notwithstanding the definition above, two independent occurrences of R$^\circ$, taken together with their intervening atom(s), form a 3-12-membered saturated, partially unsaturated, or aryl mono- or polycyclic ring having 0-4 heteroatoms independently selected from nitrogen, oxygen, and sulfur, which may be substituted as defined below.

Suitable monovalent substituents on R$^\circ$ (or the ring formed by taking two independent occurrences of R$^\circ$ together with their intervening atoms), are independently halogen, (CH$_2$)$_{0-2}$R$^\bullet$, -(halon$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-4}$C(O)N(R$^\circ_2$; —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR"$_2$, or —NO$_2$, wherein each R' is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include —R$^\dagger$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of $R^†$ are independently halogen, —R*, -(haloR*), —OH, —OR*, —O(haloR*), —CN, —C(O)OH, —C(O)OR*, —NH$_2$, —NHR*, —NR*$_2$, or —NO$_2$, wherein each R* is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "reaction zone" refers to a reactor or portion thereof where a particular reaction occurs. A given reaction may occur in multiple reaction zones, and different reaction zones may comprise separate reactors or portions of the same reactor. A "reactor" typically comprises one or more vessels with one or more connections to other reactors or system components.

As used herein, the terms "reaction stream" and "inlet stream" refer to a solid, liquid or gas medium comprising a reactant that enters a reaction zone. As used herein, the terms "product stream" and "outlet stream" refer to a solid, liquid or gas medium comprising a product that exits a reaction zone. Each reaction and product (i.e., inlet or outlet) stream may be neat with respect to reactant and product or they may include co-reactants, co-products, catalysts, solvents, carrier gas and/or impurities.

The term "polymer", as used herein, refers to a molecule comprising multiple repeating units. In some variations, the polymer is a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, the polymer may be a copolymer, terpolymer, heteropolymer, block copolymer, or tapered heteropolymer of one or more epoxides. In one variation, the polymer may be a copolymer, terpolymer, heteropolymer, block copolymer, or tapered heteropolymer of two or more monomers.

In some variations, the term "epoxide", as used herein, refers to a substituted or unsubstituted oxirane. No particular constraints are placed on the identity of the epoxide used in the carbonylation reactions described herein. In certain embodiments, the epoxide is selected from the group consisting of ethylene oxide, propylene oxide, 1,2-butylene oxide, 2,3-butylene oxide, epichlorohydrin, cyclohexene oxide, cyclopentene oxide, 3,3,3-trifluoro-1,2-epoxypropane, styrene oxide, a glycidyl ether, and a glycidyl ester. In certain embodiments, the epoxide is propylene oxide. In certain embodiments, the epoxide is EO. In certain embodiments, the epoxide is prepared from an alkene such as ethylene or propylene.

In some variations, the term "glycidyl", as used herein, refers to an oxirane substituted with a hydroxyl methyl group or a derivative thereof. In other variations, the term glycidyl as used herein is meant to include moieties having additional substitution on one or more of the carbon atoms of the oxirane ring or on the methylene group of the hydroxymethyl moiety, examples of such substitution may include, for example, alkyl groups, halogen atoms, and aryl groups. The terms glycidyl ester, glycidyl acrylate, and glydidyl ether denote substitution at the oxygen atom of the above-mentioned hydroxymethyl group. For example, the oxygen atom is bonded to an acyl group, an acrylate group, or an alkyl group, respectively.

The term "acrylate" or "acrylates" as used herein refer to any acyl group having a vinyl group adjacent to the acyl carbonyl. The terms encompass mono-, di- and tri-substituted vinyl groups. Acrylates may include, for example, acrylate, methacrylate, ethacrylate, cinnamate (3-phenylacrylate), crotonate, tiglate, and senecioate.

As used herein, the terms "crude acrylic acid" and "glacial acrylic acid" (GAA) describe AA of relatively low and high purity, respectively. Crude AA (also called technical grade AA) has a typical minimum overall purity level of 94%, by weight, and can be used to make acrylic esters for paint, adhesive, textile, paper, leather, fiber, and plastic additive applications. GAA has a typical overall purity level ranging from 98% to 99.99% and can be used to make polyacrylic acid (PAA), or a salt thereof, for superabsorbent polymers (SAPs) in disposable diapers, training pants, adult incontinence undergarments and sanitary napkins. PAA, or a salt thereof, is also used in compositions for paper and water treatment, and in detergent co-builder applications. In some variations, acrylic acid has a purity of at least 98%, at least 98.5%, at least 99%, at least 99.1%, at least 99.2%, at least 99.3%, at least 99.4%, at least 99.5%, at least 99.6%, at least 99.7%, at least 99.8%, or at least 99.9%; or between 99% and 99.95%, between 99.5% and 99.95%, between 99.6% and 99.95%, between 99.7% and 99.95%, or between 99.8% and 99.95%.

Suitable salts of PAA include metal salts, such those of any alkali (e.g., Na$^+$, K$^+$) cations, alkaline earth cations. In certain embodiments, the PAA salt is the Na$^+$ salt, i.e., sodium PAA. In certain embodiments, the salt is the K$^+$ salt, i.e., potassium PAA.

Impurities in GAA are reduced to an extent possible to facilitate a high-degree of polymerization to PAA and avoid adverse effects from side products in end applications. For example, aldehyde impurities in AA hinder polymerization and may discolor the PAA. Maleic anhydride impurities form undesirable copolymers which may be detrimental to polymer properties. Carboxylic acids, e.g., saturated carboxylic acids that do not participate in the polymerization, can affect the final odor of PAA or SAP-containing products and/or detract from their use. For example, foul odors may emanate from SAP that contains acetic acid or propionic acid and skin irritation may result from SAP that contains formic acid.

The reduction or removal of impurities from propylene-based AA is costly, whether to produce propylene-based crude AA or propylene-based glacial AA. Such costly multistage distillations and/or extraction and/or crystallizations steps are generally employed (e.g., as described in U.S. Pat. Nos. 5,705,688 and 6,541,665). Notable impurities from propylene-based AA that are reduced and/or eliminated from the disclosed compositions include, for example, aldehyde impurities and products or byproducts of propylene oxidation.

As used herein, the term "product or byproduct of propylene oxidation" or "compound that derives from the oxidation of propylene" are used interchangeably to refer to products and byproducts of propylene oxidation including, for example, $C_1$ compounds such as formaldehyde, and formic acid; $C_2$ compounds such as acetaldehyde, acetic acid; $C_3$ compounds such as propylene, allyl alcohol, acrolein (i.e., propenal), propanol, isopropyl alcohol, acetone, propionic acid; $C_4$ compounds such as maleic anhydride; and $C_5$ compounds such as furfural, etc.

As used herein, the term "aldehyde impurity" include any of the aldehydes in the preceding paragraph.

As used herein, the term "substantially free" means less than 5 wt %, 1 wt %, 0.1 wt %, 0.01 wt %, or a range including any two of these values, or less than 10,000 ppm, 1,000 ppm, 500 ppm, 100 ppm, 50 ppm, 10 ppm, or a range including any two of these values. In one variation, a composition that is substantially free of Compound A has less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.01%, or less than 0.001%, by weight, or a range including any two of the aforementioned values, of Compound A.

Stabilizers are commonly used to preserve AA. As used herein, the term "stabilizer" includes any radical polymerization inhibitor or an anti-foaming agent. AA is susceptible to unwanted Michael addition to itself and to unwanted free-radical polymerization with itself, which may be counteracted by addition of polymerization inhibitors to the AA. Suitable polymerization inhibitors include, for example, hydroquinone monomethyl ether, MEHQ, alkylphenols, such as o-, m- or p-cresol (methylphenol), 2-tert-butyl-4-methylphenol, 6-tert-butyl-2,4-dimethylphenol, 2,6-di-tert-butyl-4-methylphenol, 2-tert-butylphenol, 4-tert-butylphenol, 2,4-di-tert-butylphenol and 2-methyl-4-tert-butylphenol and hydroxyphenols such as hydroquinone, catechol, resorcinol, 2-methylhydroquinone and 2,5-di-tert-butylhydroquinone. Examples of anti-foaming agents include silicones (e.g., polydimethylsiloxanes), alcohols, stearates, and glycols.

As used herein, the term "about" preceding one or more numerical values means the numerical value ±5%. It should be understood that reference to "about" a value or parameter herein includes (and describes) embodiments that are directed to that value or parameter per se. For example, description referring to "about x" includes description of "x" per se.

DETAILED DESCRIPTION

Operators of existing chemical plants that produce a single product are inevitably confronted with a reduction in demand for that product. Generally, they must reduce or suspend production to meet demand. Disclosed herein are chemical plants and production methods that utilize ethylene-derived epoxides for the integrated production of various $C_1$ and/or $C_4$ products that are produced on-site. The disclosed plants are flexible because they may direct epoxide, as needed, to any of the various $C_3$ and/or $C_4$ products. A decrease in production of one product, due to a drop in demand, can be offset by an increase in another product for which demand is strong. Due in part to their versatility, the disclosed chemical plants and production methods provide increased efficiencies relative to existing chemical plants and methods.

Methods

In one aspect, provided are integrated methods for converting epoxides to beta lactones and then to multiple $C_3$ products and/or $C_4$ products.

With reference to FIG. 1, an exemplary process schematic to produce $C_1$ and/or $C_4$ products is depicted. The process depicted involves ethylene oxidation in step 100, carbonylation step 200 to produce BPL, and production of various $C_3$ and/or $C_4$ products in step 300. In step 100, ethylene is fed into an oxidative reactor to produce ethylene oxide by ethylene oxidation. EO outlet stream 110 comprising EO exiting the oxidative reaction zone is fed into a central reactor for the conversion of EO and CO to BPL. In step 200, EO outlet stream 110 comprising EO, from the oxidative reaction zone, enters the central reactor as an inlet stream where it is combined with CO. BPL outlet streams 210 and/or 220 comprising BPL exit the central reactor. BPL outlet streams 210 and/or 220 are fed into the first, second, third and $n^{th}$ $C_3$ and/or $C_4$ reactors. In step 300, BPL outlet streams 210 and/or 220 comprising BPL, from the central reactor, enters each of the first, second, third and $n^{th}$ $C_3$ and/or $C_4$ reactors as an inlet stream where each is converted to first, second, third and $n^{th}$ $C_3$ and/or $C_4$ products. In step 300, first, second, third and $n^{th}$ outlet streams comprising first, second, third and $n^{th}$ $C_3$ and/or $C_4$ products exit the first, second, third and $n^{th}$ $C_3$ and/or $C_4$ reactors. In step 400, the first, second, third and $n^{th}$ outlet streams that exit are purified and/or isolated to produce first, second, third and $n^{th}$ $C_3$ and/or $C_4$ products (depicted in FIG. 1 as "P1", "P2", "P3" and "Pn", respectively).

It should generally be understood that, in other variations of the process described in FIG. 1, one or more steps may be added or omitted. For example, in one variation, step 100 may be omitted, and ethylene oxide obtained from any commercially available source may be fed into the central reactor in step 200.

Thus, in some aspects, provided is a method for converting an epoxide to two or more of: a first $C_3$ product, a second $C_3$ product, and a first $C_4$ product within an integrated system, the method comprising:

i) providing an inlet stream comprising an epoxide and carbon monoxide (CO) to a central reactor of the integrated system;

ii) contacting the inlet stream with a carbonylation catalyst in a central reaction zone to effect conversion of at least a portion of the provided epoxide to a beta lactone;

iii) directing the an outlet stream comprising beta lactone from the central reaction zone to two or more of:

(a) a first $C_3$ reactor, comprising an inlet fed by the outlet stream comprising beta lactone of the central reactor, a first $C_3$ reaction zone that converts at least some of the beta lactone to a first $C_3$ product, and an outlet from which an outlet stream comprising the first $C_3$ product is obtainable, (b) a second $C_3$ reactor, comprising an inlet fed by the outlet stream comprising beta lactone of the central reactor, a second $C_3$ reaction zone that converts at least some of the beta lactone to a second $C_3$ product, and an outlet from which an outlet stream comprising the second $C_3$ product is obtainable, and (c) a first $C_4$ reactor, comprising an inlet fed by the outlet stream comprising beta lactone of the central reactor, a first $C_4$ reaction zone that converts at least some of the beta lactone to a first $C_4$ product, and an outlet from which an outlet stream comprising the first $C_4$ product is obtainable, and iv) obtaining two or more of the first $C_1$ product, the second $C_3$ product, and the first $C_4$ product.

In certain embodiments, the method further comprises:

providing an inlet stream comprising ethylene to an inlet of an oxidative reactor in which at least some of the ethylene is converted to ethylene oxide (EO) and providing an outlet stream comprising EO from the oxidative reactor, to the inlet of the central reactor in which at least some of the EU is converted to beta propiolactone (BPL).

In some variations, the method further comprises:

providing an inlet stream comprising ethylene to an inlet of an oxidative reactor;

converting at least some of the ethylene to ethylene oxide (EO) to produce an outlet stream comprising EO;

directing the outlet stream comprising EU from the oxidative reactor to the inlet of the central reactor; and converting at least some of the EO to BPL.

In certain embodiments, the method further comprises directing the outlet stream comprising beta lactone from the central reaction zone to the first $C_3$ reactor and the second $C_3$ reactor.

In certain embodiments, the method further comprises directing the outlet stream comprising beta lactone from the central reaction zone to the first $C_3$ reactor and the first $C_4$ reactor.

In certain embodiments, the epoxide is ethylene oxide (EO) and the beta lactone is beta propiolactone (BPL).

In certain embodiments, the first $C_3$ product and the second $C_3$ product are independently selected from an α,β-unsaturated acid, an β-unsaturated ester, an α,β-unsaturated amide, a polymer and 1,3-propanediol (PDO).

In certain embodiments, the first $C_3$ product is polypropiolactone (PPL).

In certain embodiments, the first $C_3$ product is acrylic acid.

In certain embodiments, the first $C_3$ product is polyacrylic acid.

In certain embodiments, the first $C_3$ product is an acrylate ester. In certain embodiments, the acrylate ester is selected from methyl acrylate, butyl acrylate and 2-ethylhexyl acrylate.

In certain embodiments, the first $C_3$ product is PDO.

In certain embodiments, the method further comprises:

directing the outlet stream comprising PPL from the first $C_3$ reactor to a third $C_3$ reactor, comprising an inlet fed by the outlet stream comprising PPL of the first $C_3$ reactor, a third $C_3$ reaction zone that converts at least some of the PPL to a third $C_3$ product, and an outlet from which an outlet stream comprising the third $C_3$ product is obtainable.

In some variations, the method further comprises:

directing the outlet stream comprising PPL from the first $C_3$ reactor to a third $C_3$ reactor; and converting at least some of the PPL to a third $C_3$ product in the third $C_3$ reactor to produce an outlet stream comprising the third $C_3$ product.

In certain embodiments, the first $C_3$ product is polypropiolactone (PPL).

In certain embodiments, the third $C_3$ product is acrylic acid.

In certain embodiments, the third $C_3$ product is polyacrylic acid.

In certain embodiments, the first $C_4$ product is succinic anhydride.

In certain embodiments, the first $C_4$ product is succinic anhydride, and the method further comprises a second $C_4$ reactor, comprising an inlet fed by the outlet stream comprising succinic anhydride of the first $C_4$ reactor, a second $C_4$ reaction zone that converts at least some of the succinic anhydride to a second $C_4$ product, and an outlet from which an outlet stream comprising the second $C_4$ product is obtainable.

In some variations where the first $C_4$ product is succinic anhydride, the method further comprises:

directing the outlet stream comprising succinic anhydride from the first $C_4$ reactor to a second $C_4$ reactor; and converting at least some of the succinic anhydride to a second $C_4$ product in the second $C_4$ reactor to produce an outlet stream comprising the second $C_4$ product.

In certain embodiments, the second $C_4$ product is succinic acid, 1,4 butanediol (BDO), tetrahydrofuran (THF) or gamma butyrolactone (GBL).

In one embodiment, provided is an integrated method to produce PPL, AA, and acrylate esters from an epoxide. Thus, in one variation, provided is a method, comprising:

providing an EO stream and a CO stream to a central reactor, wherein the EO stream comprises EO, and the CO stream comprises CO;

contacting the EO stream and the CO stream with a carbonylation catalyst in the central reactor;

converting at least a portion of the EO to produce a beta propiolactone (BPL) stream comprising BPL;

directing at least a portion of the BPL stream to a first C3 reactor;

converting at least portion of the BPL to polypropiolactone (PPL) in the first C3 reactor, to produce a PPL stream comprising the PPL from the first C3 reactor;

directing the PPL stream to a second C3 reactor;

converting at least a portion of the PPL to acrylic acid (AA) in the second C3 reactor, to produce an AA stream comprising the AA from the second C3 reactor;

directing at least a portion of the BPL stream to a third C3 reactor;

contacting the BPL stream in the third C3 reactor with an alcohol; and converting at least a portion of the BPL to acrylate esters in the third C3 reactor, to produce an acrylate ester stream comprising the acrylate esters.

In some variations, the PPL stream, the AA stream, and the acrylate ester stream are simultaneously produced. In certain variations, the method further comprises modulating a ratio of PPL:AA:acrylate ester produced in the PPL stream, the AA stream, and the acrylate ester stream. In yet other variations, the method further comprises modulating the fraction of the PPL stream that is received by the second C3 reactor.

In another embodiment, provided is an integrated method to produce PPL, AA, and acrylate esters from an epoxide. Thus, in another variation, provided is a method, comprising:

providing an EO stream and a CO stream to a central reactor, wherein the EO stream comprises EO, and the CO stream comprises CO;

contacting the EO stream and the CO stream with a carbonylation catalyst in the central reactor;

converting at least a portion of the EO to produce a beta propiolactone (BPL) stream comprising BPL;

directing at least a portion of the BPL stream to a first C3 reactor;

converting at least portion of the BPL to polypropiolactone (PPL) in the first C3 reactor, to produce a PPL stream comprising the PPL from the first C3 reactor;

directing at least a portion of the BPL stream to a second C3 reactor;

converting at least a portion of the BPL to acrylic acid (AA) in the second C3 reactor, to produce an AA stream comprising the AA from the second C3 reactor;

directing at least a portion of the BPL stream to a third C3 reactor;

contacting the BPL stream with an alcohol in the third C3 reactor; and converting at least a portion of the BPL to acrylate esters in the third C3 reactor, to produce an acrylate ester stream comprising the acrylate esters.

In some variations, the PPL stream, the AA stream, and the acrylate ester stream are simultaneously produced. In certain variations, the method further comprises modulating a ratio of PPL:AA:acrylate ester produced in the PPL stream, the AA stream, and the acrylate ester stream. In yet other variations, the method further comprises modulating the fraction of the BPL stream of the first C3 reactor, and wherein the controller modulates the fraction of the BPL stream that is received by the second C3 reactor.

In yet another embodiment, provided is an integrated method to produce PPL, AA, and SA. Thus, in another variation, provided is a method, comprising:

providing an EO stream and a CO stream to a central reactor, wherein the EO stream comprises EO, and the CO stream comprises CO;

contacting the EO stream and the CO stream with a carbonylation catalyst in the central reactor;

converting at least a portion of the EO to produce a beta propiolactone (BPL) stream comprising BPL;

directing at least a portion of the BPL stream to a first C3 reactor;

converting at least portion of the BPL to polypropiolactone (PPL) in the first C3 reactor, to produce a PPL stream comprising the PPL from the first C3 reactor;

directing the PPL stream to a second C3 reactor;

converting at least some of the PPL to acrylic acid (AA) in the second C3 reactor, to produce an AA stream comprising the AA from the second C3 reactor;

directing at least a portion of the BPL stream to a first C4 reactor; and converting at least some of the BPL to succinic anhydride (SA) in the first C4 reactor, to produce a succinic anhydride stream comprising the succinic anhydride from the first C4 reactor.

In some variations, the PPL stream, the AA stream, and the SA stream are simultaneously produced. In certain variations, the method further comprises modulating a ratio of PPL:AA:SA from the PPL stream, the AA stream, and the SA stream. In certain variations, the method further comprises modulating the fraction of the PPL stream that is received by the second C3 reactor. In yet other variations, the method further comprises directing the SA stream to a second C4 reactor; contacting at the SA stream with hydrogen in the second C4 reactor; and converting at least a portion of the SA to 1,4 butanediol (BDO), tetrahydrofuran (THF), or gamma butyrolactone (GBL), or any combinations thereof. In another variation, the method further comprises modulating a ratio of BDO:THF:GBL produced in the second C4 reactor.

In yet another embodiment, provided is an integrated method to produce PPL, AA and acrylate ester. Thus, in yet another variation, provided is a method, comprising:

providing an EO stream and a CO stream to a central reactor, wherein the EO stream comprises EO, and the CO stream comprises CO;

contacting the EO stream and at least a portion of the CO stream with a carbonylation catalyst in the central reactor;

converting at least a portion of the EO to produce a beta propiolactone (BPL) stream comprising BPL;

directing at least a portion of the BPL stream to a first C3 reactor;

converting at least portion of the BPL to polypropiolactone (PPL) in the first C3 reactor, to produce a PPL stream comprising the PPL from the first C3 reactor;

directing at least a portion of the BPL stream to a second C3 reactor;

converting at least a portion of the BPL to acrylic acid (AA) in the second C3 reactor, to produce an AA stream comprising the AA from the second C3 reactor;

directing at least a portion of the BPL stream to a third C3 reactor;

contacting the BPL stream with an alcohol in the third C3 reactor;

converting at least a portion of the BPL to acrylate esters in the C3 reactor, to produce an acrylate ester stream comprising the acrylate esters;

directing at least a portion of the BPL stream to a first C4 reactor;

contacting the BPL stream and at least a portion of the CO stream in the first C4 reactor; and converting at least a portion of the BPL to succinic anhydride (SA) in the first C4 reactor, to produce a SA stream comprising the SA.

In some variations, the PPL stream, the AA stream, and the acrylate ester stream are simultaneously produced. In some variations, the PPL stream, the AA stream, the acrylate ester stream, and the SA stream are simultaneously produced. In certain variations, the method further comprises modulating a ratio PPL:AA:acrylate ester from the PPL stream, the AA stream, and the acrylate ester stream. In other variations, the method further comprises modulating a ratio PPL:AA:acrylate ester output:SA from the PPL stream, the AA stream, the acrylate ester stream, and the SA stream. In one variation, the method further comprises modulating the fraction of the BPL stream that is received by the second C3 reactor.

In some variations that may be combined with the foregoing variations of the methods described herein, the method further includes: directing the SA stream to a second C4 reactor; contacting at the SA stream with hydrogen in the second C4 reactor; and converting at least a portion of the SA to 1,4 butanediol (BDO), tetrahydrofuran (THF), or gamma butyrolactone (GBL), or any combinations thereof. In one variation, the method further comprises modulating a ratio of BDO:THF:GBL produced in the second C4 reactor.

In yet other variations that may be combined with the foregoing variations of the methods described herein, the method further comprises providing an ethylene stream to an oxidative reactor, wherein the ethylene stream comprises ethylene; and converting at least a portion of the ethylene to ethylene oxide (EO), to produce the EO stream.

In yet other variations that may be combined with the foregoing variations of the methods described herein where PPL is produced, the method further comprises isolating PPL from the PPL stream; and packaging the isolated PPL for distribution.

Systems

In one aspect, provided are integrated systems suitable for effecting the conversion of epoxides to multiple $C_3$ products and/or $C_4$ products. In certain embodiments, a system is provided for the production of chemicals, comprising:

a central reactor, comprising an inlet fed by an epoxide source and a carbon monoxide (CO) source, a central reaction zone that converts at least some of the epoxide to a beta lactone, and an outlet which provides an outlet stream comprising the beta lactone, two or more of:

(i) a first $C_3$ reactor, comprising an inlet fed by the outlet stream comprising beta lactone of the central reactor, a first $C_1$ reaction zone that converts at least some of the beta lactone to a first $C_3$ product, and an outlet which provides an outlet stream comprising the first $C_3$ product, (ii) a second $C_3$ reactor, comprising an inlet fed by the outlet stream comprising beta lactone of the central reactor, a second $C_3$ reaction zone that converts at least some of the beta lactone to a second $C_3$ product, and an outlet which provides an outlet stream comprising the second $C_3$ product, and (iii) a first $C_4$ reactor, comprising an inlet fed by the outlet stream comprising beta lactone of the central reactor, a first $C_4$ reaction zone that converts at least some of the beta lactone to a first $C_4$ product, and an outlet which provides an outlet stream comprising the first $C_4$ product, and a controller for independently modulating production of the beta lactone and each of the products, with the provision that the first $C_3$ product differs from the second $C_3$ product.

In some variations, provided is a system for the production of $C_3$ and $C_4$ products, comprising:

an epoxide source;
a carbon monoxide (CO) source;
a central reactor, comprising:
an inlet configured to receive epoxide from the epoxide source and CO from the CO source,
a central reaction zone configured to convert at least some of the epoxide to a beta lactone, and
an outlet configured to provide an outlet stream comprising the beta lactone,
two or more of (i)-(iii):
(i) a first $C_3$ reactor, comprising:
an inlet configured to receive the outlet stream comprising beta lactone of the central reactor,
a first $C_1$ reaction zone configured to convert at least some of the beta lactone to a first $C_3$ product, and
an outlet configured to provide an outlet stream comprising the first $C_3$ product,
(ii) a second $C_3$ reactor, comprising:
an inlet configured to receive the outlet stream comprising beta lactone of the central reactor,
a second $C_3$ reaction zone configured to convert at least some of the beta lactone to a second $C_3$ product, and
an outlet configured to provide an outlet stream comprising the second $C_3$ product, and
(iii) a first $C_4$ reactor, comprising:
an inlet configured to receive the outlet stream comprising beta lactone of the central reactor,
a first $C_4$ reaction zone configured to convert at least some of the beta lactone to a first $C_4$ product, and
an outlet configured to provide an outlet stream comprising the first $C_4$ product, and
a controller to independently modulate production of the beta lactone and each of the products,
provided that the first $C_3$ product differs from the second $C_3$ product.

In certain embodiments, the two or more of (i)-(iii) is (i) the first $C_3$ reactor and (ii) the second $C_3$ reactor. Thus, in certain variations, provided is a system for the production of $C_3$ products, comprising
an epoxide source;
a carbon monoxide (CO) source;
a central reactor, comprising:
an inlet configured to receive epoxide from the epoxide source and CO from the CO source,
a central reaction zone configured to convert at least some of the epoxide to a beta lactone, and an outlet configured to provide an outlet stream comprising the beta lactone,
a first $C_3$ reactor, comprising:
an inlet configured to receive the outlet stream comprising beta lactone of the central reactor,
a first $C_3$ reaction zone configured to convert at least some of the beta lactone to a first $C_3$ product, and
an outlet configured to provide an outlet stream comprising the first $C_3$ product;
a second $C_3$ reactor, comprising:
an inlet configured to receive the outlet stream comprising beta lactone of the central reactor,
a second $C_3$ reaction zone configured to convert at least some of the beta lactone to a second $C_3$ product, and
an outlet configured to provide an outlet stream comprising the second $C_3$ product; and
a controller to independently modulate production of the beta lactone and each of the products,
provided that the first $C_3$ product differs from the second $C_3$ product.

In certain embodiments, the two or more (i)-(iii) is (i) the first $C_3$ reactor and (iii) the first $C_4$ reactor. Thus, in certain variations, provided is a system for the production of $C_3$ and $C_4$ products, comprising:
an epoxide source;
a carbon monoxide (CO) source;
a central reactor, comprising:
an inlet configured to receive epoxide from the epoxide source and CO from the CO source,
a central reaction zone configured to convert at least some of the epoxide to a beta lactone, and
an outlet configured to provide an outlet stream comprising the beta lactone,
a $C_3$ reactor, comprising:
an inlet configured to receive the outlet stream comprising beta lactone of the central reactor,
a $C_3$ reaction zone configured to convert at least some of the beta lactone to a $C_3$ product, and
an outlet configured to provide an outlet stream comprising the $C_3$ product;
a $C_4$ reactor, comprising:
an inlet configured to receive the outlet stream comprising beta lactone of the central reactor,
a $C_4$ reaction zone configured to convert at least some of the beta lactone to a $C_4$ product, and
an outlet configured to provide an outlet stream comprising the $C_4$ product; and
a controller to independently modulate production of the beta lactone and each of the products.

In certain embodiments, the two or more (i)-(iii) is (ii) the second $C_3$ reactor and (iii) the first $C_4$ reactor. Thus, in certain variations, provided is a system for the production of $C_3$ and $C_4$ products, comprising:
an epoxide source;
a carbon monoxide (CO) source;
a central reactor, comprising:
an inlet configured to receive epoxide from the epoxide source and CO from the CO source,
a central reaction zone configured to convert at least some of the epoxide to a beta lactone, and
an outlet configured to provide an outlet stream comprising the beta lactone,
a $C_3$ reactor, comprising:
an inlet configured to receive the outlet stream comprising beta lactone of the central reactor,
a $C_3$ reaction zone configured to convert at least some of the beta lactone to a $C_3$ product, and an outlet configured to provide an outlet stream comprising the $C_3$ product;

a $C_4$ reactor, comprising:

an inlet configured to receive the outlet stream comprising beta lactone of the central reactor, a $C_4$ reaction zone configured to convert at least some of the beta lactone to a $C_4$ product, and an outlet configured to provide an outlet stream comprising the $C_4$ product; and a controller to independently modulate production of the beta lactone and each of the products, In yet other embodiments, the two or more (i)-(iii) is (i) a first $C_3$ reactor, (ii) a second $C_3$ reactor, and (iii) a first $C_4$ reactor. Thus, in other variations, provided is a system for the production of $C_3$ and $C_4$ products, comprising:

an epoxide source;

a carbon monoxide (CO) source;

a central reactor, comprising:

an inlet configured to receive epoxide from the epoxide source and CO from the CO source, a central reaction zone configured to convert at least some of the epoxide to a beta lactone, and an outlet configured to provide an outlet stream comprising the beta lactone, a first $C_3$ reactor, comprising:

an inlet configured to receive the outlet stream comprising beta lactone of the central reactor, a first $C_3$ reaction zone configured to convert at least some of the beta lactone to a first $C_3$ product, and an outlet configured to provide an outlet stream comprising the first $C_3$ product;

a second $C_3$ reactor, comprising:

an inlet configured to receive the outlet stream comprising beta lactone of the central reactor, a second $C_3$ reaction zone configured to convert at least some of the beta lactone to a second $C_3$ product, and an outlet configured to provide an outlet stream comprising the second $C_3$ product;

a first $C_4$ reactor, comprising:

an inlet configured to receive the outlet stream comprising beta lactone of the central reactor, a first $C_4$ reaction zone configured to convert at least some of the beta lactone to a first $C_4$ product, and an outlet configured to provide an outlet stream comprising the first $C_4$ product; and a controller to independently modulate production of the beta lactone and each of the products, provided that the first $C_3$ product differs from the second $C_3$ product.

It should generally be understood that, in other variations, one or more components of the systems described above may be added or omitted. For example, in one variation, the system further comprises:

an ethylene source;

an oxidative reactor comprising:

an inlet configured to receive ethylene, an oxidative reaction zone configured to convert at least some of the ethylene to EO, and an outlet configured to provide an outlet stream comprising the EO, and feed the outlet stream comprising EO to the inlet of the central reactor.

In one variation where the first $C_3$ product is PPL, the system further comprises:

a third $C_3$ reactor comprising:

an inlet configured to receive the outlet stream comprising PPL of the first $C_3$ reactor, a third $C_3$ reaction zone configured to convert at least some of the PPL to a third $C_3$ product, and an outlet configured to provide an outlet stream comprising the third $C_3$ product.

In another variation where the first $C_4$ product is succinic anhydride, the system further comprises:

a second $C_4$ reactor comprising:

an inlet configured to receive the outlet stream comprising succinic anhydride of the first $C_4$ reactor, a second $C_4$ reaction zone configured to convert at least some of the succinic anhydride to a second $C_4$ product, and an outlet configured to provide an outlet stream comprising the second $C_4$ product.

In one variation of the foregoing methods, the epoxide is ethylene oxide (EO) and the beta lactone is beta propiolactone (BPL).

In one embodiment, provided is an integrated system to produce PPL, AA, and acrylate esters from an epoxide. Thus, in one variation, provided is a system, comprising:

an ethylene source;

a carbon monoxide (CO) source;

an alcohol source;

an oxidative reactor comprising:

an inlet configured to receive ethylene from the ethylene source, an oxidative reaction zone configured to convert at least some of the ethylene to ethylene oxide (EO), and an outlet configured to provide an EO stream comprising the EO;

a central reactor comprising:

an inlet configured to receive EO from the EO stream of the oxidative reactor and CO from the CO source, a central reaction zone configured to convert at least some of the EO to beta propiolactone (BPL), and an outlet configured to provide a BPL stream comprising the BPL;

a first C3 reactor comprising:

an inlet configured to receive BPL from at least a portion of the BPL stream of the central reactor, a first C3 reaction zone configured to convert at least some of the BPL to a polypropiolactone (PPL), and an outlet configured to provide a PPL stream comprising the PPL;

a second C3 reactor comprising;

an inlet configured to receive PPL from the PPL stream of the first C3 reactor, a second C3 reaction zone configured to convert at least some of the PPL to AA, and an outlet configured to provide an AA stream comprising the AA;

a third C3 reactor comprising:

an inlet configured to receive BPL from at least a portion of the BPL stream of the central reactor, and an alcohol from the alcohol source, a third C3 reaction zone configured to convert at least some of the BPL to acrylate esters, and an outlet configured to provide an acrylate ester stream comprising the acrylate esters; and a controller to independently modulating production of the EO, BPL, PPL, AA, and acrylate esters.

In some variations, the system is configured to simultaneously produce the PPL stream, the AA stream, and the acrylate ester stream. In certain variations, the controller modulates a ratio of PPL:AA:acrylate ester from the PPL stream, the AA stream, and the acrylate ester stream. In one variation where the inlet of the second C3 reactor is configured to receive PPL from a fraction of the PPL stream of the first C3 reactor, the controller modulates the fraction of the PPL output stream that is received by the inlet of the second C3 reactor.

In another embodiment, provided is an integrated system to produce PPL, AA, and acrylate esters from an epoxide. Thus, in another variation, provided is a system, comprising:
an ethylene source;
a carbon monoxide (CO) source;
an alcohol source;
an oxidative reactor comprising:
an inlet configured to receive ethylene from the ethylene source,
an oxidative reaction zone configured to convert at least some of the ethylene to ethylene oxide (EO), and
an outlet configured to provide an EO stream comprising the EO;
a central reactor comprising:
an inlet configured to receive EU from the EO stream of the oxidative reactor and CO from the CO source,
a central reaction zone configured to convert at least some of the EO to beta propiolactone (BPL), and
an outlet configured to provide a BPL stream comprising the BPL;
a first C3 reactor comprising:
an inlet configured to receive BPL from at least a portion of the BPL stream of the central reactor,
a first C3 reaction zone configured to convert at least some of the BPL to a polypropiolactone (PPL), and
an outlet configured to provide a PPL stream comprising the PPL;
a second C3 reactor comprising;
an inlet configured to receive BPL from at least a portion of the BPL stream of the central reactor,
a second C3 reaction zone configured to convert at least some of the BPL to AA, and
an outlet configured to provide an AA stream comprising the AA;
a third C3 reactor comprising:
an inlet configured to receive BPL from at least a portion of the BPL stream of the central reactor, and an alcohol from the alcohol source,
a third C3 reaction zone configured to convert at least some of the BPL to acrylate esters, and
an outlet configured to provide an acrylate ester stream comprising the acrylate esters; and
a controller to independently modulating production of the EO, BPL, PPL, AA, and acrylate esters.

In one variation, the system is configured to simultaneously produce the PPL stream, the AA stream, and the acrylate ester stream. In certain variations, the controller modulates a ratio of PPL:AA:acrylate ester from the PPL stream, the AA stream, and the acrylate ester stream.

In yet another embodiment, provided is an integrated system to produce PPL, AA, and SA. Thus, in another variation, provided is a system, comprising:
an ethylene source;
a carbon monoxide (CO) source;
an oxidative reactor comprising:
an inlet configured to receive ethylene from the ethylene source,
an oxidative reaction zone configured to convert at least some of the ethylene to ethylene oxide (EO), and
an outlet configured to provide an EO stream comprising the EO;
a central reactor comprising:
an inlet configured to receive EO from the EO stream of the oxidative reactor and CO from the CO source,
a central reaction zone configured to convert at least some of the EO to beta propiolactone (BPL), and
an outlet configured to provide a BPL stream comprising the BPL;
a first C3 reactor comprising:
an inlet configured to receive BPL from at least a portion of the BPL stream of the central reactor,
a first C3 reaction zone configured to convert at least some of the BPL to a polypropiolactone (PPL), and
an outlet configured to provide a PPL stream comprising the PPL;
a second C3 reactor comprising;
an inlet configured to receive PPL from the PPL stream of the first C3 reactor,
a second C3 reaction zone configured to convert at least some of the PPL to AA, and
an outlet configured to provide an AA stream comprising the AA;
a first C4 reactor comprising:
an inlet configured to receive BPL from at least a portion of the BPL stream of the central reactor, and carbon monoxide from the CO source,
a first C4 reaction zone configured to convert at least some of the BPL to succinic anhydride (SA), and
an outlet configured to provide a succinic anhydride stream comprising the succinic anhydride; and
a controller to independently modulating production of the EO, BPL, PPL, AA, and SA.

In some variations, the system is configured to simultaneously produce the PPL stream, the AA stream, and the SA stream. In certain variations, the controller modulates a ratio of PPL:AA:SA from the PPL stream, the AA stream, and the SA stream. In certain variations where the inlet of the second C3 reactor is configured to receive PPL from a fraction of the PPL stream of the first C3 reactor, the controller modulates the fraction of the PPL stream that is received by the inlet of the second C3 reactor.

In some variations of the foregoing system, the system further comprises:
a hydrogen source; and
a second C4 reactor comprising:
an inlet configured to receive SA from the SA stream of the first C4 reactor,
a hydrogen inlet fed from the hydrogen source,
a second C4 reaction zone configured to hydrogenate at least a portion of the SA to provide a C4 product stream comprising 1,4 butanediol (BDO), tetrahydrofuran (THF), or gamma butyrolactone (GBL), or any combinations thereof.

In some variations of the foregoing, the controller is configured to further modulate production of BDO, THF, and GBL.

In yet another embodiment, provided is an integrated system to produce PPL, AA and acrylate ester. Thus, in yet another variation, provided is a system, comprising:
an ethylene source;
a carbon monoxide (CO) source;
an alcohol source;
an oxidative reactor comprising:
an inlet configured to receive ethylene from the ethylene source,
an oxidative reaction zone configured to convert at least some of the ethylene to ethylene oxide (EO), and
an outlet configured to provide an EO stream comprising the EO, a central reactor comprising:
  an inlet configured to receive EO from the EO stream of the oxidative reactor and at least a portion of CO from the CO source,
  a central reaction zone configured to convert at least some of the EO to beta propiolactone (BPL), and
  an outlet configured to provide a BPL stream comprising the BPL;
a first C3 reactor comprising:
  an inlet configured to receive BPL from at least a portion of the BPL stream of the central reactor,
  a first C3 reaction zone configured to convert at least some of the BPL to a polypropiolactone (PPL), and
  an outlet configured to provide a PPL stream comprising the PPL;
a second C3 reactor comprising;
  an inlet configured to receive BPL from the BPL stream of the central reactor,
  a second C3 reaction zone configured to convert at least some of the BPL to AA, and
  an outlet configured to provide an AA stream comprising the AA;
a third C3 reactor comprising:
  an inlet configured to receive BPL from at least a portion of the BPL stream of the central reactor, and an alcohol from the alcohol source,
  a third C3 reaction zone configured to convert at least some of the BPL to acrylate esters, and
  an outlet configured to provide an acrylate ester stream comprising the acrylate esters;
a first C4 reactor comprising:
  an inlet configured to receive BPL from at least a portion of the BPL stream of the central reactor, and at least a portion of CO from the CO source,
  a first C4 reaction zone configured to convert at least some of the BPL to succinic anhydride (SA), and
  an outlet configured to provide a SA stream comprising the succinic anhydride; and
a controller to independently modulating production of the EO, BPL, PPL, AA, acrylate esters, and SA.

In some variations, the system is configured to simultaneously produce the PPL stream, the AA stream, and the acrylate ester stream. In some variations, the system is configured to simultaneously produce the PPL stream, the AA stream, the acrylate ester stream, and the SA stream. In certain variations, the controller modulates a ratio PPL:AA:acrylate ester from the PPL stream, the AA stream, and the acrylate ester stream. In certain variations, the controller modulates a ratio PPL:AA:acrylate ester:SA from the PPL stream, the AA stream, the acrylate ester stream, and the SA stream.

In some variations of the foregoing system, the system further comprises:
a hydrogen source;
a second C4 reactor comprising:
  at least one inlet configured to receive SA from the SA stream of the first C4 reactor, and hydrogen from the hydrogen source,
  a second C4 reaction zone configured to hydrogenate at least a portion of the SA to provide a C4 product stream comprising 1,4 butanediol (BDO), tetrahydrofuran (THF), or gamma butyrolactone (GBL), or any combinations thereof.

In certain variations, the controller is configured to further modulate production of BDO, THF, and GBL.

In some variations of the systems described herein wherein PPL is produced, the system further comprises:
a PPL isolation unit comprising:
  a PPL processing unit,
  a PPL packaging unit, and
  a PPL outlet configured to provide packaged PPL for distribution.

It should generally be understood that reference to "a first reaction zone" and "a second reaction zone", etc. or "a first reactor" and "a second reactor", etc., or "a first stream" and "a second stream", etc., or "a first product" and "a second product", etc., does not necessarily imply an order of the reaction zones, reactors, streams, or products. In some variations, the use of such references denotes the number of reaction zones, reactors, streams, or products present. In other variations, an order may be implied by the context in which the reaction zones, reactors, streams, or products are configured, used or present.

The sections below more fully describe elements of the integrated systems and methods as well as some of the reactions and conditions for effecting the conversion of epoxides to multiple $C_3$ and/or $C_4$ products.

Controller

The controller can be any integrated means (e.g., a computer-based network) to monitor, control and/or modulate (e.g., increase, decrease or maintain) all processes and components related to the disclosed system, including all reaction zones (via sensors, switches, valves, vacuum, pumps etc.). The controller can independently modulate production of the beta lactone by the central reactor, production of the epoxide in an oxidative reactor, if present, and production for each of the products, in their respective reactors, by, e.g., independently controlling temperatures and pressures in each reaction zone and flow rates for inlet and outlet streams.

In some embodiments, the controller is used to increase, decrease or maintain production of the epoxide by the oxidative reactor, and independently increase, decrease or maintain production of the beta lactone by the central reactor, and independently increase, decrease or maintain production of the first $C_3$ product by the first $C_3$ reactor, and independently increase, decrease or maintain production of the second $C_3$ product by the second $C_3$ reactor, and independently increase, decrease or maintain production of the first $C_4$ product by the first $C_4$ reactor, etc. In some embodiments, the controller is used to maintain production of the epoxide and beta lactone, and independently increase and or decrease production of the first $C_3$ product, second $C_3$ product and first $C_4$ product, etc.

Alkene to Epoxide

In certain embodiments, ethylene oxide (EO) is the epoxide. The disclosed system optionally further includes, at its upstream end, an oxidative reactor that produces EO on-site and provides EO to the central reactor. In certain embodiments, EO is obtained directly from the gas phase oxidation of ethylene. This embodiment is advantageous in that it avoids the need to isolate, store, and transport ethylene oxide which is both toxic and explosive. In certain embodiments, the ethylene oxide is maintained in the gas phase as produced and fed to the central reactor without condensing it to a liquid.

Another benefit of producing EO on-site includes a considerable increase in the plant's capacity to produce greater quantities of $C_3$ and/or $C_4$ products. In certain embodiments, the system can produce any combination of $C_3$ and/or $C_4$ products at a rate of about 200, 250, 300, 350, 400, 450, 500, 550, 600, 650, 700, 750, 800, 850, 900, 950, 1,000 kilotons per annum (kta), or within a range including any two of these values.

Thus, in certain embodiments, the system further comprises an oxidative reactor, comprising an inlet fed by ethylene, an oxidative reaction zone that converts at least some of the ethylene to EO, and an outlet which provides an outlet stream comprising the EO, which is fed to the inlet of the central reactor.

Alternatively, in other embodiments, EO is not produced within the disclosed system. Rather, in such embodiments, an upstream oxidative reactor is absent and the central reactor is fed EO that was produced off-site.

Epoxide to Lactone

In certain embodiments, the disclosed system includes a central reactor for carbonylation of an epoxide into beta lactone via a "carbonylation reaction." The central reactor receives a gaseous mixture containing the epoxide (e.g., from the epoxide source) and CO (e.g., from the CO source), as well as the carbonylation catalyst and solvents, etc. and carries out the carbonylation reaction of the epoxide in the central reaction zone. In certain embodiments, the epoxide is EO and the beta lactone is BPL. In certain embodiments, the carbonylation reaction is continuous. Such continuous carbonylation reactions can be conducted in a continuous stirred tank reactor or a plug flow reactor such that BPL solution is withdrawn at essentially the same rate it is formed.

In certain embodiments, the carbonylation reaction proceeds as shown below where the epoxide is EO and the carbonylation product is BPL:

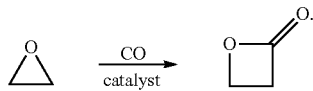

In certain embodiments, the carbonylation reaction proceeds as shown below where the epoxide is propylene oxide and the carbonylation product is beta butyrolactone:

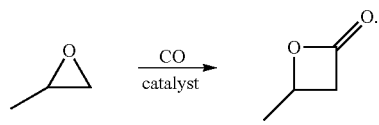

In certain embodiments, the carbonylation reaction proceeds as shown below:

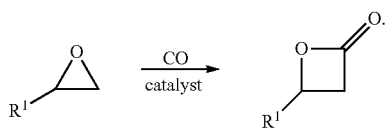

where, $R^1$ is selected from the group consisting of —H and $C_{1-6}$ aliphatic.

Carbonylation Reaction Conditions

Methods of making BPL are known in the art and include those described in WO2013/063191 and WO2014/004858. Suitable catalysts and reaction conditions for effecting the above reactions are described herein and also disclosed in published PCT applications: WO2003/050154, WO2004/089923, WO2012/158573, WO2010/118128, WO2013/063191, and WO2014/008232; in U.S. Pat. Nos. 5,359,081 and 5,310,948 and in the publication "Synthesis of beta-Lactones" J. AM. CHEM. SOC., vol. 124, 2002, pages 1174-1175.

In certain embodiments, the central reactor, comprising an inlet, is fed by a "reaction stream" comprising the epoxide and carbon monoxide (CO). In certain embodiments, the reaction stream fed into the carbonylation reaction comprises a gaseous mixture containing epoxide and CO. In certain embodiments, the molar ratio of CO to epoxide in the reaction stream ranges from about 1:1 to about 10,000:1. In certain embodiments, the molar ratio of CO to epoxide in the reaction stream is about 5000:1, is about 2500:1, is about 2000:1, is about 1500:1, is about 1000:1, is about 500:1, is about 1:500, is about 200:1, is about 100:1, is about 50:1, is about 20:1, is about 10:1, is about 5:1 or is about 1:1, or within a range including any two of these ratios.

In certain embodiments, the reaction stream further comprises one or more additional components. In certain embodiments, the additional components comprise diluents which do not directly participate in the chemical reactions of the epoxide or its derivatives. In certain embodiments, such diluents may include one or more inert gases (e.g., nitrogen, argon, helium and the like) or volatile organic molecules such as hydrocarbons, ethers, and the like. In certain embodiments, the reaction stream may comprise hydrogen, traces of carbon dioxide, methane, and other compounds commonly found in industrial CO streams. In certain embodiments, the feed stream may further comprise materials that may have a direct or indirect chemical function in one or more of the processes involved in the conversion of the epoxide to various end products. Additional reactants can also include mixtures of CO and another gas. For example, as noted above, In certain embodiments, CO is provided in a mixture with hydrogen (e.g., Syngas).

In certain embodiments, the reaction stream is characterized in that it is essentially free of oxygen. In certain embodiments, the reaction stream is characterized in that it is essentially free of water. In certain embodiments, the reaction stream is characterized in that it is essentially free of oxygen and water.

Carbonylation Solvents

In certain embodiments, the carbonylation reaction described herein is performed in a solvent. In certain embodiments, the solvent is fed to the central reaction zone as a separate stream. In other embodiments, the solvent may be fed to the central reaction zone along with the catalyst, the epoxide or another feed stream entering the carbonylation reaction in the central reaction zone. In certain embodiments, the solvent enters the central reaction zone along with the carbonylation catalyst which is provided as a catalyst solution in the solvent. In certain embodiments, the solvent enters the central reaction zone in two or more separate feed streams. In embodiments where solvent is present in the central reaction zone, it is also present in the carbonylation outlet stream.

The solvent may be selected from any solvent, and mixtures of solvents. Additionally, beta lactone may be utilized as a co-solvent. Solvents most suitable for the methods include ethers, hydrocarbons and non protic polar solvents. Examples of suitable solvents include, for example, tetrahydrofuran ("THF"), sulfolane, N-methyl pyrrolidone, 1,3 dimethyl-2-imidazolidinone, diglyme, triglyme, tetraglyme, diethylene glycol dibutyl ether, isosorbide ethers, methyl tertbutyl ether, diethylether, diphenyl ether, 1,4-dioxane, ethylene carbonate, propylene carbonate, butylene carbonate, dibasic esters, diethyl ether, acetonitrile, ethyl acetate, dimethoxy ethane, acetone, and methylethyl ketone.

In certain embodiments, the carbonylation reaction further includes a Lewis base additive to the carbonylation reaction in the central reaction zone. In some embodiments such Lewis base additives can stabilize or reduce deactivation of the catalysts. In certain embodiments, the Lewis base additive is selected from the group consisting of phosphines, amines, guanidines, amidines, and nitrogen-containing heterocycles. In certain embodiments, the Lewis base additive is a hindered amine base. In certain embodiments, the Lewis base additive is a 2,6-lutidine; imidazole, 1-methylimidazole, 4-dimethylaminopyridine, trihexylamine or triphenylphosphine.

Carbonylation Catalyst

Numerous carbonylation catalysts known in the art are suitable for (or can be adapted to) methods described herein. For example, in some embodiments, the carbonylation methods utilize a metal carbonyl-Lewis acid catalyst such as those described in U.S. Pat. No. 6,852,865. In other embodiments, the carbonylation is performed with one or more of the carbonylation catalysts disclosed in U.S. patent application Ser. Nos. 10/820,958; and 10/586,826. In other embodiments, the carbonylation is performed with one or more of the catalysts disclosed in U.S. Pat. Nos. 5,310,948; 7,420,064; and 5,359,081. Additional catalysts for the carbonylation of epoxides are discussed in a review in Chem. Commun., 2007, 657-674.

In some embodiments, the carbonylation catalyst includes a metal carbonyl compound. Typically, a single metal carbonyl compound is provided, but in some embodiments, mixtures of two or more metal carbonyl compounds are provided. Thus, when a provided metal carbonyl compound "comprises", e.g., a neutral metal carbonyl compound, it is understood that the provided metal carbonyl compound can be a single neutral metal carbonyl compound, or a neutral metal carbonyl compound in combination with one or more metal carbonyl compounds. Preferably, the provided metal carbonyl compound is capable of ring-opening an epoxide and facilitating the insertion of CO into the resulting metal carbon bond. Metal carbonyl compounds with this reactivity are well known in the art and are used for laboratory experimentation as well as in industrial processes such as hydroformylation.

In some embodiments, a provided metal carbonyl compound comprises an anionic metal carbonyl moiety. In other embodiments, a provided metal carbonyl compound comprises a neutral metal carbonyl compound. In some embodiments, a provided metal carbonyl compound comprises a metal carbonyl hydride or a hydrido metal carbonyl compound. In some embodiments, a provided metal carbonyl compound acts as a pre-catalyst which reacts in situ with one or more reaction components to provide an active species different from the compound initially provided. Such pre-catalysts are specifically encompassed as it is recognized that the active species in a given reaction may not be known with certainty; thus the identification of such a reactive species in situ does not itself depart from the spirit or teachings herein.

In certain embodiments, the hydrido metal carbonyl (either as provided or generated in situ) comprises one or more of $HCo(CO)_4$, $HCoQ(CO)_3$, $HMn(CO)_5$, $HMn(CO)_4Q$, $HW(CO)_3Q$, $HRc(CO)_5$, $HMo(CO)_3Q$, $HOs(CO)_2Q$, $HMo(CO)_2Q_2$, $HFe(CO)_2Q$, $HW(CO)_2Q_2$, $HRuCOQ_2$, $H_2Fe(CO)_4$ or $H_2Ru(CO)_4$, where each Q is independently as defined above and in the classes and subclasses herein. In certain embodiments, the metal carbonyl hydride (either as provided or generated in situ) comprises $HCo(CO)_4$. In certain embodiments, the metal carbonyl hydride (either as provided or generated in situ) comprises $HCo(CO)_3PR_3$, where each R is independently an optionally substituted aryl group, an optionally substituted $C_{1-20}$ aliphatic group, an optionally substituted $C_{1-10}$ alkoxy group, or an optionally substituted phenoxy group. In certain embodiments, the metal carbonyl hydride (either as provided or generated in situ) comprises $HCo(CO)_3cp$, where cp represents an optionally substituted pentadienyl ligand. In certain embodiments, the metal carbonyl hydride (either as provided or generated in situ) comprises $HMn(CO)_5$. In certain embodiments, the metal carbonyl hydride (either as provided or generated in situ) comprises $H_2Fe(CO)_4$.

In some embodiments, the metal carbonyl compound comprises an anionic metal carbonyl species. In some embodiments, such anionic metal carbonyl species have the general formula $[Q_dM'_e(CO)_w]^{y-}$, where Q is any ligand and need not be present, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. In some embodiments, the anionic metal carbonyl has the general formula $[QM'(CO)_w]^{y-}$, where Q is any ligand and need not be present, M' is a metal atom, w is a number such as to provide the stable anionic metal carbonyl, and y is the charge of the anionic metal carbonyl.

In some embodiments, the anionic metal carbonyl species include monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, for example, $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2}$, $[Tc(CO)_5]^-$, $[Re(CO)_5]^-$, and $[Mn(CO)_5]$. In some embodiments, the anionic metal carbonyl comprises $[Co(CO)_4]^-$. In some embodiments, a mixture of two or more anionic metal carbonyl complexes may be present in the carbonylation catalysts used in the methods.

The term "such as to provide a stable anionic metal carbonyl" for $[Q_dM'_e(CO)_w]^{y-}$ is used herein to mean that $[Q_dM'_e(CO)_w]^{y-}$ is a species that may be characterized by analytical means, e.g., NMR, IR, X-ray crystallography, Raman spectroscopy and/or electron spin resonance (EPR) and isolable in catalyst form in the presence of a suitable cation or a species formed in situ. It is to be understood that metals which can form stable metal carbonyl complexes have known coordinative capacities and propensities to form polynuclear complexes which, together with the number and character of optional ligands Q that may be present and the charge on the complex will determine the number of sites available for CO to coordinate and therefore the value of w. Typically, such compounds conform to the "18-electron rule". Such knowledge is within the grasp of one having ordinary skill in the arts pertaining to the synthesis and characterization of metal carbonyl compounds.

In embodiments where the provided metal carbonyl compound is an anionic species, one or more cations must also necessarily be present. The present disclosure places no particular constraints on the identity of such cations. In some embodiments, the cation associated with an anionic metal carbonyl compound comprises a reaction component of another category described herein. For example, in some embodiments, the metal carbonyl anion is associated with a cationic Lewis acid. In other embodiments a cation associated with a provided anionic metal carbonyl compound is a simple metal cation such as those from Groups 1 or 2 of the periodic table (e.g., $Na^+$, $Li^+$, $K^+$, and $Mg^{2+}$). In other embodiments a cation associated with a provided anionic metal carbonyl compound is a bulky non electrophilic cation such as an 'onium salt' (e.g., $Bu_4N^+$, $PPN^+$, $Ph_4P^+$, and $Ph_4As^+$). In other embodiments, a metal carbonyl anion is associated with a protonated nitrogen compound (e.g., a cation may comprise a compound such as $MeTBD-H^+$, $DMAP-H^+$, $DABCO-H^+$, and $DBU-H^+$). In some embodiments, compounds comprising such protonated nitrogen compounds are provided as the reaction product between an acidic hydrido metal carbonyl compound and a basic nitrogen-containing compound (e.g., a mixture of DBU and $HCo(CO)_4$).

In some embodiments, a catalyst utilized in the methods described herein comprises a neutral metal carbonyl compound. In some embodiments, such neutral metal carbonyl compounds have the general formula $Q_dM'_e(CO)_{w'}$, where Q is any ligand and need not be present, M' is a metal atom, d is an integer between 0 and 8 inclusive, e is an integer between 1 and 6 inclusive, and w' is a number such as to provide the stable neutral metal carbonyl complex. In some embodiments, the neutral metal carbonyl has the general formula $QM'(CO)_{w'}$. In some embodiments, the neutral metal carbonyl has the general formula $M'(CO)_{w'}$. In some embodiments, the neutral metal carbonyl has the general formula $QM'_2(CO)_{w'}$. In some embodiments, the neutral metal carbonyl has the general formula $M'_2(CO)_{w'}$. Suitable neutral metal carbonyl compounds include, for example, $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5$, $Ru_3(CO)_{12}$, $Os_3(CO)_{12}Fe_3(CO)_{12}$, $Fe_2(CO)_9$, $Co_4(CO)_2$, $Rh_4(CO)_2$, $Rh_6(CO)_{16}$, $Ir_4(CO)_{12}$, $Co_2(CO)_8$, and $Ni(CO)_4$.

The term "such as to provide a stable neutral metal carbonyl" for $Q_dM'_e(CO)_{w'}$ is used herein to mean that $Q_dM'_e(CO)_{w'}$ is a species that may be characterized by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for CO to coordinate and therefore the value of w'. Typically, such compounds conform to stoichiometries conforming to the "18-electron rule". Such knowledge is within the grasp of one having ordinary skill in the arts pertaining to the synthesis and characterization of metal carbonyl compounds.

In some embodiments, no ligands Q are present on the metal carbonyl compound. In other embodiments, one or more ligands Q are present on the metal carbonyl compound. In some embodiments, where Q is present, each occurrence of Q is selected from the group consisting of phosphine ligands, amine ligands, cyclopentadienyl ligands, heterocyclic ligands, nitriles, phenols, and combinations of two or more of these. In some embodiments, one or more of the CO ligands of any of the metal carbonyl compounds described above is replaced with a ligand Q. In some embodiments, Q is a phosphine ligand. In some embodiments, Q is a triaryl phosphine. In some embodiments, Q is trialkyl phosphine.

In some embodiments, Q is a phosphite ligand. In some embodiments, Q is an optionally substituted cyclopentadienyl ligand. In some embodiments, Q is cp. In some embodiments, Q is cp*. In some embodiments, Q is an amine or a heterocycle.

In some embodiments, the carbonylation catalyst utilized in the methods described above further includes a Lewis acidic component. In some embodiments, the carbonylation catalyst includes an anionic metal carbonyl complex and a cationic Lewis acidic component. In some embodiments, the metal carbonyl complex includes a carbonyl cobaltate and the Lewis acidic co-catalyst includes a metal-centered cationic Lewis acid. In some embodiments, an included Lewis acid comprises a boron compound.

In certain embodiments, for any of the metal carbonyl compounds described above, M' comprises a transition metal. In certain embodiments, for any of the metal carbonyl compounds described above, M' is selected from Groups 5 (Ti) to 10 (Ni) of the periodic table. In certain embodiments, M' is a Group 9 metal. In certain embodiments, M' is Co. In certain embodiments, M' is Rh. In certain embodiments, M' is Ir. In certain embodiments, M' is Fe. In certain embodiments, M' is Mn.

In some embodiments, where an included Lewis acid comprises a boron compound, the boron compound comprises a trialkyl boron compound or a triaryl boron compound. In some embodiments, an included boron compound comprises one or more boron-halogen bonds. In some embodiments, where an included boron compound comprises one or more boron-halogen bonds, the compound is a dialkyl halo boron compound (e.g., $R_2BX$), a dihalo monoalkyl compound (e.g., $RBX_2$), an aryl halo boron compound (e.g., $Ar_2BX$ or $ArBX_2$), or a trihalo boron compound (e.g., $BCl_3$ or $BBr_3$), wherein each R is an alkyl group; each X is a halogen; and each Ar is an aromatic group.

In some embodiments, where the included Lewis acid comprises a metal-centered cationic Lewis acid, the Lewis acid is a cationic metal complex. In some embodiments, the cationic metal complex has its charge balanced either in part, or wholly by one or more anionic metal carbonyl moieties. Suitable anionic metal carbonyl compounds include those described above. In some embodiments, there are 1 to 17 such anionic metal carbonyls balancing the charge of the metal complex. In some embodiments, there are 1 to 9 such anionic metal carbonyls balancing the charge of the metal complex. In some embodiments, there are 1 to 5 such anionic metal carbonyls balancing the charge of the metal complex. In some embodiments, there are 1 to 3 such anionic metal carbonyls balancing the charge of the metal complex.

In some embodiments, where carbonylation catalysts used in methods described herein include a cationic metal complex, the metal complex has the formula $[(L^c)_vM_b]^{z+}$, wherein:

$L^c$ is a ligand where, when two or more $L^c$ are present, each may be the same or different;

M is a metal atom where, when two M are present, each may be the same or different;

v is an integer from 1 to 4 inclusive;

b is an integer from 1 to 2 inclusive; and z is an integer greater than 0 that represents the cationic charge on the metal complex.

In some embodiments, provided Lewis acids conform to structure I:

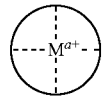
I wherein:

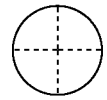

is a multidentate ligand;
M is a metal atom coordinated to the multidentate ligand; and
a is the charge of the metal atom and ranges from 0 to 2.

In some embodiments, provided metal complexes conform to structure II:

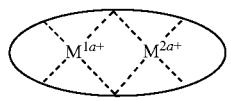
II wherein a is as defined above (each a may be the same or different), and
$M^1$ is a first metal atom;
$M^2$ is a second metal atom;

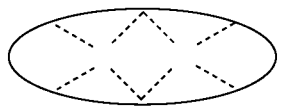

comprises a multidentate ligand system capable of coordinating both metal atoms.

For sake of clarity, and to avoid confusion between the net and total charge of the metal atoms in complexes I and II and other structures herein, the charge ($a^+$) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net charge of +1, and a would be 1.

Suitable multidentate ligands include, for example, porphyrin derivatives 1, salen ligands 2, dibenzotetramethyltetraaza[14]annulene (tmtaa) ligands 3, phthalocyaninate ligands 4, the Trost ligand 5, tetraphenylporphyrin ligands 6, and corrole ligands 7. In some embodiments, the multidentate ligand is a salen ligand. In other embodiments, the multidentate ligand is a porphyrin ligand. In other embodiments, the multidentate ligand is a tetraphenylporphyrin ligand. In other embodiments, the multidentate ligand is a corrole ligand. Any of the foregoing ligands can be unsubstituted or can be substituted. Numerous variously substituted analogs of these ligands are known in the art and will be apparent to the skilled artisan.

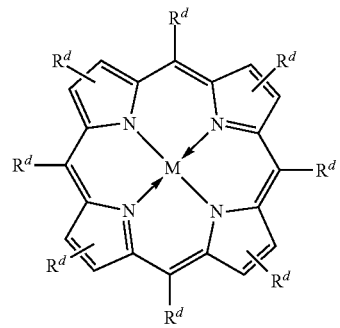
1

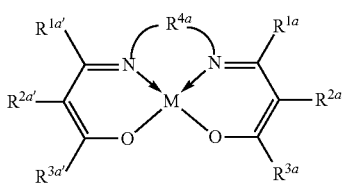
2

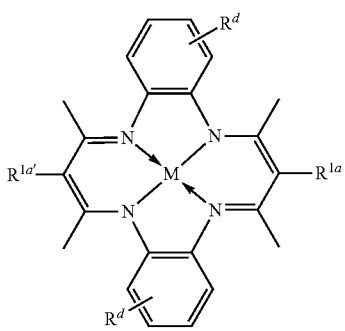
3

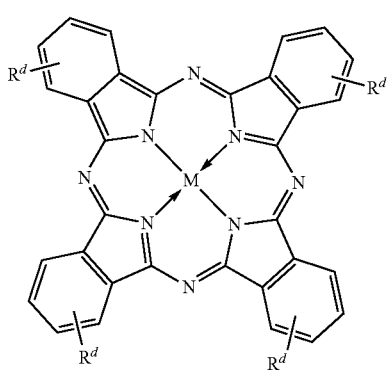
4

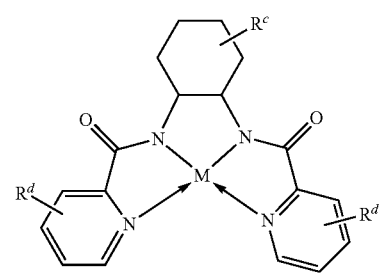
5

-continued

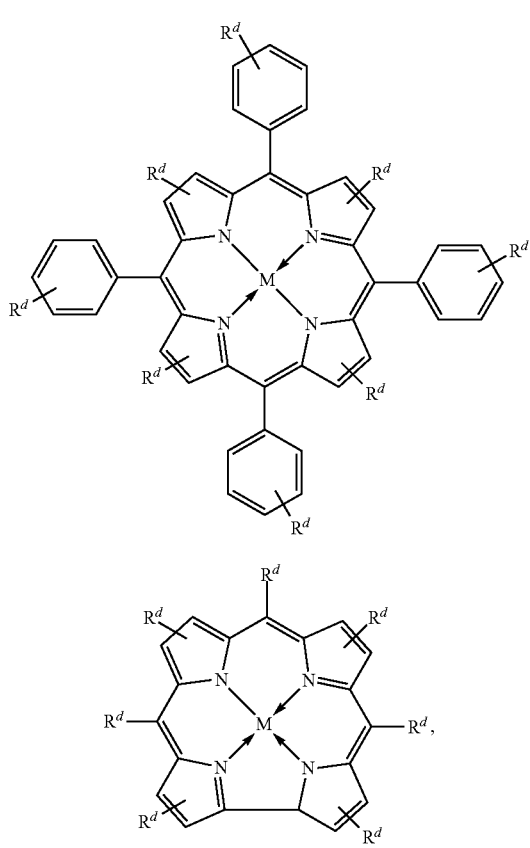

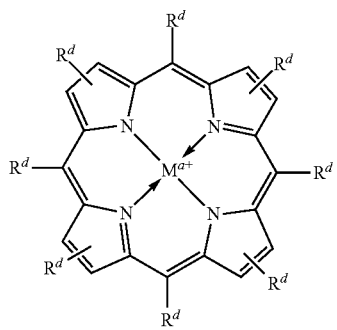

wherein each of $R^c$, $R^d$, $R^{1a}$, $R^{2a}$, $R^{3a}$, $R^{4a}$, $R^{1a'}$, $R^{2a'}$, $R^{3a'}$, and M, is as defined and described in the classes and subclasses herein.

In some embodiments, Lewis acids provided carbonylation catalysts used in methods described herein comprise metal-porphinato complexes. In some embodiments, the moiety

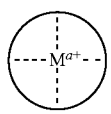

has the structure:

wherein:
each of M and a is as defined above and described in the classes and subclasses herein, and $R^d$ at each occurrence is independently hydrogen, halogen, —$OR^4$, —$NR^y{}_2$, —$SR^y$, —CN, —$NO_2$, —$SO_2R^u$, —$SOR^y$, —$SO_2NR^y{}_2$; —CNO, —$NR^ySO_2R^y$, —NCO, —$N_3$, —$SiR^y{}_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur, where two or more $R^d$ groups may be taken together to form one or more optionally substituted rings;

each $R^y$ is independently hydrogen, an optionally substituted group selected the group consisting of acyl; carbamoyl, arylalkyl; 6- to 10-membered aryl; $C_{1-12}$ aliphatic; $C_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each $R^4$ is independently is a hydroxyl protecting group or R.

In some embodiments, the moiety

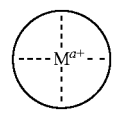

has the structure:

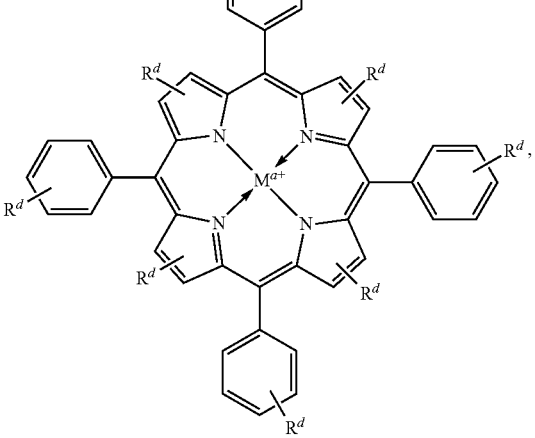

where M, a and $R^d$ are as defined above and in the classes and subclasses herein.

In some embodiments, the moiety

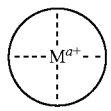

has the structure:

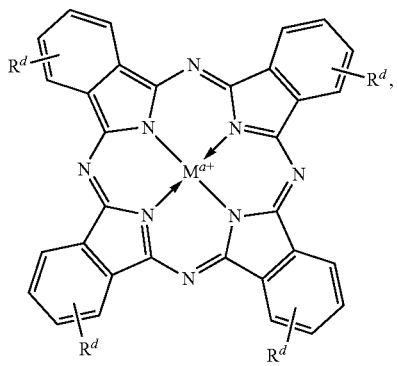

where M, a and $R^d$ are as defined above and in the classes and subclasses herein.

In some embodiments, Lewis acids included in carbonylation catalysts used in methods described herein comprise metallo salenate complexes. In some embodiments, the moiety

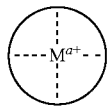

has the structure:

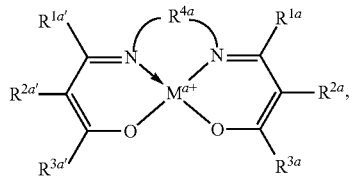

wherein:
M, and a are as defined above and in the classes and subclasses herein.
$R_{1a}$, $R^{1a'}$, $R^{2a}$, $R^{2a'}$, $R^{3a}$, and $R^{3a'}$ are independently hydrogen, halogen, —$OR^4$, —$NR^y_2$, —$SR^y$, —CN, —$SO_2R^y$, —$SOR^y$, —$SO_2NR^y_2$; —CNO, —$NR^ySO_2R^y$, —NCO, —$N_3$, —$SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;
wherein each $R^4$, and $R^y$ is independently as defined above and described in classes and subclasses herein, wherein any of ($R^{2a'}$ and $R^{3a'}$), ($R^{2a}$ and $R^{3a}$), ($R^{1a}$ and $R^{2a}$), and ($R^{1a'}$ and $R^{2a'}$) may optionally be taken together with the carbon atoms to which they are attached to form one or more rings which may in turn be substituted with one or more $R^y$ groups; and $R^{4a}$ is selected from the group consisting of:

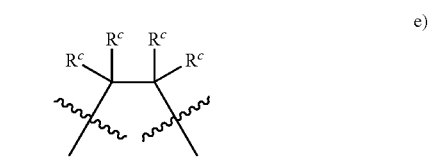

e)

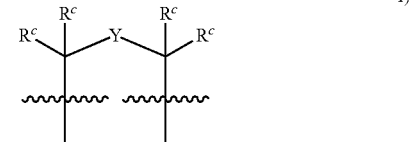

f)

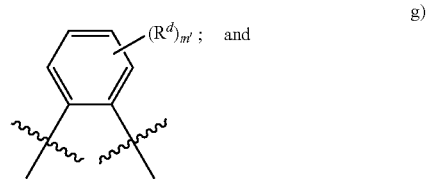

g)

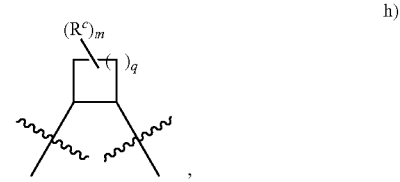

h)

where
$R^c$ at each occurrence is independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, —$SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;

where:
two or more $R^c$ groups may be taken together with the carbon atoms to which they are attached and any intervening atoms to form one or more rings;
when two $R^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;
where $R^4$ and $R^y$ are as defined above and in classes and subclasses herein;

Y is a divalent linker selected from the group consisting of: —NR^y—, —N(R^y)C(O)—, —C(O)NR^y—, —O—, —C(O)—, —OC(O)—, —C(O)O—, —S—, —SO—, —SO_2—, —C(=S) —C(=NR^y)—, —N=N—; a polyether; a $C_3$ to $C_8$ substituted or unsubstituted carbocycle; and a $C_1$ to $C_8$ substituted or unsubstituted heterocycle;

m' is 0 or an integer from 1 to 4, inclusive;

q is 0 or an integer from 1 to 4, inclusive; and x is 0, 1, or 2.

In some embodiments, a provided Lewis acid comprises a metallo salen compound, as shown in formula Ia:

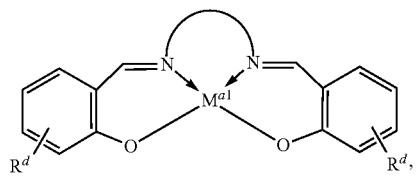

wherein each of M, $R^d$, and a, is as defined above and in the classes and subclasses herein,

represents is an optionally substituted moiety linking the two nitrogen atoms of the diamine portion of the salen ligand, where

is selected from the group consisting of a $C_3$-$C_{14}$ carbocycle, a $C_6$-$C_{10}$ aryl group, a $C_3$-$C_{14}$ heterocycle, and a $C_5$-$C_{10}$ heteroaryl group; or an optionally substituted $C_2$-$C_{20}$ aliphatic group, wherein one or more methylene units are optionally and independently replaced by —NR^u—, —N(R^y)C(O)—, —C(O)N(R^y)—, —OC(O)N(R^y)—, —N(R^y)C(O)O—, —OC(O)O—, —O—, —C(O)—, —OC(O)—, —C(O)O—, —S—, —SO—, —SO_2—, —C(=S)—, —C(=NR^y)—, —C(=NOR^y)— or —N=N—.

In some embodiments metal complexes having formula Ia above, at least one of the phenyl rings comprising the salicylaldehyde-derived portion of the metal complex is independently selected from the group consisting of:

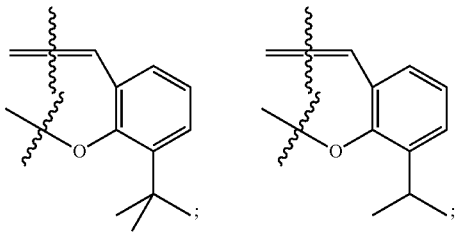

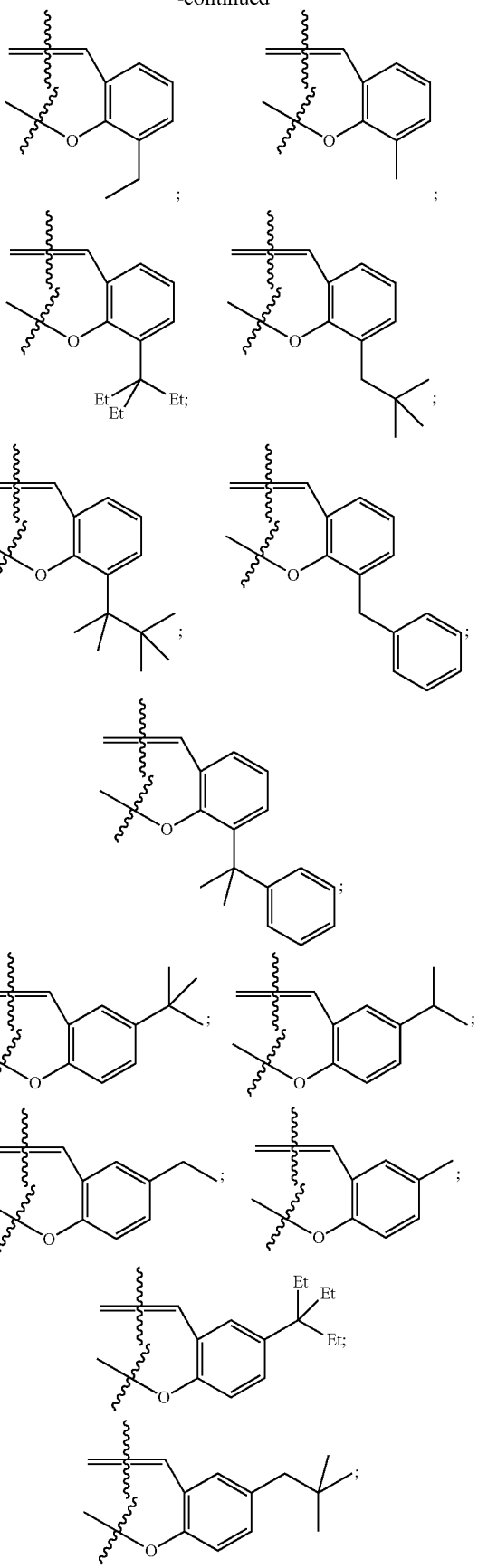

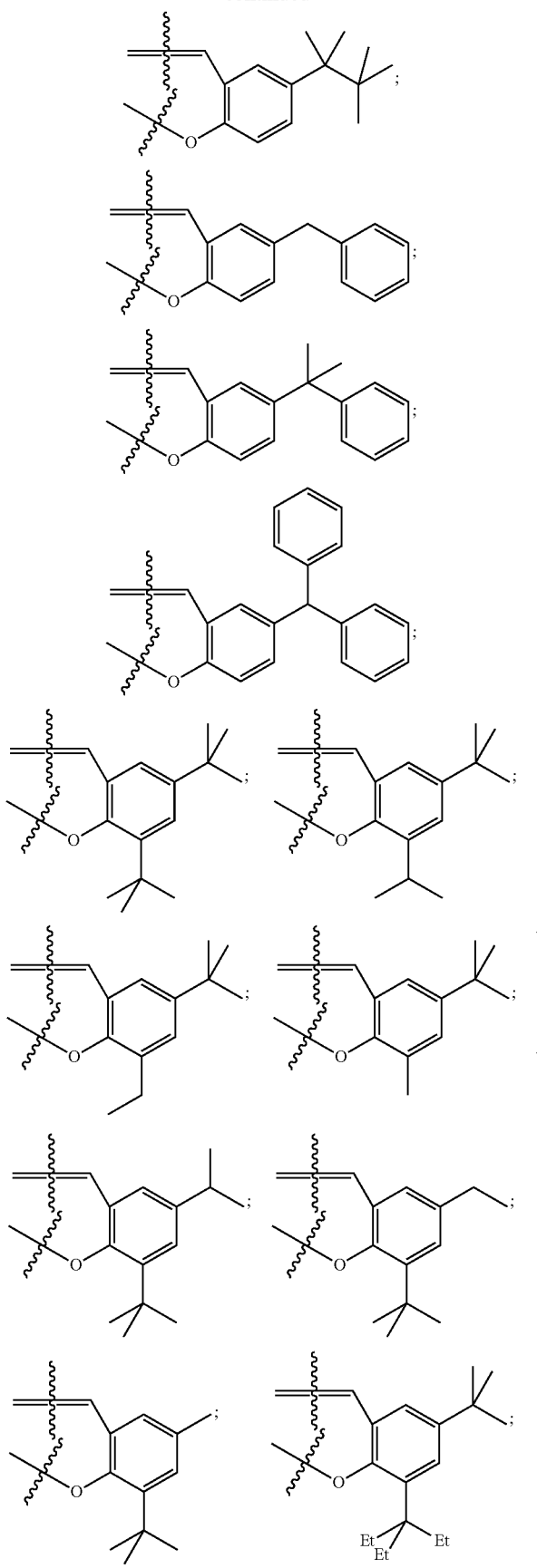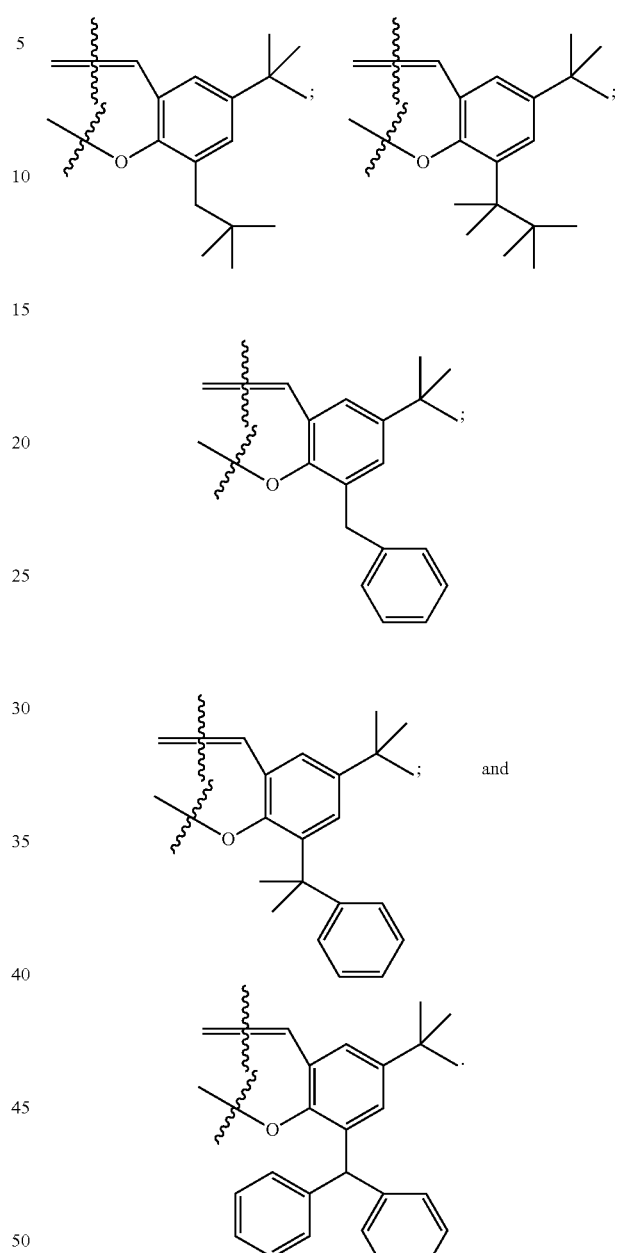
In some embodiments, a provided Lewis acid comprises a metallo salen compound, conforming to one of formulae Va or Vb:
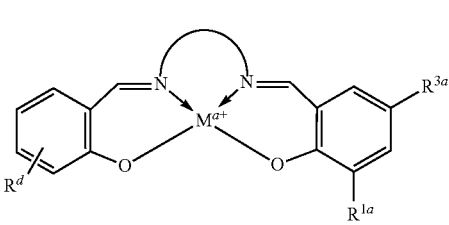
or -continued

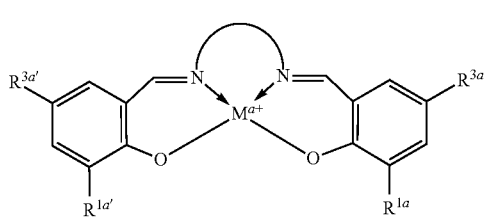
Vb where M, a, $R^d$, $R^{1a}$, $R^{3a}$, $R^{1a'}$, $R^{3a'}$, and

are as defined above and in the classes and subclasses herein.

In some embodiments of metal complexes having formulae Va or Vb, each $R^{1a}$ and $R^{3a}$ is, independently, optionally substituted $C_1$-$C_{20}$ aliphatic.

In some embodiments, the moiety

comprises an optionally substituted 1,2-phenyl moiety.

In some embodiments, Lewis acids included in carbonylation catalysts used in methods described herein comprise metal-tmtaa complexes. In some embodiments, the moiety

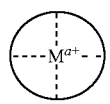

has the structure:

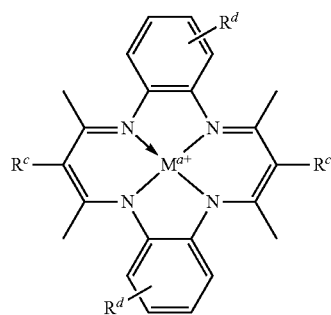

where M, a and $R^d$ are as defined above and in the classes and subclasses herein, and $R^e$ at each occurrence is independently hydrogen, halogen, —OR, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, —$SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur.

In some embodiments, the moiety

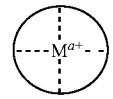

has the structure:

where each of M, a, $R^c$ and $R^d$ is as defined above and in the classes and subclasses herein.

In some embodiments, where carbonylation catalysts used in methods described herein include a Lewis acidic metal complex, the metal atom is selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium.

In some embodiments, M has an oxidation state of +2. In some embodiments, M is Zn(II), Cu(II), Mn(II), Co(II), Ru(II), Fe(II), Co(II), Rh(II), Ni(II), Pd(II) or Mg(II). In some embodiments M is Zn(II). In some embodiments M is Cu(II).

In some embodiments, M has an oxidation state of +3. In some embodiments, M is Al(III), Cr(III), Fe(III), Co(III), Ti(III) In(III), Ga(III) or Mn(III). In some embodiments M is Al(III). In some embodiments M is Cr(III).

In some embodiments, M has an oxidation state of +4. In some embodiments, M is Ti(IV) or Cr(IV).

In some embodiments, $M^1$ and $M^2$ are each independently a metal atom selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium. In some embodiments, $M^1$ and $M^2$ are the same. In some embodiments, $M^1$ and $M^2$ are the same metal, but have different oxidation states. In some embodiments, $M^1$ and $M^2$ are different metals.

In some embodiments, one or more of $M^1$ and $M^2$ has an oxidation state of +2. In some embodiments, $M^1$ is Zn(II), Cu(II), Mn(II), Co(II), Ru(II), Fe(II), Co(II), Rh(II), Ni(II), Pd(II) or Mg(II). In some embodiments $M^1$ is Zn(II). In some embodiments $M^1$ is Cu(II). In some embodiments, $M^2$ is Zn(II), Cu(II), Mn(II), Co(II), Ru(II), Fe(II), Co(II), Rh(II), Ni(II), Pd(II) or Mg(II). In some embodiments $M^2$ is Zn(II). In some embodiments $M^2$ is Cu(II).

In some embodiments, one or more of $M^1$ and $M^2$ has an oxidation state of +3. In some embodiments, $M^1$ is Al(III), Cr(III), Fe(III), Co(III), Ti(III) In(III), Ga(III) or Mn(III). In some embodiments $M^1$ is Al(III). In some embodiments $M^1$ is Cr(III). In some embodiments, $M^2$ is Al(III), Cr(III), Fe(III), Co(III), Ti(III) In(III), Ga(III) or Mn(III). In some embodiments $M^2$ is Al(III). In some embodiments $M^2$ is Cr(III).

In some embodiments, one or more of $M^1$ and $M^2$ has an oxidation state of +4. In some embodiments, $M^1$ is Ti(IV) or Cr(IV). In some embodiments, $M^2$ is Ti(IV) or Cr(IV).

In some embodiments, the metal-centered Lewis-acidic component of the carbonylation catalyst includes a dianionic tetradentate ligand. In some embodiments, the dianionic tetradentate ligand is selected from the group consisting of: porphyrin ligands; salen ligands; dibenzotetramethyltetraaza [14]annulene (tmtaa) ligands; phthalocyaninate ligands; and the Trost ligand.

In some embodiments, the carbonylation catalyst includes a carbonyl cobaltate in combination with an aluminum porphyrin compound. In some embodiments, the carbonylation catalyst is [(TPP)Al(THF)$_2$][Co(CO)$_4$], where TPP stands for tetraphenylporphyrin and THF stands for tetrahydrofuran.

In some embodiments, the carbonylation catalyst includes a carbonyl cobaltate in combination with a chromium porphyrin compound.

In some embodiments, the carbonylation catalyst includes a carbonyl cobaltate in combination with a chromium salen compound. In some embodiments, the carbonylation catalyst includes a carbonyl cobaltate in combination with a chromium salophen compound.

In some embodiments, the carbonylation catalyst includes a carbonyl cobaltate in combination with an aluminum salen compound. In some embodiments, the carbonylation catalyst includes a carbonyl cobaltate in combination with an aluminum salophen compound.

In some embodiments, one or more neutral two electron donors coordinate to M $M^1$ or $M^2$ and fill the coordination valence of the metal atom. In some embodiments, the neutral two electron donor is a solvent molecule. In some embodiments, the neutral two electron donor is an ether. In some embodiments, the neutral two electron donor is tetrahydrofuran, diethyl ether, acetonitrile, carbon disulfide, or pyridine. In some embodiments, the neutral two electron donor is tetrahydrofuran. In some embodiments, the neutral two electron donor is an epoxide. In some embodiments, the neutral two electron donor is an ester or a lactone.

$C_3$ and/or $C_4$ Products

Once the beta lactone, such as BPL, is produced within the central reactor, it can be distributed, e.g., fed into two or more of a first $C_3$ reactor, a second $C_3$ reactor, and a first $C_4$ reactor, etc., where the beta lactone is subjected to conditions that convert it to two or more of a first $C_3$ product, a second $C_3$ product, and a first $C_4$ product. This reaction stage is alternately referred to herein as the beta lactone conversion stage.

As used herein the term "$C_3$ reactor" refers to a chemical reactor and related components that convert the beta lactone, such as BPL, into the "$C_3$ product" which means a compound or polymer that includes a three-carbon chain. Representative examples of $C_3$ products include polypropiolactone (PPL), polyacrylic acid, an α,β-unsaturated acid, such as acrylic acid, an α,β-unsaturated ester, an α,β-unsaturated amide or 1,3-propanediol (PDO).

As used herein the term "$C_4$ reactor" refers to a chemical reactor and its related components that convert the beta lactone, e.g., BPL, into the "$C_4$ product" which means a compound or polymer that includes a four-carbon chain. Representative examples of $C_4$ products include succinic anhydride, succinic acid, 1,4 butanediol (BDO), tetrahydrofuran (THF) or gamma butyrolactone (GBL).

The disclosed systems may produce $C_3$ and/or $C_4$ products. In certain embodiments, the system comprises the first $C_3$ reactor and the first $C_4$ reactor for the production of at least one $C_1$ product and at least one $C_4$ product. In some embodiments, the disclosed systems produce at least a first $C_3$ product and at least a first $C_4$ product, each of which is formed from the beta lactone (e.g., BPL).

In some embodiments, the disclosed systems produce at least a first $C_3$ selected from the group consisting of an α,β-unsaturated acid, such as AA, an α,β-unsaturated ester, an α,β-unsaturated amide, PPL, polyacrylic acid and PDO and at least a first $C_4$ product, succinic anhydride, each of which is formed from BPL.

Lactone to $C_3$ Products

In certain embodiments, the system comprises the first $C_3$ reactor and the second $C_3$ reactor for the production of at least two or more $C_3$ products which differ from one another. As such, at least two distinct $C_3$ products are formed from the beta lactone (e.g., BPL). For example, a first $C_3$ product may be PPL, whereas a second $C_3$ product may be AA. Alternatively, a first $C_3$ product may be AA, whereas a second $C_3$ product may be PAA, or a salt thereof. In the previous embodiment, AA and PAA are produced in parallel from BPL: the first $C_3$ reactor converts BPL to AA, the first $C_3$ product, and the second $C_3$ reactor converts BPL to an AA intermediate and to PAA, the second $C_3$ product. In certain embodiments, the various α,β-unsaturated esters, such as methyl and ethyl acrylate, as well as the various α,β-unsaturated amides, are considered different from one another. Thus, the first $C_3$ product may be methyl acrylate, and the second $C_3$ product may be ethyl acrylate, where these products are regarded as differing from one another.

In other embodiments, the various α,β-unsaturated esters, such as methyl and ethyl acrylate are not considered different from one another. Thus, the first $C_3$ product may be methyl acrylate, and the second $C_3$ product may be ethyl acrylate, where these products are not regarded as differing from one another. Such embodiments necessarily include another, e.g., third $C_3$ reaction zone and/or first $C_4$ reaction zone for making at least one product that is other than an α,β-unsaturated ester.

In certain embodiments, the disclosed systems include one or more additional (third, fourth, fifth, sixth, seventh, eighth, ninth, tenth, etc.) $C_3$ reaction zones that produce corresponding (third, fourth, fifth, sixth, seventh, eighth, ninth, tenth, etc.) $C_1$ products.

In certain embodiments, the first $C_3$ product and the second $C_3$ product are independently selected from an α,β-unsaturated acid, an α,β-unsaturated ester, an α,β-unsaturated amide, a $C_3$ polymer and 1,3-propanediol (PDO).

In certain embodiments, the first $C_3$ product is polypropiolactone (PPL). In certain embodiments, the first $C_3$ product is acrylic acid.

In certain embodiments, the first $C_3$ product is PPL, and the system further comprises a third $C_3$ reactor, comprising an inlet fed by the outlet stream comprising PPL of the first $C_3$ reactor, a third $C_3$ reaction zone that converts at least some of the PPL to a third $C_3$ product, and an outlet which provides an outlet stream comprising the third $C_3$ product.

In certain embodiments, the third $C_3$ product is acrylic acid.

In certain embodiments, the first $C_3$ reaction zone converts BPL to PPL. In certain embodiments, the second $C_3$ reaction zone converts BPL to PPL. In certain embodiments, the third $C_3$ reaction zone converts BPL to PPL. In certain embodiments, the fourth $C_3$ reaction zone converts BPL to PPL. In certain embodiments, the fifth $C_3$ reaction zone converts BPL to PPL. In certain embodiments, the sixth, seventh, eighth, ninth and/or tenth $C_3$ reaction zone converts BPL to PPL.

In certain embodiments, the first $C_3$ reaction zone converts BPL to AA. In certain embodiments, the second $C_3$ reaction zone converts BPL to AA. In certain embodiments, the third $C_3$ reaction zone converts BPL to AA. In certain embodiments, the fourth $C_3$ reaction zone converts BPL to AA. In certain embodiments, the fifth $C_3$ reaction zone converts BPL to AA. In certain embodiments, the sixth, seventh, eighth, ninth and/or tenth $C_3$ reaction zone converts BPL to AA.

In certain embodiments, the first $C_3$ reaction zone converts BPL to an α,β-unsaturated ester. In certain embodiments, the second $C_3$ reaction zone converts BPL to an α,β-unsaturated ester. In certain embodiments, the third $C_3$ reaction zone converts BPL to an α,β-unsaturated ester. In certain embodiments, the fourth $C_3$ reaction zone converts BPL to an α,β-unsaturated ester. In certain embodiments, the fifth $C_3$ reaction zone converts BPL to an α,β-unsaturated ester. In certain embodiments, the sixth, seventh, eighth, ninth and/or tenth $C_3$ reaction zone converts BPL to an α,β-unsaturated ester.

In certain embodiments, the first $C_3$ reaction zone converts BPL to an α,β-unsaturated amide. In certain embodiments, the second $C_3$ reaction zone converts BPL to an α,β-unsaturated amide. In certain embodiments, the third $C_3$ reaction zone converts BPL to an α,β-unsaturated amide. In certain embodiments, the fourth $C_3$ reaction zone converts BPL to an α,β-unsaturated amide. In certain embodiments, the fifth $C_3$ reaction zone converts BPL to an α,β-unsaturated amide. In certain embodiments, the sixth, seventh, eighth, ninth and/or tenth $C_3$ reaction zone converts BPL to an α,β-unsaturated amide.

AA and α,β-Unsaturated Esters

In certain embodiments, the product of the beta lactone conversion stage is an α,β-unsaturated carboxylic acid or ester. There are a number of options possible for converting beta lactones via thermolysis or alcoholoysis to a carboxylic acid (e.g., AA) or an ester (e.g., acrylate esters), respectively. In one embodiment, BPL is fed directly to a reactor containing heated phosphoric acid, optionally including copper metal, a copper salt or other catalyst, to produce AA vapors that are continuously removed to avoid the formation of unwanted byproducts. The formation of AA can be run at atmospheric, super-atmospheric or sub-atmospheric pressures, at temperatures as high as 300° C. The AA produced is then condensed and purified by any of the methods known to one skilled in the art. Additional compounds useful in converting beta lactones to carboxylic acids include, for example, sulfuric acid, zinc chloride, sodium bisulfate, boric acid, boric anhydride, phosphorus pentoxide as well as metallic catalysis such as, aluminum oxide, iron oxides, titanium oxides, etc. Further, basic catalysis may be use including calcium hydroxide, magnesium oxide, borax, disodium phosphate, etc.

In certain embodiments, water may be added to this process to act as a catalyst. Without being bound by theory or limiting the scope of the present invention, it is believed water can aid this conversion by opening the beta lactone to form a beta hydroxy acid intermediate which then dehydrates to provide the desired α,β-unsaturated acid and regenerate the water. The water may be added to the beta lactone stream before entering the second reaction zone, or it may be present in (or added independently to) the second reaction zone. In certain embodiments, the conversion of BPL to AA is performed using methods such as those disclosed in U.S. Pat. Nos. 3,176,042, 2,485,510, 2,623,067, 2,361,036. In other embodiments, the acrylate production may be base catalyzed, see for example *Journal of Organic Chemistry*, 57(1), 389-91(1992).

Many catalysts known in the art can be used, or adapted for this step. In certain embodiments, conditions include reaction with dehydrating agents such as sulfuric acid, phosphoric acid or esters thereof as described in U.S. Pat. Nos. 2,352,641; 2,376,704; 2,449,995; 2,510,423; 2,623,067; 3,176,042, and in British Patent No. 994,091.

In other embodiments, the lactone can be reacted with a halogenic compound to yield a beta halo acid, beta halo ester, or beta halo acid halide, which may then undergo dehydrohalogenation and/or solvolysis to afford the corresponding AA or α,β-unsaturated ester. In certain embodiments, conditions disclosed in U.S. Pat. No. 2,422,728 are used in this process.

Similarly, several methods can be employed to convert a beta lactone to an α,β-unsaturated ester. For example, most methods use an alcohol in the beta lactone conversion stage (or added to the beta lactone stream before it is fed to this stage) to facilitate ring opening of the beta lactone to a beta hydroxy ester, or beta alkoxy acid, both of which can convert to α,β-unsaturated esters. In certain embodiments, the lactone conversion is performed in the presence of an alcohol. In certain embodiments, the lactone conversion is performed in the presence of a $C_{1-20}$ alcohol. In certain embodiments, the lactone conversion is performed in the presence of a $C_{1-8}$ alcohol. In certain embodiments, the lactone conversion is performed in the presence of an alcohol selected from the group consisting of: methanol, ethanol, propanol, butanol, hexanol, and 2-ethyl-hexanol to make the corresponding acrylate ester. In certain embodiments, the alcohol used is a heptyl alcohol, an octyl alcohol, a nonyl alcohol, an n-decyl alcohol, an n-undecyl alcohol, a cetyl alcohol, an n-dodecyl alcohol, an n-tetradecyl alcohol and other primary alcohols. Further, other alcohols can be used in the BPL conversion, for example, sec-butyl alcohol, tert-butyl alcohol, allyl alcohol, beta-ethoxy-ethyl alcohol, diethylene glycol monoethyl either, cycloheanol, furfuryl alcohol benzyl alcohol, and ethylene glycol among others as described above.

The beta lactone conversion is generally performed in the presence of a catalyst. For example, in certain embodiments, the beta lactone is reacted with an alcohol in the presence of a dehydrating catalyst. Exemplary dehydrating catalysts include, for example, metal oxides (e.g., aluminum oxides, titanium oxides), zeolites, silica, and alumino-silicates, among others. Typically, such a conversion is performed in the liquid phase, and the product esters are isolated by distillation.

In certain embodiments, the beta lactone conversion can be performed with activated carbon as a catalyst to produce α,β-unsaturated esters. In certain embodiments, the beta lactone is reacted with an alcohol in the gas phase and over an activated carbon catalyst to produce esters. The activated carbon can be supplied in any form, for example, powdered, granulated, extruded, beads, impregnated with other elements (e.g., iodine, silver, metallic cations, etc.).

In certain embodiments, the reaction may include a polymerization inhibitor to prevent the formation of polymers. Exemplary polymerization inhibitors include copper, copper salts, hydroquinone, manganese, manganese salts, chromium, and chromium salts.

As described above, the beta lactone conversion can be operated within a variety of temperature and pressure ranges when $\alpha,\beta$-unsaturated carboxylic acid or ester are the desired products. In certain embodiments, the temperature can range from about 0° C. to about 300° C. In certain embodiments, the temperature ranges from about 0° C. to 50° C. In certain embodiments, the temperature ranges from about 0° C. to 100° C. In certain embodiments, the temperature ranges from about 0° C. to 150° C. In certain embodiments, the temperature ranges from about 0° C. to 200° C. In certain embodiments, the temperature ranges from about 50° C. to 100° C. In certain embodiments, the temperature ranges from about 50° C. to 150° C. In certain embodiments, the temperature ranges from about 50° C. to 200° C. In certain embodiments, the temperature ranges from about 100° C. to 150° C. In certain embodiments, the temperature ranges from about 100° C. to 200° C. In certain embodiments, the temperature ranges from about 100° C. to 250° C. In certain embodiments, the temperature ranges from about 150° C. to 250° C. In certain embodiments, the temperature ranges from about 150° C. to 300° C. In certain embodiments, the temperature ranges from about 200° C. to 300° C.

In certain embodiments, the pressure can range from about 0.01 atmospheres to about 500 atmospheres (absolute). In certain embodiments, the pressure can range from about 0.01 atmospheres to about 10 atmospheres (absolute). In certain embodiments, the pressure can range from about 0.01 atmospheres to about 50 atmospheres (absolute). In certain embodiments, the pressure can range from about 1 atmosphere to about 10 atmospheres (absolute). In certain embodiments, the pressure can range from about 1 atmosphere to about 50 atmospheres (absolute). In certain embodiments, the pressure can range from about 1 atmosphere to about 100 atmospheres (absolute). In certain embodiments, the pressure can range from about 10 atmospheres to about 50 atmospheres (absolute). In certain embodiments, the pressure can range from about 10 atmospheres to about 100 atmospheres (absolute). In certain embodiments, the pressure can range from about 50 atmospheres to about 100 atmospheres (absolute). In certain embodiments, the pressure can range from about 50 atmospheres to about 200 atmospheres (absolute). In certain embodiments, the pressure can range from about 100 atmospheres to about 200 atmospheres (absolute). In certain embodiments, the pressure can range from about 100 atmospheres to about 250 atmospheres (absolute). In certain embodiments, the pressure can range from about 200 atmospheres to about 300 atmospheres (absolute). In certain embodiments, the pressure can range from about 200 atmospheres to about 500 atmospheres (absolute). In certain embodiments, the pressure can range from about 250 atmospheres to about 500 atmospheres (absolute).

In some embodiments, the pressure used in provided methods and systems for converting beta lactones to alpha beta unsaturated acids or esters is less than about 5 atmospheres (absolute). In some embodiments, the pressure used in provided methods and systems is less than about 1 atmosphere (absolute). In some embodiments, the pressure can range from about 0.01 atmospheres to about 1 atmosphere (absolute). In some embodiments, the pressure can range from about 0.1 atmospheres to about 0.8 atmospheres (absolute). In some embodiments, the pressure can range from about 0.1 atmospheres to about 0.5 atmospheres (absolute). In some embodiments, the pressure can range from about 0.01 atmospheres to about 0.1 atmospheres (absolute). In some embodiments, the pressure can range from about 0.4 atmospheres to about 1 atmosphere (absolute). In some embodiments, the pressure can range from about 0.05 atmospheres to about 0.1 atmospheres (absolute).

Methods of producing $\alpha,\beta$-unsaturated esters from beta lactones are described in U.S. Pat. Nos. 2,466,501, 2,376,704.

AA Via Celanese Process

In certain embodiments, AA and its esters are prepared according to the process developed by the Celanese Corporation for the thermolysis of BPL, formed from the product of the reaction of formaldehyde with ketene, to produce AA and its esters. In such embodiments, the central reactor receives formaldehyde and ketene that are converted to BPL. In certain embodiments, thermolysis of BPL proceeds with phosphoric acid using a copper powder catalyst at 140-180° C. and 25-250 bar to quantitatively form AA. In some embodiments, this reaction may be catalyzed by adding water. If the same reaction is run in the presence of an alcohol, the corresponding acrylate ester is formed directly.

$\alpha,\beta$-Unsaturated Amides

Alternatively, ammonia or an organic amine may be present in this stage to facilitate ring opening of the beta lactone to a beta hydroxy amide, which can be converted to $\alpha,\beta$-unsaturated amides. In certain embodiments, the lactone conversion is performed in the presence of ammonia to produce acrylamide. In certain embodiments, the lactone conversion is performed in the presence of a $C_{1-20}$ amine to produce N-substituted acrylamide derivatives (e.g., $\alpha,\beta$-unsaturated amide). Exemplary amines include for example methyl amine, ethyl amine, propyl amines, butyl amines, amyl amines, and dialkyl amines. In certain embodiments, the amine and the beta lactone are both soluble in water.

As described above, the beta lactone conversion can be operated within a variety of temperature and pressure ranges when $\alpha,\beta$-unsaturated amides are the desired products. Some of the reactions are exothermic and therefore lower temperatures may be useful, as well as sufficient heat transfer to control reaction temperature. As described above, the beta lactone conversion can be operated within a variety of temperature and pressure ranges when 4-unsaturated amides are the desired products. In certain embodiments, the temperature can range from about 0° C. to about 300° C. In certain embodiments, the temperature ranges from about 0° C. to 50° C. In certain embodiments, the temperature ranges from about 0° C. to 100° C. In certain embodiments, the temperature ranges from about 0° C. to 150° C. In certain embodiments, the temperature ranges from about 0° C. to 200° C. In certain embodiments, the temperature ranges from about 50° C. to 100° C. In certain embodiments, the temperature ranges from about 50° C. to 150° C. In certain embodiments, the temperature ranges from about 50° C. to 200° C. In certain embodiments, the temperature ranges from about 100° C. to 150° C. In certain embodiments, the temperature ranges from about 100° C. to 200° C. In certain embodiments, the temperature ranges from about 100° C. to 250° C. In certain embodiments, the temperature ranges from about 150° C. to 250° C. In certain embodiments, the temperature ranges from about 150° C. to 300° C. In certain embodiments, the temperature ranges from about 200° C. to 300° C.

In certain embodiments, the pressure can range from about 0.01 atmospheres to about 500 atmospheres (absolute). In certain embodiments, the pressure can range from about 0.01 atmospheres to about 10 atmospheres (absolute). In certain embodiments, the pressure can range from about 0.01 atmospheres to about 50 atmospheres (absolute). In certain embodiments, the pressure can range from about 1 atmosphere to about 10 atmospheres (absolute). In certain embodiments, the pressure can range from about 1 atmosphere to about 50 atmospheres (absolute). In certain embodiments, the pressure can range from about 1 atmosphere to about 100 atmospheres (absolute). In certain embodiments, the pressure can range from about 10 atmospheres to about 50 atmospheres (absolute). In certain embodiments, the pressure can range from about 10 atmospheres to about 100 atmospheres (absolute). In certain embodiments, the pressure can range from about 50 atmospheres to about 100 atmospheres (absolute). In certain embodiments, the pressure can range from about 50 atmospheres to about 200 atmospheres (absolute). In certain embodiments, the pressure can range from about 100 atmospheres to about 200 atmospheres (absolute). In certain embodiments, the pressure can range from about 100 atmospheres to about 250 atmospheres (absolute). In certain embodiments, the pressure can range from about 200 atmospheres to about 300 atmospheres (absolute). In certain embodiments, the pressure can range from about 200 atmospheres to about 500 atmospheres (absolute). In certain embodiments, the pressure can range from about 250 atmospheres to about 500 atmospheres (absolute).

In some embodiments, the pressure used in provided methods and systems for converting beta lactones to alpha beta unsaturated amides is less than about 5 atmospheres (absolute). In some embodiments, the pressure used in provided methods and systems is less than about 1 atmosphere (absolute). In some embodiments, the pressure can range from about 0.01 atmospheres to about 1 atmosphere (absolute). In some embodiments, the pressure can range from about 0.1 atmospheres to about 0.8 atmospheres (absolute). In some embodiments, the pressure can range from about 0.1 atmospheres to about 0.5 atmospheres (absolute). In some embodiments, the pressure can range from about 0.01 atmospheres to about 0.1 atmospheres (absolute). In some embodiments, the pressure can range from about 0.4 atmospheres to about 1 atmosphere (absolute). In some embodiments, the pressure can range from about 0.05 atmospheres to about 0.1 atmospheres (absolute).

Methods of producing α,β-unsaturated amides from beta lactones are described in U.S. Pat. No. 2,548,155.

Lactone to Polymers

In certain embodiments, the beta lactone from the carbonylation is fed into a subsequent stage comprising a polymerization catalyst, described in more detail below. This provides the opportunity to produce biodegradable polyesters such as poly(3-hydroxy butyrate) (P-3HB), and polypropiolactone (PPL) without the need to handle and transport beta lactones.

In certain embodiments where the beta lactone conversion comprises polymerizing the beta lactone, the step includes contacting the beta lactone with a polymerization catalyst, optionally in the presence of one or more solvents. Suitable solvents can include, for example, hydrocarbons, ethers, esters, ketones, nitriles, amides, sulfones, halogenated hydrocarbons, and the like. In certain embodiments, the solvent is selected such that the polymer formed is soluble in the reaction medium.

In certain embodiments where the beta lactone conversion comprises polymerizing the beta lactone to form a polyester, the step comprises a continuous polymerization. Such continuous polymerizations can be conducted in a continuous stirred tank reactor or a plug flow reactor such that polymer or polymer solution is withdrawn at essentially the same rate it is formed. Polymerization of lactones to polyester can be performed with a number of polymerization initiators including, for example, alcohols, amines, polyols, polyamines, and diols, amongst others. Further a variety of catalysts may be used in the polymerization reaction, including by not limited to metals (e.g., lithium, sodium, potassium, magnesium, calcium, zinc, aluminum, titanium, cobalt, etc.) metal oxides, carbonates of alkali- and alkaline earth metals, borates, silicates, of various metals. In some variations, catalysts that may be used in the polymerization reaction, include for example metals (e.g., lithium, sodium, potassium, magnesium, calcium, zinc, aluminum, titanium, cobalt, etc.) metal oxides, salts of alkali and alkaline earth metals (such as carbonates, borates, hydroxides, alkoxides, and carboxylates), and borates, silicates, or salts of other metals.

U.S. Pat. Nos. 3,169,945 and 3,678,069 describe methods of producing polyesters from beta lactones.

Polymerization Catalysts

Many catalysts are known for the ring-opening polymerization of lactones (such as caprolactone and beta lactones). Any such catalyst can be employed.

Catalysts suitable for the ring-opening polymerization of the methods disclosed herein are disclosed, for example, in: Journal of the American Chemical Society (2002), 124(51), 15239-15248 *Macromolecules*, vol. 24, No. 20, pp. 5732-5733, *Journal of Polymer Science*, Part A-1, vol. 9, No. 10, pp. 2775-2787; Inoue, S., Y. Tomoi, T. Tsuruta & J. Furukawa; *Macromolecules*, vol. 26, No. 20, pp. 5533-5534; *Macromolecules*, vol. 23, No. 13, pp. 3206-3212; *Polymer Preprints* (1999), 40(1), 508-509; *Macromolecules*, vol. 21, No. 9, pp. 2657-2668; and *Journal of Organometallic Chemistry*, vol. 341, No. 1-3, pp. 83-9; and in U.S. Pat. Nos. 3,678,069, 3,169,945, 6,133,402; 5,648,452; 6,316,590; 6,538,101; and 6,608,170.

In certain embodiments, suitable catalysts include carboxylate salts of metal ions or organic cations. In certain embodiments, a carboxylate salt is other than a carbonate.

In certain embodiments, the polymerization catalyst is combined with BPL in a molar ratio up to about 1:100,000 polymerization catalyst:BPL. In certain embodiments, the ratio is from about 1:100,000 to about 25:100 polymerization catalyst:BPL. In certain embodiments, the polymerization catalyst is combined with BPL in a molar ratio of about 1:50,000 polymerization catalyst:BPL to about 1:25,000 polymerization catalyst:BPL. In certain embodiments, the polymerization catalyst is combined with BPL in a molar ratio of about 1:25,000 polymerization catalyst:BPL to about 1:10,000 polymerization catalyst:BPL. In certain embodiments, the polymerization catalyst is combined with BPL in a molar ratio of about 1:20,000 polymerization catalyst:BPL to about 1:10,000 polymerization catalyst:BPL. In certain embodiments, the polymerization catalyst is combined with BPL in a molar ratio of about 1:15,000 polymerization catalyst:BPL to about 1:5,000 polymerization catalyst:BPL. In certain embodiments, the polymerization catalyst is combined with BPL in a molar ratio of about 1:5,000 polymerization catalyst:BPL to about 1:1,000 polymerization catalyst:BPL. In certain embodiments, the polymerization catalyst is combined with BPL in a molar ratio of about 1:2,000 polymerization catalyst:BPL to about 1:500 polymerization catalyst:BPL. In certain embodiments, the polymerization catalyst is combined with BPL in a molar ratio of about 1:1,000 polymerization catalyst:BPL to about 1:200 polymerization catalyst:BPL. In certain embodiments, the polymerization catalyst is combined with BPL in a molar ratio of about 1:500 polymerization catalyst:BPL to about 1:100 polymerization catalyst:BPL. In certain embodiments the molar ratio of polymerization catalyst:BPL is about 1:50,000, 1:25,000, 1:15,000, 1:10,000, 1:5,000, 1:1,000, 1:500, 1:250 or a range including any two of these values. In certain embodiments, the polymerization catalyst is combined with BPL in a molar ratio of about 1:100 polymerization catalyst:BPL to about 25:100 polymerization catalyst:BPL. In certain embodiments the molar ratio of polymerization catalyst:BPL is about 1:100, 5:100, 10:100, 15:100, 20:100, 25:100 or a range including any two of these values.

In certain embodiments, where the polymerization catalyst comprises a carboxylate salt, the carboxylate has a structure such that upon initiating polymerization of BPL, the polymer chains produced have an acrylate chain end. In certain embodiments, the carboxylate ion on a polymerization catalyst is the anionic form of a chain transfer agent (CTA) used in the polymerization process.

In certain embodiments, the carboxylate salt of the polymerization catalyst is an acrylate salt (i.e., the anionic form) of a compound

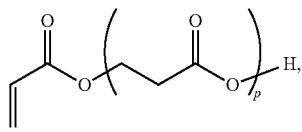

or a mixture of any two or more of these, where p is from 0 to 9. In certain embodiments, p is from 0 to 5. In certain embodiments, the carboxylate salt of the polymerization catalyst is an acrylate salt (i.e., of compound above where p=0).

In certain embodiments, the carboxylate salt of the polymerization catalyst is a salt of an acrylic acid dimer,

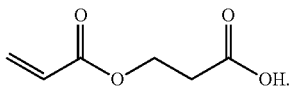

In certain embodiments, the carboxylate salt of the polymerization catalyst is a salt of an acrylic acid trimer,

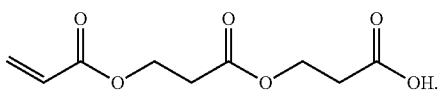

In certain embodiments, where the polymerization catalyst comprises a carboxylate salt, the carboxylate is the anionic form of a $C_{1-40}$ carboxylic acid. In certain embodiments, the carboxylate salt can be a salt of a polycarboxylic acid (e.g. a compound having two or more carboxylic acid groups). In certain embodiments, the carboxylate comprises the anion of a $C_{1-20}$ carboxylic acid. In certain embodiments, the carboxylate comprises the anion of a $C_{1-12}$ carboxylic acid. In certain embodiments, the carboxylate comprises the anion of a $C_{1-8}$ carboxylic acid. In certain embodiments, the carboxylate comprises the anion of a $C_{1-4}$ carboxylic acid. In certain embodiments, the carboxylate comprises the anion of an optionally substituted benzoic acid. In certain embodiments, the carboxylate is selected from the group consisting of: formate, acetate, propionate, valerate, butyrate, $C_{5-10}$ aliphatic carboxylate, and $C_{10-20}$ aliphatic carboxylate.

As noted, in certain embodiments, the polymerization catalyst comprises a carboxylate salt of an organic cation. In certain embodiments, the polymerization catalyst comprises a carboxylate salt of a cation wherein the positive charge is located at least partially on a nitrogen, sulfur, or phosphorus atom. In certain embodiments, the polymerization catalyst comprises a carboxylate salt of a nitrogen cation. In certain embodiments, the polymerization catalyst comprises a carboxylate salt of a cation selected from the group consisting of: ammonium, amidinium, guanidinium, a cationic form of a nitrogen heterocycle, and any combination of two or more of these. In certain embodiments, the polymerization catalyst comprises a carboxylate salt of a phosphorus cation. In certain embodiments, the polymerization catalyst comprises a carboxylate salt of a cation selected from the group consisting of: phosphonium and phosphazenium. In certain embodiments, the polymerization catalyst comprises a carboxylate salt of a sulfur-containing cation. In certain embodiments, the polymerization catalyst comprises a sulfonium salt.

In certain embodiments, the polymerization catalyst comprises a carboxylate salt of a metal. In certain embodiments, the polymerization catalyst comprises a carboxylate salt of a alkali or alkaline earth metal. In certain embodiments, the polymerization catalyst comprises a carboxylate salt of an alkali metal. In certain embodiments, the polymerization catalyst comprises a carboxylate salt of sodium or potassium. In certain embodiments, the polymerization catalyst comprises a carboxylate salt of sodium.

In certain embodiments, the polymerization catalyst comprises a carboxylate salt of a protonated amine:

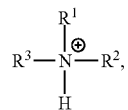

where:
each $R^1$ and $R^2$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein $R^1$ and $R^2$ can be taken together with intervening atoms to form one or more optionally substituted rings optionally containing one or more additional heteroatoms;

each $R^3$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^3$ group can be taken with an $R^1$ or $R^2$ group to form one or more optionally substituted rings.

In certain embodiments where the polymerization catalyst comprises a carboxylate salt of a protonated amine, the protonated amine is selected from the group consisting of:

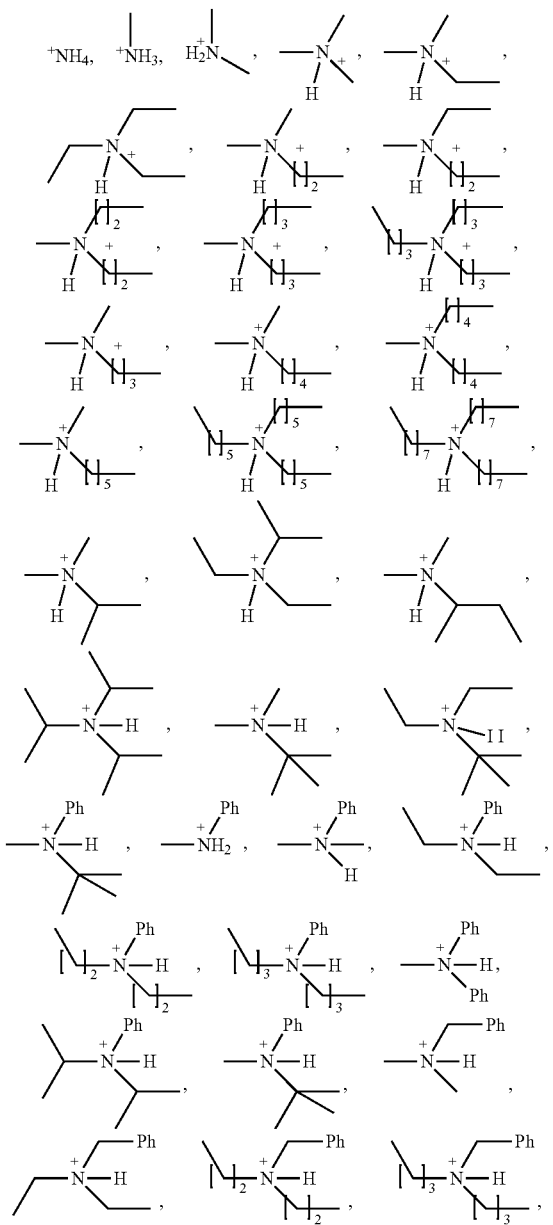

In certain embodiments, the polymerization catalyst comprises a carboxylate salt of a quaternary ammonium salt:

$$R^3-\overset{R^1}{\underset{R^4}{\overset{|}{N}}}-R^2,$$

where:
each $R^1$, $R^2$ and $R^3$ is described above; and
each $R^4$ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^4$ group can be taken with an $R^1$, $R^2$ or $R^3$ group to form one or more optionally substituted rings.

In certain embodiments, a polymerization catalyst comprises a carboxylate salt of a guanidinium group:

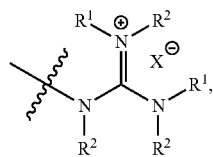

wherein each $R^1$ and $R^2$ is independently as defined above and described in classes and subclasses herein. In certain embodiments, each $R^1$ and $R^2$ is independently hydrogen or $C_{1-20}$ aliphatic. In certain embodiments, each $R^1$ and $R^2$ is independently hydrogen or $C_{1-12}$ aliphatic. In certain embodiments, each $R^1$ and $R^2$ is independently hydrogen or $C_{1-20}$ heteroaliphatic. In certain embodiments, each $R^1$ and $R^2$ is independently hydrogen or phenyl. In certain embodiments, each $R^1$ and $R^2$ is independently hydrogen or 8- to 10-membered aryl. In certain embodiments, each $R^1$ and $R^2$ is independently hydrogen or 5- to 10-membered heteroaryl. In certain embodiments, each $R^1$ and $R^2$ is independently hydrogen or 3- to 7-membered heterocyclic. In certain embodiments, one or more of $R^1$ and $R^2$ is optionally substituted $C_{1-12}$ aliphatic.

In certain embodiments, any two or more $R^1$ or $R^2$ groups are taken together with intervening atoms to form one or more optionally substituted carbocyclic, heterocyclic, aryl, or heteroaryl rings. In certain embodiments, $R^1$ and $R^2$ groups are taken together to form an optionally substituted 5- or 6-membered ring. In certain embodiments, three or more $R^1$ and/or $R^2$ groups are taken together to form an optionally substituted fused ring system.

In certain embodiments, an $R^1$ and $R^2$ group are taken together with intervening atoms to form a compound selected from:

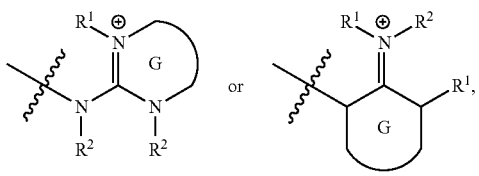

wherein each $R^1$ and $R^2$ is independently as defined above and described in classes and subclasses herein, and Ring G is an optionally substituted 5- to 7-membered saturated or partially unsaturated heterocyclic ring.

It will be appreciated that when a guanidinium cation is depicted as

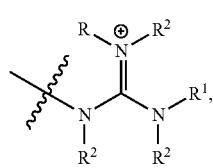

all such resonance forms are contemplated and encompassed by the present disclosure. For example, such groups can also be depicted as

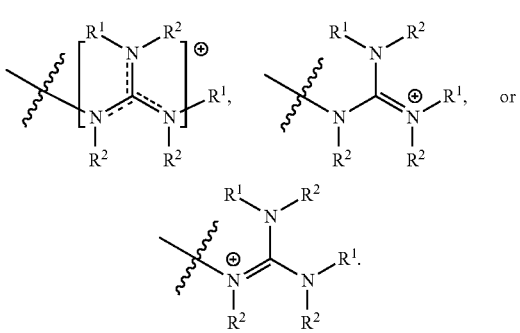

In specific embodiments, a guanidinium cation is selected from the group consisting of:

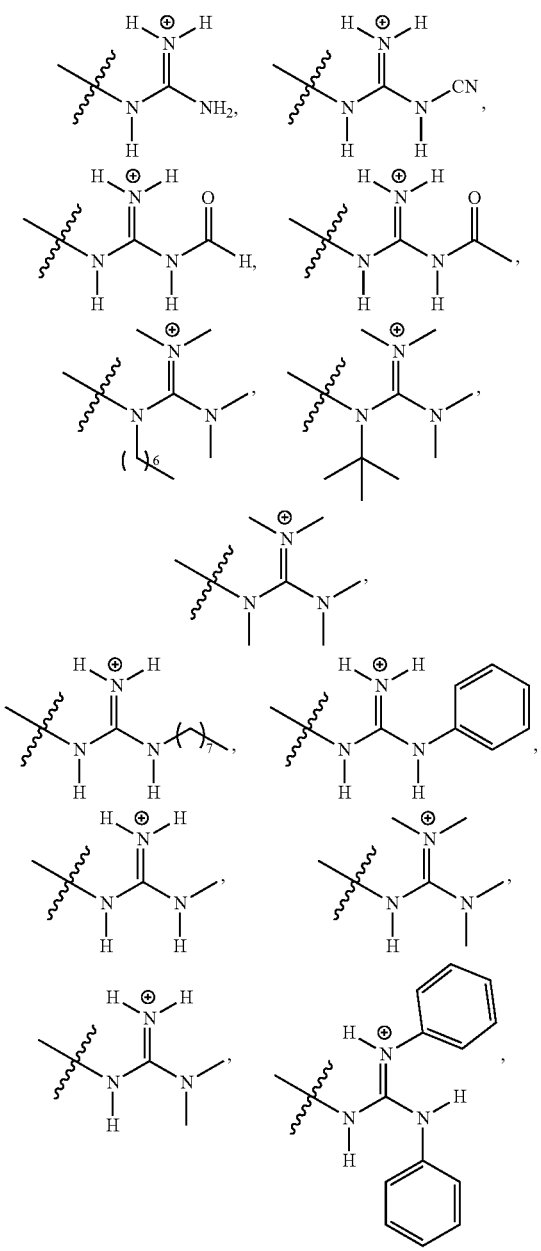

-continued

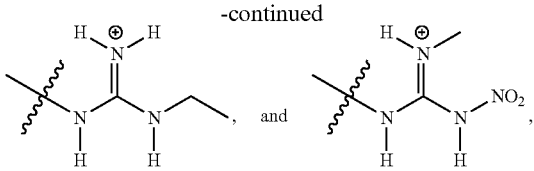

In certain embodiments, a polymerization catalyst comprises a carboxylate salt of a sulfonium group or an arsonium group, such as

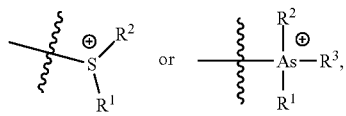

wherein each of $R^1$, $R^2$, and $R^3$ are as defined above and described in classes and subclasses herein.

In specific embodiments, an arsonium cation is selected from the group consisting of:

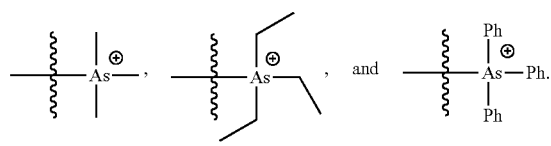

In certain embodiments, a polymerization catalyst comprises a carboxylate salt of an optionally substituted nitrogen-containing heterocycle. In certain embodiments, the nitrogen-containing heterocycle is an aromatic heterocycle. In certain embodiments, the optionally substituted nitrogen-containing heterocycle is selected from the group consisting of: pyridine, imidazole, pyrrolidine, pyrazole, quinoline, thiazole, dithiazole, oxazole, triazole, pyrazolem, isoxazole, isothiazole, tetrazole, pyrazine, thiazine, and triazine.

In certain embodiments, a nitrogen-containing heterocycle includes a quaternarized nitrogen atom. In certain embodiments, a nitrogen-containing heterocycle includes an iminium moiety such as

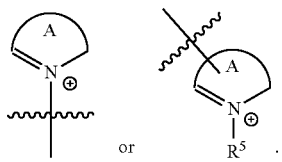

In certain embodiments, the optionally substituted nitrogen-containing heterocycle is selected from the group consisting of pyridinium, imidazolium, pyrrolidinium, pyrazolium, quinolinium, thiazolium, dithiazolium, oxazolium, triazolium, isoxazolium, isothiazolium, tetrazolium, pyrazinium, thiazinium, and triazinium.

In certain embodiments, a nitrogen-containing heterocycle is linked to a metal complex via a ring nitrogen atom. In certain embodiments, a ring nitrogen to which the attachment is made is thereby quaternized, and In certain embodiments, linkage to a metal complex takes the place of an N—H bond and the nitrogen atom thereby remains neutral. In certain embodiments, an optionally substituted N-linked nitrogen-containing heterocycle is a pyridinium derivative. In certain embodiments, optionally substituted N-linked nitrogen-containing heterocycle is an imidazolium derivative. In certain embodiments, optionally substituted N-linked nitrogen-containing heterocycle is a thiazolium derivative. In certain embodiments, optionally substituted N-linked nitrogen-containing heterocycle is a pyridinium derivative.

In certain embodiments, a polymerization catalyst comprises a carboxylate salt of

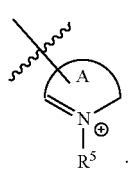

In certain embodiments, ring A is an optionally substituted, 5- to 10-membered heteroaryl group. In certain embodiments, Ring A is an optionally substituted, 6-membered heteroaryl group. In certain embodiments, Ring A is a ring of a fused heterocycle. In certain embodiments, Ring A is an optionally substituted pyridyl group.

In specific embodiments, a nitrogen-containing heterocyclic cation is selected from the group consisting of:

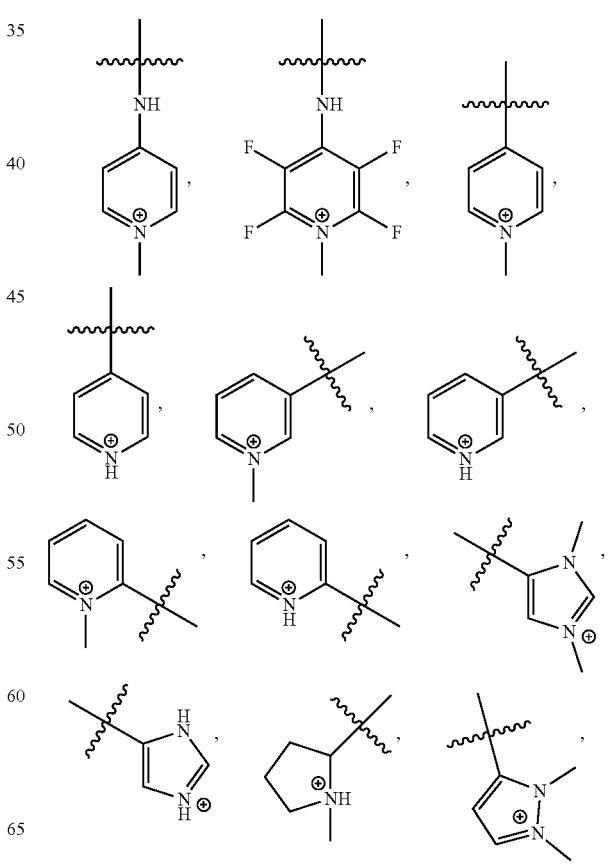

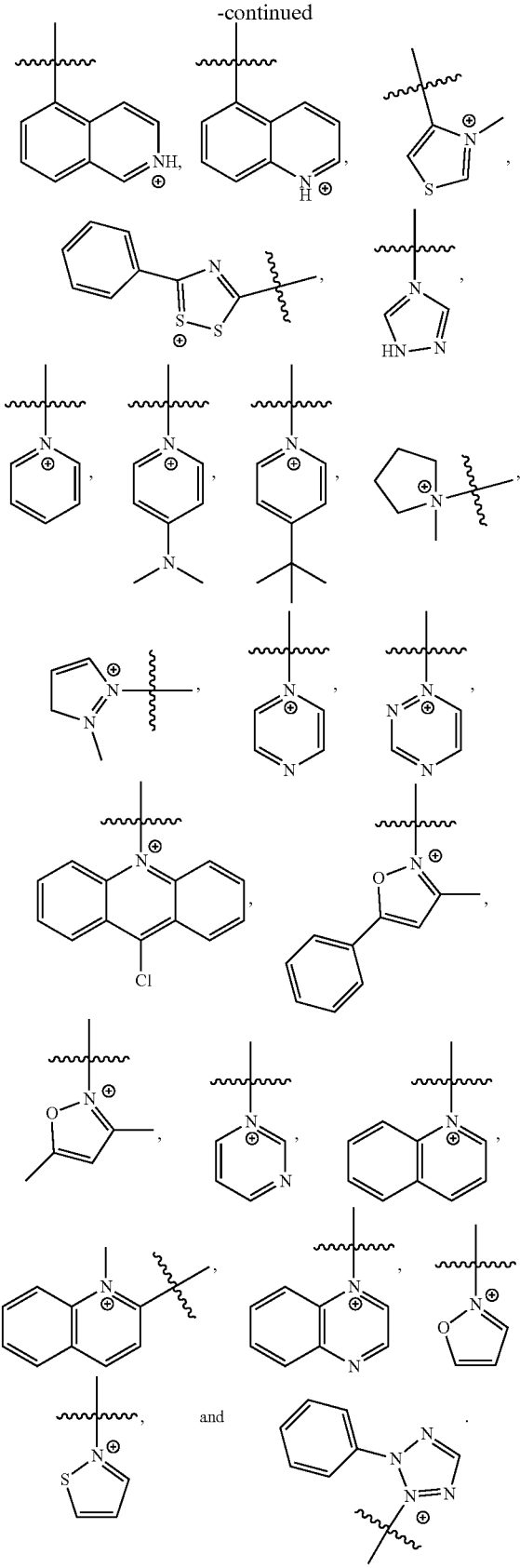

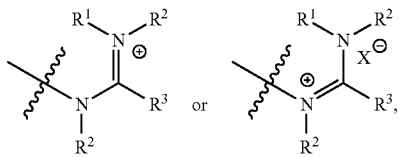

where each $R^1$, $R^2$, and $R^3$ is independently as defined above and described in classes and subclasses herein.

In certain embodiments, a polymerization catalyst comprises a carboxylate salt of

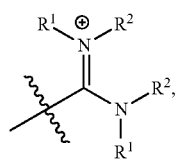

wherein each $R^1$ and $R^2$ is independently as defined above and described in classes and subclasses herein.

In certain embodiments, a polymerization catalyst comprises a carboxylate salt of

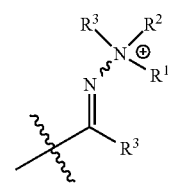

wherein each $R^1$, $R^2$, and $R^3$ is independently as defined above and described in classes and subclasses herein.

In certain embodiments, a polymerization catalyst comprises a carboxylate salt of

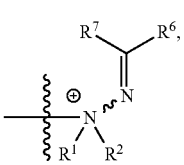

wherein each of $R^1$, $R^2$, $R^6$, and $R^7$ is as defined above and described in classes and subclasses herein.

In certain embodiments, $R^6$ and $R^7$ are each independently an optionally substituted group selected from the group consisting of $C_{1-20}$ aliphatic; $C_{1-20}$ heteroaliphatic; phenyl, and 8-10-membered aryl. In certain embodiments, $R^6$ and $R^7$ are each independently an optionally substituted $C_{1-20}$ aliphatic. In certain embodiments, $R^6$ and $R^7$ are each independently an optionally substituted $C_{1-20}$ heteroaliphatic having. In certain embodiments, $R^6$ and $R^7$ are each independently an optionally substituted phenyl or 8-10-membered aryl. In certain embodiments, $R^6$ and $R^7$ are each independently an optionally substituted 5- to 10-membered heteroaryl. In certain embodiments, $R^6$ and $R^7$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally In certain embodiments, a polymerization catalyst comprises a carboxylate salt of substituted 5- to 10-membered heteroaryl. In certain embodiments, $R^6$ and $R^7$ are each independently an optionally substituted $C_{1-6}$ aliphatic. In certain embodiments, each occurrence of $R^6$ and $R^7$ is independently methyl, ethyl, propyl, butyl, pentyl, hexyl, heptyl, octyl, or benzyl. In certain embodiments, each occurrence of $R^6$ and $R^7$ is independently perfluoro. In certain embodiments, each occurrence of $R^6$ and $R^7$ is independently —$CF_2CF_3$.

In certain embodiments, a polymerization catalyst comprises a carboxylate salt of

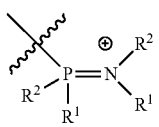

wherein each $R^1$ and $R^2$ is independently as defined above and described in classes and subclasses herein.

In certain embodiments, a polymerization catalyst comprises a carboxylate salt of

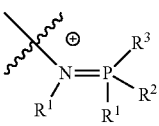

wherein each $R^1$, $R^2$, and $R^3$ is independently as defined above and described in classes and subclasses herein.

In certain embodiments, a cation is

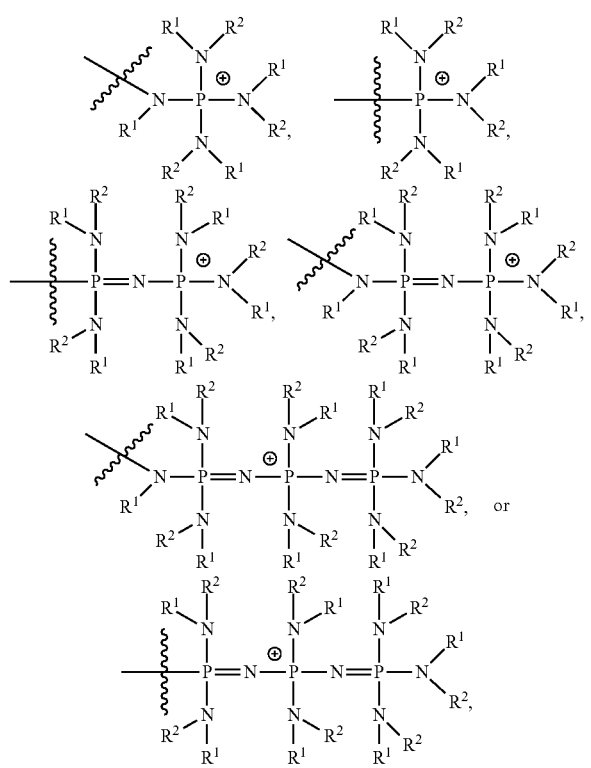

wherein each $R^1$ and $R^2$ is independently as defined above and described in classes and subclasses herein.

In certain embodiments, a polymerization catalyst comprises a carboxylate salt of

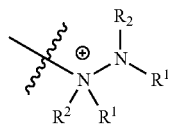

wherein each $R^1$ and $R^2$ is independently as defined above and described in classes and subclasses herein.

In certain embodiments, a polymerization catalyst comprises a carboxylate salt of

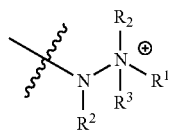

wherein each $R^1$, $R^2$, and $R^3$ is independently as defined above and described in classes and subclasses herein.

In certain embodiments, a polymerization catalyst comprises a carboxylate salt of

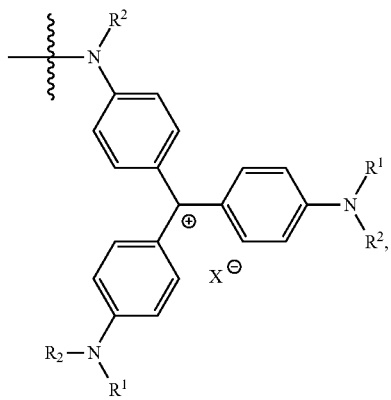

wherein each $R^1$ and $R^2$ is independently as defined above and described in classes and subclasses herein. In certain embodiments, suitable catalysts include transition metal compounds. In certain embodiments, suitable catalysts include acid catalysts. In certain embodiments, the catalyst is a heterogeneous catalyst.

In certain embodiments, any of the foregoing cationic functional groups are attached to a solid support. Examples of suitable solid supports include polymeric solids (e.g. polymer beads, films, fibers, fabrics, particles and the like) as well as inorganic solids (e.g. clays, silicas, aluminas, diatomaceous earth, ceramics, metal oxides, mineral fibers beads or particles, and the like). Specific examples of such supported cationic functional groups include polystyrene resin beads functionalized with ammonium groups, polystyrene resin beads functionalized with phosphonium groups, and polystyrene resin beads functionalized with guanidinium groups. Specific examples of such supported cationic functional groups include silica particles functionalized with ammonium groups, alumina particles functionalized with phosphonium groups, and ceramic beads functionalized with guanidinium groups. In certain embodiments, polymerization catalysts comprise carboxylate salts of any of the foregoing supported solid cationic functional groups. In certain embodiments, polymerization catalysts comprise acrylate salts of any of the foregoing solid supported cationic functional groups.

In certain embodiments, polymerization catalysts comprise cationic solids wherein the cations comprise metal atoms. In certain embodiments, polymerization catalysts comprise carboxylate salts of any of the foregoing supported solid cationic metal atoms. In certain embodiments, polymerization catalysts comprise acrylate salts of any of the foregoing supported solid cationic metal atoms.

In certain embodiments, the carboxylate salt of the polymerization catalyst is a compound:

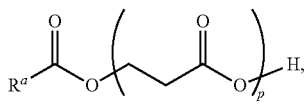

where p is from 0 to 9 and $R^a$ is a non-volatile moiety. The term "non-volatile moiety," as used herein, refers to a moiety or material to which a carboxylate can be attached, and that renders the carboxylate (e.g., when p=0) non-volatile to pyrolysis conditions. In certain embodiments, a non-volatile moiety is selected from the group consisting of glass surfaces, silica surfaces, plastic surfaces, metal surfaces including zeolites, surfaces containing a metallic or chemical coating, membranes (e.g., nylon, polysulfone, silica), microbeads (e.g., latex, polystyrene, or other polymer), and porous polymer matrices (e.g., polyacrylamide, polysaccharide, polymethacrylate). In certain embodiments, a non-volatile moiety has a molecular weight above 100, 200, 500, or 1000 g/mol. In certain embodiments, a non-volatile moiety is part of a fixed or packed bed system. In certain embodiments, a non-volatile moiety is part of a fixed or packed bed system comprising pellets (e.g., zeolite).

In certain embodiments, p is from 0 to 5. In certain embodiments, the carboxylate salt of the polymerization catalyst is an acrylate salt (i.e., of the above compound where p=0).

In certain embodiments, a suitable carboxylate catalyst is heterogeneous. In certain embodiments, a suitable carboxylate catalyst will remain in a reaction zone as a salt or melt after removal of all other products, intermediates, starting materials, byproducts, and other reaction components. In certain embodiments, a suitable carboxylate catalyst (i.e., the above compound where p is from 0 to 9) will remain in a reaction zone as a salt or melt after removal of all AA product stream.

In certain embodiments, a catalyst is recycled for further use in a reaction zone. In certain embodiments, a salt or melt catalyst is recycled to a reaction zone. In certain embodiments, provided methods further comprise withdrawing a recycling stream of homogeneous catalyst to a reaction zone. In certain embodiments, such a recycling stream comprises a high boiling solvent, wherein the solvent's boiling point is above the pyrolysis temperature of PPL and the catalyst remains in the high boiling solvent during pyrolysis while the withdrawn product stream is gaseous.

BPL to AA

In some embodiments, BPL is converted to AA (including, for example, GAA) without isolation of the intermediate PPL, wherein the PPL formed by polymerization of BPL is concurrently converted to AA (including, for example, GAA) via pyrolysis in the same reaction zone (e.g., a "one-pot" method). In certain embodiments, the reaction zone containing the reaction of BPL to PPL is maintained at a temperature at or above the pyrolysis temperature of PPL such that the thermal decomposition of PPL produces AA. Without wishing to be bound by any particular theory, it is believed that in such embodiments as BPL reacts with AA to start polymer chains, thermal decomposition will degrade the polymer to AA.

A one-pot BPL conversion to AA can be operated within a variety of temperature and pressure ranges. In certain embodiments, the temperature can range from about 150° C. to about 300° C. In certain embodiments, the temperature ranges from about 150° C. to about 200° C. In certain embodiments, the temperature ranges from about 150° C. to about 250° C. In certain embodiments, the temperature ranges from about 175° C. to about 300° C. In some embodiments, the temperature ranges from about 200° C. to about 250° C. In certain embodiments, the temperature ranges from about 225° C. to about 275° C. In certain embodiments, the temperature ranges from about 250° C. to about 300° C. In certain embodiments, the temperature ranges from about 200° C. to about 300° C.

In certain embodiments, the pressure used in provided methods and systems can range from about 0.01 atmospheres to about 500 atmospheres (absolute). In certain embodiments, the pressure can range from about 0.01 atmospheres to about 10 atmospheres (absolute). In certain embodiments, the pressure can range from about 0.01 atmospheres to about 50 atmospheres (absolute). In certain embodiments, the pressure can range from about 1 atmosphere to about 10 atmospheres (absolute). In certain embodiments, the pressure can range from about 1 atmosphere to about 50 atmospheres (absolute). In certain embodiments, the pressure can range from about 1 atmosphere to about 100 atmospheres (absolute). In certain embodiments, the pressure can range from about 10 atmospheres to about 50 atmospheres (absolute). In certain embodiments, the pressure can range from about 10 atmospheres to about 100 atmospheres (absolute). In certain embodiments, the pressure can range from about 50 atmospheres to about 100 atmospheres (absolute). In certain embodiments, the pressure can range from about 50 atmospheres to about 200 atmospheres (absolute). In certain embodiments, the pressure can range from about 100 atmospheres to about 200 atmospheres (absolute). In certain embodiments, the pressure can range from about 100 atmospheres to about 250 atmospheres (absolute). In certain embodiments, the pressure can range from about 200 atmospheres to about 300 atmospheres (absolute). In certain embodiments, the pressure can range from about 200 atmospheres to about 500 atmospheres (absolute). In certain embodiments, the pressure can range from about 250 atmospheres to about 500 atmospheres (absolute).

In some embodiments, the pressure used in provided methods and systems for converting BPL to AA is less than about 5 atmospheres (absolute). In some embodiments, the pressure used in provided methods and systems is less than about 1 atmosphere (absolute). In some embodiments, the pressure can range from about 0.01 atmospheres to about 1 atmosphere (absolute). In some embodiments, the pressure can range from about 0.1 atmospheres to about 0.8 atmospheres (absolute). In some embodiments, the pressure can range from about 0.1 atmospheres to about 0.5 atmospheres (absolute). In some embodiments, the pressure can range from about 0.01 atmospheres to about 0.1 atmospheres (absolute). In some embodiments, the pressure can range from about 0.4 atmospheres to about 1 atmosphere (absolute). In some embodiments, the pressure can range from about 0.05 atmospheres to about 0.1 atmospheres (absolute).

PPL to AA

In some embodiments where at least one of the C3 reactors produces PPL, at least a portion of the resulting PPL stream is fed to another C3 where it is converted to AA (including, for example, GAA). In certain embodiments, the reaction zone converting the PPL to AA is maintained at a temperature at or above the pyrolysis temperature of PPL such that the thermal decomposition of PPL produces AA.

PPL conversion to AA can be operated within a variety of temperature and pressure ranges. In certain embodiments, the temperature can range from about 150° C. to about 300° C. In certain embodiments, the temperature ranges from about 150° C. to about 200° C. In certain embodiments, the temperature ranges from about 150° C. to about 250° C. In certain embodiments, the temperature ranges from about 175° C. to about 300° C. In some embodiments, the temperature ranges from about 200° C. to about 250° C. In certain embodiments, the temperature ranges from about 225° C. to about 275° C. In certain embodiments, the temperature ranges from about 250° C. to about 300° C. In certain embodiments, the temperature ranges from about 200° C. to about 300° C.

In certain embodiments, the pressure used in provided methods and systems to convert PPL to AA can range from about 0.01 atmospheres to about 500 atmospheres (absolute). In certain embodiments, the pressure can range from about 0.01 atmospheres to about 10 atmospheres (absolute). In certain embodiments, the pressure can range from about 0.01 atmospheres to about 50 atmospheres (absolute). In certain embodiments, the pressure can range from about 1 atmosphere to about 10 atmospheres (absolute). In certain embodiments, the pressure can range from about 1 atmosphere to about 50 atmospheres (absolute). In certain embodiments, the pressure can range from about 1 atmosphere to about 100 atmospheres (absolute). In certain embodiments, the pressure can range from about 10 atmospheres to about 50 atmospheres (absolute). In certain embodiments, the pressure can range from about 10 atmospheres to about 100 atmospheres (absolute). In certain embodiments, the pressure can range from about 50 atmospheres to about 100 atmospheres (absolute). In certain embodiments, the pressure can range from about 50 atmospheres to about 200 atmospheres (absolute). In certain embodiments, the pressure can range from about 100 atmospheres to about 200 atmospheres (absolute). In certain embodiments, the pressure can range from about 100 atmospheres to about 250 atmospheres (absolute). In certain embodiments, the pressure can range from about 200 atmospheres to about 300 atmospheres (absolute). In certain embodiments, the pressure can range from about 200 atmospheres to about 500 atmospheres (absolute). In certain embodiments, the pressure can range from about 250 atmospheres to about 500 atmospheres (absolute).

In some embodiments, the pressure used in provided methods and systems for converting PPL to AA is less than about 5 atmospheres (absolute). In some embodiments, the pressure used in provided methods and systems is less than about 1 atmosphere (absolute). In some embodiments, the pressure can range from about 0.01 atmospheres to about 1 atmosphere (absolute). In some embodiments, the pressure can range from about 0.1 atmospheres to about 0.8 atmospheres (absolute). In some embodiments, the pressure can range from about 0.1 atmospheres to about 0.5 atmospheres (absolute). In some embodiments, the pressure can range from about 0.01 atmospheres to about 0.1 atmospheres (absolute). In some embodiments, the pressure can range from about 0.4 atmospheres to about 1 atmosphere (absolute). In some embodiments, the pressure can range from about 0.05 atmospheres to about 0.1 atmospheres (absolute).

Lactone to $C_4$ Products

In certain embodiments, the disclosed systems comprise a first $C_4$ reactor comprising an inlet fed by the outlet stream comprising beta lactone from the central reactor. The first $C_4$ reactor converts the beta lactone, such as BPL, into a first $C_4$ product. In certain embodiments, the first $C_4$ product is succinic anhydride (SA).

In certain embodiments, the first $C_4$ product is SA, and the system further comprises a second $C_4$ reactor, comprising an inlet fed by the outlet stream comprising SA of the first $C_4$ reactor, a second $C_4$ reaction zone that converts at least some of the SA to a second $C_4$ product, and an outlet which provides an outlet stream comprising the second $C_4$ product.

In certain embodiments, the second $C_4$ product is succinic acid, 1,4 butanediol (BDO), tetrahydrofuran (THF) or gamma butyrolactone (GBL).

In certain embodiments, the first $C_4$ product is the result of a second carbonylation reaction as shown below where the epoxide is EO and the two-step carbonylation $C_4$ product is SA:

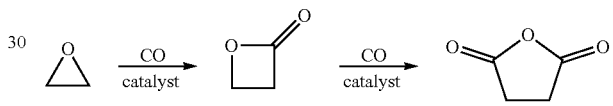

This is a stepwise sequence by which two equivalents of CO are added to the EO to first produce the $C_3$ BPL followed by a second insertion of CO to produce $C_4$ SA. In certain embodiments, the two-step sequence is carried out step-wise in different reactors, wherein the central reactor receives a reaction stream comprising EO and CO and converts them into the BPL, and the first $C_4$ reactor is a different reaction vessel from the central reactor; it receives a reaction stream comprising the BPL and additional CO and converts them into the first $C_4$ product, SA.

In other embodiments, the two-step sequence is carried out in a one-pot sequence in a single reaction vessel, wherein the central reactor receives an inlet stream comprising EO and CO and converts them into BPL. In this instance, the central reactor becomes the first $C_4$ reaction zone when it receives additional CO and converts BPL into a first $C_4$ product, SA.

In certain embodiments, the two-step carbonylation reaction produces the following overall reaction:

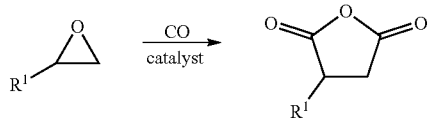

where, $R^1$ is selected from the group consisting of —H and $C_{1-6}$ aliphatic.

In certain embodiments, the two-step carbonylation reaction produces the following overall reaction where the epoxide is propylene oxide and the carbonylation product is methylsuccinic anhydride:

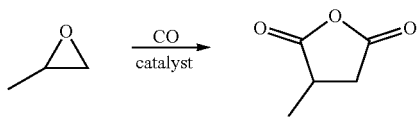

Suitable catalysts and reaction conditions for effecting the above reactions are described herein and also disclosed in published PCT applications WO2012/030619 and WO2013/122905, and U.S. Pat. No. 8,481,756.

Succinic Anhydride to THF, GBL and BDO

Likewise, in certain embodiments, the system may include a first $C_4$ reactor for converting BPL to SA, where the system further comprises a second $C_4$ reaction zone that receives an inlet stream comprising the succinic anhydride from the first $C_4$ reaction zone and converts it to a second $C_4$ product such as 1,4 butanediol (BDO), tetrahydrofuran (THF) or gamma butyrolactone (GBL).

In some embodiments of the system, $C_3$ and/or $C_4$ reaction zones, producing an initial $C_3$ and/or $C_4$ product, can be configured in parallel with subsequent downstream $C_3$ and/or $C_4$ reaction zones to convert the initial $C_1$ and/or $C_4$ product into a subsequent $C_3$ and/or $C_4$ product. For example, in certain embodiments, the system may include a first $C_3$ reaction zone for converting BPL to PPL, where the system further comprises a third $C_3$ reaction zone that receives a reaction stream comprising the PPL from the first $C_3$ reaction zone and converts it to a third $C_3$ product such as AA.

Large Scale AA Production

In another aspect, a system is provided for the production of AA, e.g., an AA production plant, wherein the system produces AA at a rate of about 200 to about 1,000 kilotons per annum (kta). Presently, chemical plants generate approximately 160 kta AA from propylene-based feedstock. Without being bound by theory, the disclosed systems are capable of producing greater output of AA from ethylene-based feedstock. In certain embodiments, the system produces the AA from ethylene. In certain embodiments, the AA is crude AA. In certain embodiments, the AA is glacial AA. In some embodiments, the AA is substantially free of a product or by product of propylene oxidation. In some embodiments, the AA is substantially free of an aldehyde impurity. In some embodiments, the AA is substantially free of stabilizers. In some embodiments, the AA is substantially free of radical polymerization inhibitors. In some embodiments, the AA is substantially free of anti-foam agents.

Specifically, the disclosed systems include a reactor for the oxidation of ethylene to EO, a reactor for carbonylating EO with CO to produce BPL, and reactors for converting BPL to AA, optionally via PPL.

In certain embodiments, the system produces AA at a rate of about 200, 250, 300, 350, 400, 450, 500, 550, 600, 650, 700, 750, 800, 850, 900, 950, 1,000 kta, or within a range including any two of these values.

In certain embodiments, the system comprises
an oxidative reactor, comprising an inlet fed by ethylene, an oxidative reaction zone that converts at least some of the ethylene to ethylene oxide (EU), and an outlet which provides an outlet stream comprising the EU, which is fed to an inlet of a central reactor,
the central reactor, comprising the inlet fed by the outlet stream comprising the EO from the oxidative reactor and a carbon monoxide (CO) source, a central reaction zone that converts at least some of the EU to beta propiolactone (BPL), and an outlet which provides an outlet stream comprising the BPL,
one or more of:
(i) a first $C_3$ reactor, comprising an inlet fed by the outlet stream comprising BPL of the central reactor, a first $C_3$ reaction zone that converts at least some of the BPL to a polypropiolactone (PPL), and an outlet which provides an outlet stream comprising the PPL, and a second $C_3$ reactor, comprising an inlet fed by the outlet stream comprising PPL of the first $C_3$ reactor, a second $C_3$ reaction zone that converts at least some of the PPL to AA, and an outlet which provides an outlet stream comprising the AA, and
(ii) a third $C_3$ reactor, comprising an inlet fed by the outlet stream comprising BPL of the central reactor, a third $C_3$ reaction zone that converts at least some of the BPL to a second $C_3$ product that is other than PPL or AA, and an outlet which provides an outlet stream comprising the second $C_3$ product, and
a controller for independently modulating production of the EO, BPL, AA and, optionally, PPL and any other $C_3$ products.

In some variations, provided is a system for producing AA from ethylene, comprising:
an ethylene source;
a carbon monoxide (CO) source;
an oxidative reactor comprising:
an inlet configured to receive ethylene from the ethylene source,
an oxidative reaction zone configured to convert at least some of the ethylene to ethylene oxide (EO), and
an outlet configured to provide an outlet stream comprising the EO, and feed the outlet stream comprising the EO to an inlet of a central reactor;
the central reactor comprising:
an inlet configured to receive EO from the outlet stream of the oxidative reactor and CO from the CO source,
a central reaction zone configured to convert at least some of the EO to beta propiolactone (BPL), and
an outlet configured to provide an outlet stream comprising the BPL;
one of (i) or (ii), or both:
(i) a first $C_3$ reactor comprising:
an inlet configured to receive the outlet stream comprising BPL of the central reactor,
a first $C_3$ reaction zone configured to convert at least some of the BPL to a polypropiolactone (PPL), and
an outlet configured to provide an outlet stream comprising the PPL, and
a second $C_3$ reactor comprising;
an inlet configured to receive the outlet stream comprising PPL of the first $C_3$ reactor,
a second $C_3$ reaction zone configured to convert at least some of the PPL to AA, and
an outlet configured to provide an outlet stream comprising the AA, and
(ii) a third $C_3$ reactor comprising:
an inlet configured to receive the outlet stream comprising BPL of the central reactor,
a third $C_3$ reaction zone configured to convert at least some of the BPL to AA, and
an outlet configured to provide an outlet stream comprising the AA; and
a controller to independently modulating production of the EO, BPL, AA and, optionally, PPL and any products.

In one embodiment, one of (i) or (ii), or both is (i). Thus, in one variation, provided is a system for producing AA from ethylene, comprising:
an ethylene source;
a carbon monoxide (CO) source;
an oxidative reactor comprising:
an inlet configured to receive ethylene from the ethylene source,
an oxidative reaction zone configured to convert at least some of the ethylene to ethylene oxide (EO), and
an outlet configured to provide an outlet stream comprising the EO, and feed the outlet stream comprising the EO to an inlet of a central reactor;
the central reactor comprising:
an inlet configured to receive the outlet stream comprising the EO from the oxidative reactor and the CO source,
a central reaction zone configured to convert at least some of the EO to beta propiolactone (BPL), and
an outlet configured to provide an outlet stream comprising the BPL;
a first $C_3$ reactor comprising:
an inlet configured to receive the outlet stream comprising BPL of the central reactor,
a first $C_3$ reaction zone configured to convert at least some of the BPL to polypropiolactone (PPL), and
an outlet configured to provide an outlet stream comprising the PPL, and
a second $C_3$ reactor comprising;
an inlet configured to receive the outlet stream comprising PPL of the first $C_3$ reactor,
a second $C_3$ reaction zone configured to convert at least some of the PPL to AA, and
an outlet configured to provide an outlet stream comprising the AA, and
a controller to independently modulating production of the EO, BPL, PPL and AA.

In one embodiment, one of (i) or (ii), or both is (ii). Thus, in one variation, provided is a system for producing AA from ethylene, comprising:
an ethylene source;
a carbon monoxide (CO) source;
an oxidative reactor comprising:
an inlet configured to receive ethylene from the ethylene source,
an oxidative reaction zone configured to convert at least some of the ethylene to ethylene oxide (EO), and
an outlet configured to provide an outlet stream comprising the EO, and feed the outlet stream comprising the EO to an inlet of a central reactor;
the central reactor comprising:
an inlet configured to receive the outlet stream comprising the EO from the oxidative reactor and the CO source,
a central reaction zone configured to convert at least some of the EO to beta propiolactone (BPL), and
an outlet configured to provide an outlet stream comprising the BPL;
a $C_3$ reactor comprising:
an inlet configured to receive the outlet stream comprising BPL of the central reactor,
a $C_3$ reaction zone configured to convert at least some of the BPL to AA, and
an outlet configured to provide an outlet stream comprising the AA; and a controller to independently modulating production of the EO, BPL and AA.

In certain embodiments, the system further comprises one or more of:

(iv) a fourth $C_3$ reactor, comprising an inlet fed by the outlet stream comprising BPL of the central reactor, a fourth $C_3$ reaction zone that converts at least some of the BPL to a $C_3$ product other than acrylic acid, and an outlet which provides an outlet stream comprising the $C_3$ product other than acrylic acid, and (v) a first $C_4$ reactor, comprising an inlet fed by the outlet stream comprising BPL of the central reactor, a first $C_4$ reaction zone that converts at least some of the BPL to a first $C_4$ product, and an outlet which provides an outlet stream comprising the first $C_4$ product.

In some embodiments, the system further comprises one of (iv) or (v), or both:
(iv) a fourth $C_3$ reactor comprising:
an inlet configured to receive the outlet stream comprising BPL of the central reactor,
a fourth $C_3$ reaction zone configured to convert at least some of the BPL to a $C_3$ product other than acrylic acid, and
an outlet configured to provide an outlet stream comprising the $C_3$ product other than acrylic acid, and
(v) a first $C_4$ reactor comprising:
an inlet configured to receive the outlet stream comprising BPL of the central reactor,
a first $C_4$ reaction zone configured to convert at least some of the BPL to a first $C_4$ product, and
an outlet configured to provide an outlet stream comprising the first $C_4$ product.

In certain embodiments, one of (iv) or (v), or both is (iv). Thus, in certain variations, the system further comprises:
another $C_3$ reactor comprising:
an inlet configured to receive the outlet stream comprising BPL of the central reactor,
another $C_3$ reaction zone configured to convert at least some of the BPL to a $C_3$ product other than acrylic acid, and
an outlet configured to provide an outlet stream comprising the $C_3$ product other than acrylic acid.

In certain embodiments, one of (iv) or (v), or both is (v). Thus, in certain variations, the system further comprises:
a $C_4$ reactor comprising:
an inlet configured to receive the outlet stream comprising BPL of the central reactor,
a $C_4$ reaction zone configured to convert at least some of the BPL to a first $C_4$ product, and
an outlet configured to provide an outlet stream comprising the first $C_4$ product.

In another aspect, a method is provided for producing acrylic acid (AA) from ethylene in a single integrated system, the method comprising:
providing ethylene to an oxidative reactor that converts at least some of the ethylene to ethylene oxide (EO),
providing EO to a central reactor that converts at least some of the EO to beta propiolactone (BPL),
and at least one of the following providing steps:
providing BPL to a first reactor that converts at least some of the BPL to AA, and
providing BPL to a reactor that converts at least some of the BPL to polypropiolactone (PPL), and
isolating acrylic acid at a rate of about 200 to about 800 kilotons per annum (kta).

In some variations, provided is a method for producing acrylic acid (AA) from ethylene in a single integrated system, the method comprising:
providing ethylene to an oxidative reactor that converts at least some of the ethylene to ethylene oxide (EO);

providing EO to a central reactor that converts at least some of the EO to beta propiolactone (BPL);

and at least one or both of (i) and (ii):

(i) providing BPL to a first reactor that converts at least some of the BPL to AA, and (ii) providing BPL to a reactor that converts at least some of the BPL to polypropiolactone (PPL).

In certain variations of the foregoing method, BPL is provided to a first reactor that converts at least some of the BPL, and the method further comprises isolating acrylic acid at a rate of about 200 to about 800 kilotons per annum (kta).

In one embodiment, the at least one or both of (i) and (ii) is (i). Thus, in one variation, provided is a method for producing acrylic acid (AA) from ethylene in a single integrated system, the method comprising:

providing ethylene to an oxidative reactor that converts at least some of the ethylene to ethylene oxide (EO);

providing EO to a central reactor that converts at least some of the EO to beta propiolactone (BPL); and providing BPL to a first reactor that converts at least some of the BPL to AA; and optionally isolating acrylic acid at a rate of about 200 to about 800 kilotons per annum (kta).

In another embodiment, the at least one or both of (i) and (ii) is (ii). Thus, in one variation, provided is a method for producing acrylic acid (AA) from ethylene in a single integrated system, the method comprising:

providing ethylene to an oxidative reactor that converts at least some of the ethylene to ethylene oxide (EU);

providing EO to a central reactor that converts at least some of the EU to beta propiolactone (BPL); and providing BPL to a reactor that converts at least some of the BPL to polypropiolactone (PPL).

In yet another embodiment, the at least one or both of (i) and (ii) is both (i) and (ii). Thus, in yet another variation, provided is a method for producing acrylic acid (AA) from ethylene in a single integrated system, the method comprising:

providing ethylene to an oxidative reactor that converts at least some of the ethylene to ethylene oxide (EU);

providing EO to a central reactor that converts at least some of the EU to beta propiolactone (BPL);

providing BPL to a first reactor that converts at least some of the BPL to AA; and providing BPL to a reactor that converts at least some of the BPL to polypropiolactone (PPL); and optionally isolating acrylic acid at a rate of about 200 to about 800 kilotons per annum (kta).

The term "integrated system" as used herein means a single system such as a chemical plant, confined to a single geographic location, and comprising an abutting series of reactors or system components. The integrated system can produce multiple products from a single precursor such as an epoxide or lactone.

ENUMERATED EMBODIMENTS

The following enumerated embodiments are representative of some aspects of the invention.

1. A system for the production of chemicals, comprising:

a central reactor, comprising an inlet fed by an epoxide source and a carbon monoxide (CO) source, a central reaction zone that converts at least some of the epoxide to a beta lactone, and an outlet which provides an outlet stream comprising the beta lactone, two or more of:

(i) a first $C_3$ reactor, comprising an inlet fed by the outlet stream comprising beta lactone of the central reactor, a first $C_3$ reaction zone that converts at least some of the beta lactone to a first $C_3$ product, and an outlet which provides an outlet stream comprising the first $C_3$ product, (ii) a second $C_3$ reactor, comprising an inlet fed by the outlet stream comprising beta lactone of the central reactor, a second $C_3$ reaction zone that converts at least some of the beta lactone to a second $C_3$ product, and an outlet which provides an outlet stream comprising the second $C_3$ product, and (iii) a first $C_4$ reactor, comprising an inlet fed by the outlet stream comprising beta lactone of the central reactor, a first $C_4$ reaction zone that converts at least some of the beta lactone to a first $C_4$ product, and an outlet which provides an outlet stream comprising the first $C_4$ product, and a controller for independently modulating production of the beta lactone and each of the products, with the provision that the first $C_3$ product differs from the second $C_3$ product.

2. The system of embodiment 1, comprising the first $C_3$ reactor and the second $C_3$ reactor.

3. The system of embodiment 1, comprising the first $C_3$ reactor and the first $C_4$ reactor.

4. The system of embodiment 1, wherein the epoxide is ethylene oxide (EO) and the beta lactone is beta propiolactone (BPL).

5. The system of embodiment 4, further comprising an oxidative reactor, comprising an inlet fed by ethylene, an oxidative reaction zone that converts at least some of the ethylene to EO, and an outlet which provides an outlet stream comprising the EO, which is fed to the inlet of the central reactor.

6. The system of embodiment 1, wherein the first $C_3$ product and the second $C_3$ product are independently selected from an $\alpha,\beta$-unsaturated acid, an $\alpha,\beta$-unsaturated ester, an $\alpha,\beta$-unsaturated amide, a polymer and 1,3-propanediol (PDO).

7. The system of embodiment 6, wherein the first $C_3$ product is polypropiolactone (PPL).

8. The system of embodiment 6, wherein the first $C_3$ product is acrylic acid.

9. The system of embodiment 1, wherein the first $C_3$ product is PPL, and the system further comprises a third $C_3$ reactor, comprising an inlet fed by the outlet stream comprising PPL of the first $C_3$ reactor, a third $C_3$ reaction zone that converts at least some of the PPL to a third $C_3$ product, and an outlet which provides an outlet stream comprising the third $C_3$ product.

10. The system of embodiment 1, wherein the third $C_3$ product is acrylic acid.

11. The system of embodiment 1, wherein the first $C_4$ product is succinic anhydride.

12. The system of embodiment 1, wherein the first $C_4$ product is succinic anhydride, and the system further comprises a second $C_4$ reactor, comprising an inlet fed by the outlet stream comprising succinic anhydride of the first $C_4$ reactor, a second $C_4$ reaction zone that converts at least some of the succinic anhydride to a second $C_4$ product, and an outlet which provides an outlet stream comprising the second $C_4$ product.

13. The system of embodiment 12, wherein the second $C_4$ product is succinic acid, 1,4 butanediol (BDO), tetrahydrofuran (THF) or gamma butyrolactone (GBL).

14. A system for the production of acrylic acid (AA), wherein the system produces AA at about 200 to about 800 kilotons per annum (kta).

15. The system of embodiment 14, wherein the system produces the AA from ethylene.

16. The system of embodiment 15, comprising:
an oxidative reactor, comprising an inlet fed by ethylene, an oxidative reaction zone that converts at least some of the ethylene to ethylene oxide (EO), and an outlet which provides an outlet stream comprising the EO, which is fed to an inlet of a central reactor,
the central reactor, comprising the inlet fed by the outlet stream comprising the EO from the oxidative reactor and a carbon monoxide (CO) source, a central reaction zone that converts at least some of the EO to beta propiolactone (BPL), and an outlet which provides an outlet stream comprising the BPL, one or more of:
(i) a first $C_3$ reactor, comprising an inlet fed by the outlet stream comprising BPL of the central reactor, a first $C_3$ reaction zone that converts at least some of the BPL to a polypropiolactone (PPL), and an outlet which provides an outlet stream comprising the PPL, and a third $C_3$ reactor, comprising an inlet fed by the outlet stream comprising PPL of the first $C_3$ reactor, a third $C_3$ reaction zone that converts at least some of the PPL to AA, and an outlet which provides an outlet stream comprising the AA, and
(iii) a second $C_3$ reactor, comprising an inlet fed by the outlet stream comprising BPL of the central reactor, a second $C_3$ reaction zone that converts at least some of the BPL to AA, and an outlet which provides an outlet stream comprising the AA, and
a controller for independently modulating production of the EO, BPL, AA and, optionally, PPL and any products.

17. The system of embodiment 16, further comprising one or more of:
(iv) a fourth $C_3$ reactor, comprising an inlet fed by the outlet stream comprising BPL of the central reactor, a fourth $C_3$ reaction zone that converts at least some of the BPL to a $C_3$ product other than acrylic acid, and an outlet which provides an outlet stream comprising the $C_3$ product other than acrylic acid, and
(v) a first $C_4$ reactor, comprising an inlet fed by the outlet stream comprising BPL of the central reactor, a first $C_4$ reaction zone that converts at least some of the BPL to a first $C_4$ product, and an outlet which provides an outlet stream comprising the first $C_4$ product.

18. A method, wherein the method is for the conversion of an epoxide to two or more of: a first $C_3$ product, a second $C_3$ product, and a first $C_4$ product within an integrated system, the method comprising:
providing an inlet stream comprising an epoxide and carbon monoxide (CO) to a central reactor of the integrated system;
contacting the inlet stream with a carbonylation catalyst in a central reaction zone to effect conversion of at least a portion of the provided epoxide to a beta lactone;
directing an outlet stream comprising beta lactone from the central reaction zone to two or more of:
(i) a first $C_3$ reactor, comprising an inlet fed by the outlet stream comprising beta lactone of the central reactor, a first $C_3$ reaction zone that converts at least some of the beta lactone to a first $C_3$ product, and an outlet from which an outlet stream comprising the first $C_3$ product is obtainable,
(ii) a second $C_3$ reactor, comprising an inlet fed by the outlet stream comprising beta lactone of the central reactor, a second $C_3$ reaction zone that converts at least some of the beta lactone to a second $C_3$ product, and an outlet from which an outlet stream comprising the second $C_3$ product is obtainable, and
(iii) a first $C_4$ reactor, comprising an inlet fed by the outlet stream comprising beta lactone of the central reactor, a first $C_4$ reaction zone that converts at least some of the beta lactone to a first $C_4$ product, and an outlet from which an outlet stream comprising the first $C_4$ product is obtainable, and
obtaining two or more of the first $C_3$ product, the second $C_3$ product, and the first $C_4$ product.

19. The method of embodiment 18, further comprising:
providing an inlet stream comprising ethylene to an inlet of an oxidative reactor in which at least some of the ethylene is converted to ethylene oxide (EO), and
providing an outlet stream comprising EO from the oxidative reactor, to the inlet of the central reactor in which at least some of the EO is converted to BPL.

20. The method of embodiment 18, comprising directing the outlet stream comprising beta lactone from the central reaction zone to the first $C_3$ reactor and the second $C_3$ reactor.

21. The method of embodiment 18, comprising directing the outlet stream comprising beta lactone from the central reaction zone to the first $C_3$ reactor and the first $C_4$ reactor.

22. The method of embodiment 18, wherein the epoxide is ethylene oxide (EU) and the beta lactone is beta propiolactone (BPL).

23. The method of embodiment 18, wherein the first $C_3$ product and the second $C_3$ product are independently selected from an α,β-unsaturated acid, an α,β-unsaturated ester, an α,β-unsaturated amide, a $C_3$ polymer and 1,3-propanediol (PDO).

24. The method of embodiment 18, wherein the first $C_3$ product is polypropiolactone (PPL).

25. The method of embodiment 18, wherein the first $C_3$ product is acrylic acid.

26. The method of embodiment 24, further comprising:
directing the an outlet stream comprising PPL from the first $C_3$ reactor to a third $C_3$ reactor, comprising an inlet fed by the outlet stream comprising PPL of the first $C_3$ reactor, a third $C_3$ reaction zone that converts at least some of the PPL to a third $C_3$ product, and an outlet from which an outlet stream comprising the third $C_3$ product is obtainable.

27. The method of enumerated 26, wherein the third $C_3$ product is acrylic acid.

28. The method of embodiment 18, wherein the first $C_4$ product is succinic anhydride.

29. The method of embodiment 18, wherein the first $C_4$ product is succinic anhydride, and the system further comprises a second $C_4$ reactor, comprising an inlet fed by the outlet stream comprising succinic anhydride of the first $C_4$ reactor, a second $C_4$ reaction zone that converts at least some of the succinic anhydride to a second $C_4$ product, and an outlet from which an outlet stream comprising the second $C_4$ product is obtainable.

30. The method of embodiment 29, wherein the second $C_4$ product is succinic acid, 1,4 butanediol (BDO), tetrahydrofuran (THF) or gamma butyrolactone (GBL).

31. A method, wherein the method is for the production of acrylic acid (AA) from ethylene in a single integrated system, the method comprising:

providing ethylene to an oxidative reactor that converts at least some of the ethylene to ethylene oxide (EO), providing EO to a central reactor that converts at least some of the EO to beta propiolactone (BPL), and at least one of:

providing BPL to a first reactor that converts at least some of the BPL to AA, and providing BPL to a reactor that converts at least some of the BPL to polypropiolactone (PPL), and isolating acrylic acid at a rate of about 200 to about 800 kilotons per annum (kta).

32. A system for the production of $C_3$ and $C_4$ products, comprising:
an epoxide source;
a carbon monoxide (CO) source;
a central reactor, comprising:
an inlet configured to receive epoxide from the epoxide source and CO from the CO source,
a central reaction zone configured to convert at least some of the epoxide to a beta lactone, and
an outlet configured to provide an outlet stream comprising the beta lactone,
two or more of (i)-(iii):
(i) a first $C_3$ reactor, comprising:
an inlet configured to receive the outlet stream comprising beta lactone of the central reactor,
a first $C_3$ reaction zone configured to convert at least some of the beta lactone to a first $C_3$ product, and
an outlet configured to provide an outlet stream comprising the first $C_3$ product,
(ii) a second $C_3$ reactor, comprising:
an inlet configured to receive the outlet stream comprising beta lactone of the central reactor,
a second $C_3$ reaction zone configured to convert at least some of the beta lactone to a second $C_3$ product, and
an outlet configured to provide an outlet stream comprising the second $C_3$ product, and
(iii) a first $C_4$ reactor, comprising:
an inlet configured to receive the outlet stream comprising beta lactone of the central reactor,
a first $C_4$ reaction zone configured to convert at least some of the beta lactone to a first $C_4$ product, and
an outlet configured to provide an outlet stream comprising the first $C_4$ product, and
a controller to independently modulate production of the beta lactone and each of the products,
provided that the first $C_3$ product differs from the second $C_3$ product.

33. The system of embodiment 32, wherein the two or more of (i)-(iii) is (i) the first $C_3$ reactor and (ii) the second $C_3$ reactor.

34. The system of embodiment 32, wherein the two or more (i)-(iii) is (i) the first $C_3$ reactor and (iii) the first $C_4$ reactor.

35. The system of any one of embodiments 32 to 34, wherein the epoxide is ethylene oxide (EO) and the beta lactone is beta propiolactone (BPL).

36. The system of embodiment 35, further comprising;
an ethylene source;
an oxidative reactor comprising:
an inlet configured to receive ethylene,
an oxidative reaction zone configured to convert at least some of the ethylene to EO, and
an outlet configured to provide an outlet stream comprising the EO, and feed the outlet stream comprising EO to the inlet of the central reactor.

37. The system of any one of embodiments 32 to 36, wherein the first $C_3$ product and the second $C_3$ product are independently selected from an α,β-unsaturated acid, an α,β-unsaturated ester, an α,β-unsaturated amide, a polymer and 1,3-propanediol (PDO).

38. The system of embodiment 37, wherein the first $C_3$ product is polypropiolactone (PPL).

39. The system of embodiment 37, wherein the first $C_3$ product is acrylic acid.

40. The system of any one of embodiments 32 to 38, wherein the first $C_3$ product is PPL, and the system further comprises:
a third $C_3$ reactor comprising:
an inlet configured to receive the outlet stream comprising PPL of the first $C_3$ reactor,
a third $C_3$ reaction zone configured to convert at least some of the PPL to a third $C_3$ product, and
an outlet configured to provide an outlet stream comprising the third $C_3$ product.

41. The system of embodiment 40, wherein the third $C_3$ product is acrylic acid (AA).

42. The system of embodiment 41, wherein the system is configured to produce AA at about 200 to about 800 kilotons per annum (kta).

43. The system of any one of embodiments 32 to 42, wherein the first $C_4$ product is succinic anhydride.

44. The system of any one of embodiments 32 to 42, wherein the first $C_4$ product is succinic anhydride, and the system further comprises:
a second $C_4$ reactor comprising:
an inlet configured to receive the outlet stream comprising succinic anhydride of the first $C_4$ reactor,
a second $C_4$ reaction zone configured to convert at least some of the succinic anhydride to a second $C_4$ product, and
an outlet configured to provide an outlet stream comprising the second $C_4$ product.

45. The system of embodiment 44, wherein the second $C_4$ product is succinic acid, 1,4 butanediol (BDO), tetrahydrofuran (THF) or gamma butyrolactone (GBL).

46. A system, comprising:
an ethylene source;
a carbon monoxide (CO) source;
an alcohol source;
an oxidative reactor comprising:
an inlet configured to receive ethylene from the ethylene source,
an oxidative reaction zone configured to convert at least some of the ethylene to ethylene oxide (EO), and
an outlet configured to provide an EO stream comprising the EO;
a central reactor comprising:
an inlet configured to receive EO from the EO stream of the oxidative reactor and CO from the CO source,
a central reaction zone configured to convert at least some of the EO to beta propiolactone (BPL), and
an outlet configured to provide a BPL stream comprising the BPL;
a first C3 reactor comprising:
an inlet configured to receive BPL from at least a portion of the BPL stream of the central reactor,
a first C3 reaction zone configured to convert at least some of the BPL to a polypropiolactone (PPL), and
an outlet configured to provide a PPL stream comprising the PPL;
a second C3 reactor comprising;
an inlet configured to receive PPL from the PPL stream of the first C3 reactor,
a second C3 reaction zone configured to convert at least some of the PPL to AA, and an outlet configured to provide an AA stream comprising the AA;
a third C3 reactor comprising:
an inlet configured to receive BPL from at least a portion of the BPL stream of the central reactor, and an alcohol from the alcohol source,
a third C3 reaction zone configured to convert at least some of the BPL to acrylate esters, and
an outlet configured to provide an acrylate ester stream comprising the acrylate esters; and
a controller to independently modulating production of the EO, BPL, PPL, AA, and acrylate esters.

47. The system of embodiment 46, wherein the system simultaneously produces the PPL stream, the AA stream, and the acrylate ester stream.

48. The system embodiment 46 or 47, wherein the controller modulates a ratio of PPL:AA:acrylate ester from the PPL stream, the AA stream, and the acrylate ester stream.

49. The system of any one of embodiments 46 to 47, wherein the inlet of the second C3 reactor is configured to receive PPL from a fraction of the PPL stream of the first C3 reactor, and wherein the controller modulates the fraction of the PPL output stream that is received by the inlet of the second C3 reactor.

50. The system of any one of embodiments 46 to 49, further comprising:
a PPL isolation unit comprising:
a PPL processing unit;
a PPL packaging unit; and
a PPL outlet configured to provide packaged PPL for distribution.

51. A system, comprising:
an ethylene source;
a carbon monoxide (CO) source;
an alcohol source;
an oxidative reactor comprising:
an inlet configured to receive ethylene from the ethylene source,
an oxidative reaction zone configured to convert at least some of the ethylene to ethylene oxide (EO), and
an outlet configured to provide an EO stream comprising the EO;
a central reactor comprising:
an inlet configured to receive EO from the EO stream of the oxidative reactor and CO from the CO source,
a central reaction zone configured to convert at least some of the EO to beta propiolactone (BPL), and
an outlet configured to provide a BPL stream comprising the BPL;
a first C3 reactor comprising:
an inlet configured to receive BPL from at least a portion of the BPL stream of the central reactor,
a first C3 reaction zone configured to convert at least some of the BPL to a polypropiolactone (PPL), and
an outlet configured to provide a PPL stream comprising the PPL;
a second C3 reactor comprising;
an inlet configured to receive BPL from at least a portion of the BPL stream of the central reactor,
a second C3 reaction zone configured to convert at least some of the BPL to AA, and
an outlet configured to provide an AA stream comprising the AA;
a third C3 reactor comprising:
an inlet configured to receive BPL from at least a portion of the BPL stream of the central reactor, and an alcohol from the alcohol source,
a third C3 reaction zone configured to convert at least some of the BPL to acrylate esters, and
an outlet configured to provide an acrylate ester stream comprising the acrylate esters; and
a controller to independently modulating production of the EU, BPL, PPL, AA, and acrylate esters.

52. The system of embodiment 51, wherein the system simultaneously produces two or more of the PPL stream, the AA stream, and the acrylate ester stream 53. The system of embodiment 51, wherein the system simultaneously produces the PPL stream, the AA stream, and the acrylate ester stream.

54. The system of any one of embodiments 51 to 53, wherein the controller modulates a ratio of PPL:AA:acrylate ester from the PPL stream, the AA stream, and the acrylate ester stream.

55. A system, comprising:
an ethylene source;
a carbon monoxide (CO) source;
an oxidative reactor comprising:
an inlet configured to receive ethylene from the ethylene source,
an oxidative reaction zone configured to convert at least some of the ethylene to ethylene oxide (EO), and
an outlet configured to provide an EU stream comprising the EU;
a central reactor comprising:
an inlet configured to receive EU from the EU stream of the oxidative reactor and CO from the CO source,
a central reaction zone configured to convert at least some of the EO to beta propiolactone (BPL), and
an outlet configured to provide a BPL stream comprising the BPL;
a first C3 reactor comprising:
an inlet configured to receive BPL from at least a portion of the BPL stream of the central reactor,
a first C3 reaction zone configured to convert at least some of the BPL to a polypropiolactone (PPL), and
an outlet configured to provide a PPL stream comprising the PPL;
a second C3 reactor comprising;
an inlet configured to receive PPL from the PPL stream of the first C3 reactor,
a second C3 reaction zone configured to convert at least some of the PPL to AA, and
an outlet configured to provide an AA stream comprising the AA;
a first C4 reactor comprising:
an inlet configured to receive BPL from at least a portion of the BPL stream of the central reactor, and carbon monoxide from the CO source,
a first C4 reaction zone configured to convert at least some of the BPL to succinic anhydride (SA), and
an outlet configured to provide a succinic anhydride stream comprising the succinic anhydride; and
a controller to independently modulating production of the EO, BPL, PPL, AA, and SA.

56. The system embodiment 55, wherein the system simultaneously produces the PPL stream, the AA stream, and the SA stream.

57. The system of embodiment 55 or 56, wherein the controller modulates a ratio of PPL:AA:SA from the PPL stream, the AA stream, and the SA stream.

58. The system of any one of embodiments 55 to 57, wherein the inlet of the second C3 reactor is configured to receive PPL from a fraction of the PPL stream of the first C3 reactor, and wherein the controller modulates the fraction of the PPL stream that is received by the inlet of the second C3 reactor.

59. The system of any one of embodiments 55 to 58, further comprising:
a PPL isolation unit comprising:
a PPL processing unit,
a PPL packaging unit, and
a PPL outlet configured to provide packaged PPL for distribution.

60. The system of any one of embodiments 55 to 59, further comprising:
a hydrogen source; and
a second C4 reactor comprising:
an inlet configured to receive SA from the SA stream of the first C4 reactor,
a hydrogen inlet fed from the hydrogen source,
a second C4 reaction zone configured to hydrogenate at least a portion of the SA to provide a C4 product stream comprising 1,4 butanediol (BDO), tetrahydrofuran (THF), or gamma butyrolactone (GBL), or any combinations thereof.

61. The system of embodiment 60, wherein the controller is configured to further modulate production of BDO, THF, and GBL.

62. A system, comprising:
an ethylene source;
a carbon monoxide (CO) source;
an alcohol source;
an oxidative reactor comprising:
an inlet configured to receive ethylene from the ethylene source,
an oxidative reaction zone configured to convert at least some of the ethylene to ethylene oxide (EO), and
an outlet configured to provide an EO stream comprising the EO,
a central reactor comprising:
an inlet configured to receive EO from the EO stream of the oxidative reactor and at least a portion of CO from the CO source,
a central reaction zone configured to convert at least some of the EO to beta propiolactone (BPL), and
an outlet configured to provide a BPL stream comprising the BPL;
a first C3 reactor comprising:
an inlet configured to receive BPL from at least a portion of the BPL stream of the central reactor,
a first C3 reaction zone configured to convert at least some of the BPL to a polypropiolactone (PPL), and
an outlet configured to provide a PPL stream comprising the PPL;
a second C3 reactor comprising:
an inlet configured to receive BPL from the BPL stream of the central reactor,
a second C3 reaction zone configured to convert at least some of the BPL to AA, and
an outlet configured to provide an AA stream comprising the AA;
a third C3 reactor comprising:
an inlet configured to receive BPL from at least a portion of the BPL stream of the central reactor, and an alcohol from the alcohol source,
a third C3 reaction zone configured to convert at least some of the BPL to acrylate esters, and
an outlet configured to provide an acrylate ester stream comprising the acrylate esters;
a first C4 reactor comprising:
an inlet configured to receive BPL from at least a portion of the BPL stream of the central reactor, and at least a portion of CO from the CO source,
a first C4 reaction zone configured to convert at least some of the BPL to succinic anhydride (SA), and
an outlet configured to provide a SA stream comprising the succinic anhydride; and
a controller to independently modulating production of the EO, BPL, PPL, AA, acrylate esters, and SA.

63. The system of embodiment 62, wherein the system simultaneously produces the PPL stream, the AA stream, and the acrylate ester stream.

64. The system of embodiment 62, wherein the system simultaneously produces the PPL stream, the AA stream, the acrylate ester stream, and the SA stream.

65. The system of any one of embodiments 62 to 64, wherein the controller modulates a ratio PPL:AA:acrylate ester from the PPL stream, the AA stream, and the acrylate ester stream.

66. The system of any one of embodiments 62 to 65, wherein the controller modulates a ratio PPL:AA:acrylate ester:SA from the PPL stream, the AA stream, the acrylate ester stream, and the SA stream.

67. The system of any one of embodiments 62 to 66, wherein the inlet of the second C3 reactor is configured to receive PPL from a fraction of the PPL stream of the first C3 reactor, and wherein the controller modulates the fraction of the PPL stream that is fed to the second C3 reactor.

68. The system of any one of embodiments 62 to 67, further comprising:
a hydrogen source;
a second C4 reactor comprising:
at least one inlet configured to receive SA from the SA stream of the first C4 reactor, and hydrogen from the hydrogen source,
a second C4 reaction zone configured to hydrogenate at least a portion of the SA to provide a C4 product stream comprising 1,4 butanediol (BDO), tetrahydrofuran (THF), or gamma butyrolactone (GBL), or any combinations thereof.

69. The system of embodiment 68, wherein the controller is configured to further modulate production of BDO, THF, and GBL.

70. A method for converting an epoxide to two or more of: a first $C_3$ product, a second $C_3$ product, and a first $C_4$ product within an integrated system, the method comprising:
providing an inlet stream comprising an epoxide and carbon monoxide (CO) to a central reactor of the integrated system;
contacting the inlet stream with a carbonylation catalyst in a central reaction zone;
converting at least a portion of the epoxide to a beta lactone to produce an outlet stream comprising beta lactone;
(i) directing the outlet stream comprising beta lactone from the central reaction zone to a first $C_3$ reactor, and converting at least some of the beta lactone to a first $C_3$ product in the first $C_3$ reactor to produce an outlet stream comprising the first $C_3$ product, or
(ii) directing the outlet stream comprising beta lactone from the central reaction zone to a second $C_3$ reactor, and converting at least some of the beta lactone to a second $C_3$ product in the second $C_3$ reactor to produce an outlet stream comprising the second $C_3$ product, or
(iii) directing the outlet stream comprising beta lactone from the central reaction zone to a first $C_4$ reactor, and converting at least some of the beta lactone to a first $C_4$ product in the first $C_4$ reactor to produce an outlet stream comprising the first $C_4$ product, provided that at least two of (i)-(iii) are selected; and
obtaining two or more of the first $C_3$ product, the second $C_3$ product, and the first $C_4$ product.

71. The method of embodiment 70, further comprising:
providing an inlet stream comprising ethylene to an inlet of an oxidative reactor;
converting at least some of the ethylene to ethylene oxide (EO) to produce an outlet stream comprising EO;
directing the outlet stream comprising EO from the oxidative reactor to the inlet of the central reactor; and
converting at least some of the EO to BPL.

72. The method of embodiment 70 or 71, wherein the outlet stream comprising beta lactone is directed from the central reaction zone to the first $C_3$ reactor and the second $C_3$ reactor.

73. The method of embodiment 70 or 71, wherein the outlet stream comprising beta lactone is directed from the central reaction zone to the first $C_3$ reactor and the first $C_4$ reactor.

74. The method of any one of embodiments 70 to 73, wherein the epoxide is ethylene oxide (EO) and the beta lactone is beta propiolactone (BPL).

75. The method of any one of embodiments 70 to 74, wherein the first $C_3$ product and the second $C_3$ product are independently selected from an α,β-unsaturated acid, an α,β-unsaturated ester, an α,β-unsaturated amide, a $C_3$ polymer and 1,3-propanediol (PDO).

76. The method of any one of embodiments 70 to 74, wherein the first $C_3$ product is polypropiolactone (PPL).

77. The method of any one of embodiments 70 to 74, wherein the first $C_3$ product is acrylic acid.

78. The method of embodiment 77, further comprising:
directing the outlet stream comprising PPL from the first $C_3$ reactor to a third $C_3$ reactor;
converting at least some of the PPL to a third $C_3$ product in the third $C_3$ reactor to produce an outlet stream comprising the third $C_3$ product.

79. The method of embodiment 78, wherein the third $C_3$ product is acrylic acid.

80. The method of any one of embodiments 70 to 79, wherein the first $C_4$ product is succinic anhydride.

81. The method of any one of embodiments 70 to 79, wherein the first $C_4$ product is succinic anhydride, and the method further comprises:
directing the outlet stream comprising succinic anhydride from the first $C_4$ reactor to a second $C_4$ reactor;
converting at least some of the succinic anhydride to a second $C_4$ product in the second $C_4$ reactor to produce an outlet stream comprising the second $C_4$ product.

82. The method of embodiment 81, wherein the second $C_4$ product is succinic acid, 1,4 butanediol (BDO), tetrahydrofuran (THF) or gamma butyrolactone (GBL).

83. A method for producing acrylic acid (AA) from ethylene in a single integrated system, the method comprising:
providing ethylene to an oxidative reactor that converts at least some of the ethylene to ethylene oxide (EO);
providing EO to a central reactor that converts at least some of the EO to beta propiolactone (BPL);
and at least one or both of (i) and (ii):
(i) providing BPL to a first reactor that converts at least some of the BPL to
AA, and
(ii) providing BPL to a reactor that converts at least some of the BPL to polypropiolactone (PPL).

84. The method of embodiment 83, wherein BPL is provided to a first reactor that converts at least some of the BPL, and the method further comprises isolating acrylic acid at a rate of about 200 to about 800 kilotons per annum (kta).

85. A method, comprising:
providing an EO stream and a CO stream to a central reactor, wherein the EO stream comprises EO, and the CO stream comprises CO;
contacting the EO stream and the CO stream with a carbonylation catalyst in the central reactor;
converting at least a portion of the EO to produce a beta propiolactone (BPL) stream comprising BPL;
directing at least a portion of the BPL stream to a first C3 reactor;
converting at least portion of the BPL to polypropiolactone (PPL) in the first C3 reactor, to produce a PPL stream comprising the PPL from the first C3 reactor;
directing the PPL stream to a second C3 reactor;
converting at least a portion of the PPL to acrylic acid (AA) in the second C3 reactor, to produce an AA stream comprising the AA from the second C3 reactor;
directing at least a portion of the BPL stream to a third C3 reactor;
contacting the BPL stream in the third C3 reactor with an alcohol; and
converting at least a portion of the BPL to acrylate esters in the third C3 reactor, to produce an acrylate ester stream comprising the acrylate esters.

86. The method of embodiment 85, the PPL stream, the AA stream, and the acrylate ester stream are simultaneously produced.

87. The method embodiment 85 or 86, further comprising modulating a ratio of PPL:AA:acrylate ester produced in the PPL stream, the AA stream, and the acrylate ester stream.

88. The method of any one of embodiments 85 to 87, further comprising modulating the fraction of the PPL stream that is received by the second C3 reactor.

89. A method, comprising:
providing an EO stream and a CO stream to a central reactor, wherein the EO stream comprises EO, and the CO stream comprises CO;
contacting the EO stream and the CO stream with a carbonylation catalyst in the central reactor;
converting at least a portion of the EO to produce a beta propiolactone (BPL) stream comprising BPL;
directing at least a portion of the BPL stream to a first C3 reactor;
converting at least portion of the BPL to polypropiolactone (PPL) in the first C3 reactor, to produce a PPL stream comprising the PPL from the first C3 reactor;
directing at least a portion of the BPL stream to a second C3 reactor;
converting at least a portion of the BPL to acrylic acid (AA) in the second C3 reactor, to produce an AA stream comprising the AA from the second C3 reactor;
directing at least a portion of the BPL stream to a third C3 reactor;
contacting the BPL stream with an alcohol in the third C3 reactor; and
converting at least a portion of the BPL to acrylate esters in the third C3 reactor, to produce an acrylate ester stream comprising the acrylate esters.

90. The method of embodiment 89, wherein two or more of the PPL stream, the AA stream, and the acrylate ester stream are simultaneously produced.

91. The method of embodiment 89, wherein the PPL stream, the AA stream, and the acrylate ester stream are simultaneously produced.

92. The method of any one of embodiments 89 to 91, further comprising modulating a ratio of PPL:AA:acrylate ester produced in the PPL stream, the AA stream, and the acrylate ester stream.

93. A method, comprising:
providing an EU stream and a CO stream to a central reactor, wherein the EO stream comprises EO, and the CO stream comprises CO;
contacting the EO stream and the CO stream with a carbonylation catalyst in the central reactor;
converting at least a portion of the EO to produce a beta propiolactone (BPL) stream comprising BPL;
directing at least a portion of the BPL stream to a first C3 reactor;
converting at least portion of the BPL to polypropiolactone (PPL) in the first C3 reactor, to produce a PPL stream comprising the PPL from the first C3 reactor;
directing the PPL stream to a second C3 reactor;
converting at least some of the PPL to acrylic acid (AA) in the second C3 reactor, to produce an AA stream comprising the AA from the second C3 reactor;
directing at least a portion of the BPL stream to a first C4 reactor; and
converting at least some of the BPL to succinic anhydride (SA) in the first C4 reactor, to produce a succinic anhydride stream comprising the succinic anhydride from the first C4 reactor.

94. The method of embodiment 93, wherein the PPL stream, the AA stream, and the SA stream are simultaneously produced.

95. The method of embodiment 93 or 94, further comprising modulating a ratio of PPL:AA:SA from the PPL stream, the AA stream, and the SA stream.

96. The method of any one of embodiments 93 to 95, further comprising modulating the fraction of the PPL stream that is received by the second C3 reactor.

97. The method of any one of embodiments 93 to 96, further comprising:
directing the SA stream to a second C4 reactor;
contacting at the SA stream with hydrogen in the second C4 reactor; and
converting at least a portion of the SA to 1,4 butanediol (BDO), tetrahydrofuran (THF), or gamma butyrolactone (GBL), or any combinations thereof.

98. The method of embodiment 97, further comprising modulating a ratio of BDO:THF:GBL produced in the second C4 reactor.

99. A method, comprising:
providing an EO stream and a CO stream to a central reactor, wherein the EO stream comprises EO, and the CO stream comprises CO;
contacting the EO stream and at least a portion of the CO stream with a carbonylation catalyst in the central reactor;
converting at least a portion of the EO to produce a beta propiolactone (BPL) stream comprising BPL;
directing at least a portion of the BPL stream to a first C3 reactor;
converting at least portion of the BPL to polypropiolactone (PPL) in the first C3 reactor, to produce a PPL stream comprising the PPL from the first C3 reactor;
directing at least a portion of the BPL stream to a second C3 reactor;
converting at least a portion of the BPL to acrylic acid (AA) in the second C3 reactor, to produce an AA stream comprising the AA from the second C3 reactor;
directing at least a portion of the BPL stream to a third C3 reactor;
contacting the BPL stream with an alcohol in the third C3 reactor;
converting at least a portion of the BPL to acrylate esters in the C3 reactor, to produce an acrylate ester stream comprising the acrylate esters;
directing at least a portion of the BPL stream to a first C4 reactor;
contacting the BPL stream and at least a portion of the CO stream in the first C4 reactor; and
converting at least a portion of the BPL to succinic anhydride (SA) in the first C4 reactor, to produce a SA stream comprising the SA.

100. The method of embodiment 99, wherein the PPL stream, the AA stream, and the acrylate ester stream are simultaneously produced.

101. The method of embodiment 99, wherein the PPL stream, the AA stream, the acrylate ester stream, and the SA stream are simultaneously produced.

102. The method of any one of embodiments 99 to 101, further comprising modulating a ratio PPL:AA:acrylate ester from the PPL stream, the AA stream, and the acrylate ester stream.

103. The method of any one of embodiments 99 to 102, further comprising modulating a ratio PPL:AA:acrylate ester output:SA from the PPL stream, the AA stream, the acrylate ester stream, and the SA stream.

104. The method of any one of embodiments 99 to 103, further comprising modulating the fraction of the BPL stream that is received by the second C3 reactor.

105. The method of any one of embodiments 99 to 104, further comprising:
directing the SA stream to a second C4 reactor;
contacting at the SA stream with hydrogen in the second C4 reactor; and
converting at least a portion of the SA to 1,4 butanediol (BDO), tetrahydrofuran (THF), or gamma butyrolactone (GBL), or any combinations thereof.

106. The method of embodiment 105, further comprising modulating a ratio of BDO:THF:GBL produced in the second C4 reactor.

107. The method of any one of embodiments 85 to 106, further comprising:
providing an ethylene stream to an oxidative reactor, wherein the ethylene stream comprises ethylene; and
converting at least a portion of the ethylene to ethylene oxide (EO), and providing the EO stream.

108. The method of any one of embodiments 85 to 107, further comprising:
isolating PPL from the PPL stream; and
packaging the isolated PPL for distribution.

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for converting an epoxide to two or more of: a first $C_3$ product, a second $C_3$ product, and a first $C_4$ product within an integrated system, the method comprising:
providing an inlet stream comprising an epoxide and carbon monoxide (CO) to a central reactor of the integrated system;
contacting the inlet stream with a carbonylation catalyst in a central reaction zone;

converting at least a portion of the epoxide to a beta lactone to produce an outlet stream comprising beta lactone;
(i) directing the outlet stream comprising beta lactone from the central reaction zone to a first $C_3$ reactor, and converting at least some of the beta lactone to a first $C_3$ product in the first $C_3$ reactor to produce an outlet stream comprising the first $C_3$ product, or
(ii) directing the outlet stream comprising beta lactone from the central reaction zone to a second $C_3$ reactor, and converting at least some of the beta lactone to a second $C_3$ product in the second $C_3$ reactor to produce an outlet stream comprising the second $C_3$ product, and
(iii) directing the outlet stream comprising beta lactone from the central reaction zone to a first $C_4$ reactor, and converting at least some of the beta lactone to a first $C_4$ product in the first $C_4$ reactor to produce an outlet stream comprising the first $C_4$ product; and
obtaining the first $C_3$ product, the second $C_3$ product, and the first $C_4$ product.

2. A method for producing acrylic acid (AA) from ethylene in a single integrated system, the method comprising:
providing ethylene to an oxidative reactor that converts at least some of the ethylene to ethylene oxide (EO);
providing EO to a central reactor that converts at least some of the EO to beta propiolactone (BPL);
providing BPL to a first reactor that converts at least some of the BPL to AA, and
providing BPL to a second reactor that converts at least some of the BPL to polypropiolactone (PPL).

3. The method of claim 2, wherein BPL is provided to a first reactor that converts at least some of the BPL, and the method further comprises isolating acrylic acid at a rate of about 200 to about 800 kilotons per annum (kta).

4. A method, comprising:
providing an EO stream and a CO stream to a central reactor, wherein the EO stream comprises EO, and the CO stream comprises CO;
contacting the EO stream and the CO stream with a carbonylation catalyst in the central reactor;
converting at least a portion of the EO to produce a beta propiolactone (BPL) stream comprising BPL;
directing at least a portion of the BPL stream to a first C3 reactor;
converting at least portion of the BPL to polypropiolactone (PPL) in the first C3 reactor, to produce a PPL stream comprising the PPL from the first C3 reactor;
directing the PPL stream to a second C3 reactor;
converting at least a portion of the PPL to acrylic acid (AA) in the second C3 reactor, to produce an AA stream comprising the AA from the second C3 reactor;
directing at least a portion of the BPL stream to a third C3 reactor;
contacting the BPL stream in the third C3 reactor with an alcohol; and
converting at least a portion of the BPL to acrylate esters in the third C3 reactor, to produce an acrylate ester stream comprising the acrylate esters.

5. The method of claim 4, further comprising:
directing at least a portion of the BPL stream to a fourth C3 reactor;
converting at least a portion of the BPL to acrylic acid (AA) in the fourth C3 reactor, to produce an AA stream comprising the AA from the fourth C3 reactor;
directing at least a portion of the BPL stream to a fifth C3 reactor;
contacting the BPL stream with an alcohol in the fifth C3 reactor; and
converting at least a portion of the BPL to acrylate esters in the fifth C3 reactor, to produce another acrylate ester stream comprising the acrylate esters.

6. The method of claim 4, further comprising:
directing at least a portion of the BPL stream to a first C4 reactor; and
converting at least some of the BPL to succinic anhydride (SA) in the first C4 reactor, to produce a succinic anhydride stream comprising the succinic anhydride from the first C4 reactor.

7. The method of claim 4, further comprising:
directing at least a portion of the BPL stream to a fourth C3 reactor;
contacting the BPL stream with an alcohol in the fourth C3 reactor;
converting at least a portion of the BPL to acrylate esters in the fourth C3 reactor, to produce another acrylate ester stream comprising the acrylate esters;
directing at least a portion of the BPL stream to a first C4 reactor;
contacting the BPL stream and at least a portion of the CO stream in the first C4 reactor; and
converting at least a portion of the BPL to succinic anhydride (SA) in the first C4 reactor, to produce a SA stream comprising the SA.

8. The method of claim 6, further comprising:
directing the SA stream to a second C4 reactor;
contacting at the SA stream with hydrogen in the second C4 reactor; and
converting at least a portion of the SA to 1,4 butanediol (BDO), tetrahydrofuran (THF), or gamma butyrolactone (GBL), or any combinations thereof.

9. The method of claim 1, further comprising:
providing an inlet stream comprising ethylene to an inlet of an oxidative reactor;
converting at least some of the ethylene to ethylene oxide (EO) to produce an outlet stream comprising EO;
directing the outlet stream comprising EO from the oxidative reactor to the inlet of the central reactor; and
converting at least some of the EO to BPL.

10. The method of claim 1, wherein the outlet stream comprising beta lactone is directed from the central reaction zone to the first C3 reactor and the first C4 reactor.

11. The method of claim 1, wherein the epoxide is ethylene oxide (EO) and the beta lactone is beta propiolactone (BPL).

12. The method of claim 4, wherein the PPL stream, the AA stream, and the acrylate ester stream are simultaneously produced.

13. The method of claim 4, further comprising modulating a ratio of PPL:AA:acrylate ester produced in the PPL stream, the AA stream, and the acrylate ester stream.

14. The method of claim 4, further comprising modulating the fraction of the PPL stream that is received by the second C3 reactor.

15. The method of claim 5, wherein two or more of the PPL stream, the AA stream, and the acrylate ester stream are simultaneously produced.

16. The method of claim 6, further comprising modulating the fraction of the PPL stream that is received by the second C3 reactor.

17. The method of claim 8, further comprising modulating a ratio of BDO:THF:GBL produced in the second C4 reactor.

18. The method of claim 6, wherein the PPL stream, the AA stream, and the SA stream are simultaneously produced.

19. The method of claim 6, further comprising modulating a ratio of PPL:AA:SA from the PPL stream, the AA stream, and the SA stream.

20. The method of claim 1, wherein the first $C_3$ product includes polypropiolactone, wherein the second $C_3$ product includes polyacrylic acid, and wherein the first $C_4$ product includes tetrahydrofuran and/or gamma butyrolactone.

* * * * *